United States Patent
Simon et al.

(10) Patent No.: US 10,832,819 B2
(45) Date of Patent: Nov. 10, 2020

(54) SYSTEMS AND METHODS FOR ELECTRONIC HEALTH RECORDS

(71) Applicant: Arcadia Solutions, LLC, Burlington, MA (US)

(72) Inventors: Michael A. Simon, Medford, MA (US); Nicholas Charles Wolfe Stepro, Cambridge, MA (US)

(73) Assignee: Arcadia Solutions, LLC, Burlington, MA (US)

( * ) Notice: Subject to any disclaimer, the term of this patent is extended or adjusted under 35 U.S.C. 154(b) by 598 days.

(21) Appl. No.: 14/815,290

(22) Filed: Jul. 31, 2015

(65) Prior Publication Data

US 2015/0347705 A1  Dec. 3, 2015

Related U.S. Application Data

(63) Continuation-in-part of application No. 14/724,478, filed on May 28, 2015, now abandoned.

(60) Provisional application No. 62/004,167, filed on May 28, 2014.

(51) Int. Cl.
   *G16H 50/30* (2018.01)
   *G16H 10/60* (2018.01)

(52) U.S. Cl.
   CPC .............. *G16H 50/30* (2018.01); *G16H 10/60* (2018.01)

(58) Field of Classification Search
   CPC ........ G16H 10/60; G16H 50/30; G16H 10/30; G06F 19/3431; G06F 19/322; G06F 19/00; G06F 17/3053; G06F 17/30914
   See application file for complete search history.

(56) References Cited

U.S. PATENT DOCUMENTS

| | | | |
|---|---|---|---|
| 6,491,629 B1 * | 12/2002 | Bousseljot | A61B 5/0452 600/300 |
| 6,607,480 B1 * | 8/2003 | Bousseljot | G16H 15/00 600/300 |
| 7,865,375 B2 * | 1/2011 | Lancaster | G06N 5/04 705/3 |
| 8,095,530 B1 | 1/2012 | Lloyd et al. | |
| 8,180,783 B1 | 5/2012 | Fletcher et al. | |
| 8,732,096 B1 * | 5/2014 | Glukhov | G16H 50/20 706/12 |
| 9,058,393 B1 | 6/2015 | Nicks et al. | |

(Continued)

*Primary Examiner* — William Spieler
(74) *Attorney, Agent, or Firm* — GTC Law Group PC & Affiliates

(57) ABSTRACT

A method of generating a clinically supplemented risk score using data from an electronic health record system can include collecting data from a plurality of electronic health records; parsing the data into defined fields; comparing the parsed data to at least one look-up table to generate an inferred diagnostic condition; comparing the inferred diagnostic condition to a documented diagnostic condition; mapping the inferred diagnostic condition to at least one condition category; refining the at least one mapped inferred diagnostic condition into a hierarchy to generate a hierarchal mapped conditioned category; and determining via a processor, a risk score in response to the inferred diagnostic condition for the patient in response to the hierarchal mapped conditioned category, the risk score representing an expected total cost of care for the patient relative to the average per-patient cost of care over an entire population.

20 Claims, 61 Drawing Sheets

(56) References Cited

U.S. PATENT DOCUMENTS

| | | | |
|---|---|---|---|
| 9,223,836 B1 | 12/2015 | Fletcher et al. | |
| 2001/0032257 A1* | 10/2001 | Wells | H04L 29/06 709/223 |
| 2002/0004725 A1* | 1/2002 | Martin | G06F 19/3481 705/2 |
| 2002/0194029 A1* | 12/2002 | Guan | G06Q 10/10 705/3 |
| 2003/0014284 A1* | 1/2003 | Jones | G06Q 30/02 705/3 |
| 2003/0097185 A1* | 5/2003 | Goetzke | G16H 50/20 700/1 |
| 2003/0167189 A1* | 9/2003 | Lutgen | G06F 19/322 705/3 |
| 2007/0179812 A1* | 8/2007 | Chapman | G16H 10/60 705/3 |
| 2007/0288247 A1 | 12/2007 | Mackay et al. | |
| 2008/0301571 A1* | 12/2008 | Herzog | G06Q 50/22 715/764 |
| 2009/0024006 A1* | 1/2009 | Bessette | A61B 5/00 600/301 |
| 2009/0138314 A1 | 5/2009 | Bruce et al. | |
| 2010/0153132 A1* | 6/2010 | Barth | G06Q 10/06 705/2 |
| 2010/0280350 A1* | 11/2010 | Zhang | A61B 5/4803 600/407 |
| 2013/0339030 A1* | 12/2013 | Ehsani | G10L 17/005 704/275 |
| 2014/0019128 A1* | 1/2014 | Riskin | G06Q 10/06 704/235 |
| 2014/0215495 A1* | 7/2014 | Erich | G06F 11/3438 719/318 |
| 2014/0369596 A1 | 12/2014 | Siskind et al. | |
| 2015/0012285 A1* | 1/2015 | Stambaugh | G06Q 50/22 705/2 |
| 2015/0019566 A1 | 1/2015 | Jones et al. | |
| 2015/0025903 A1* | 1/2015 | Mueller-Wolf | G06F 19/3425 705/2 |
| 2015/0088548 A1* | 3/2015 | Charlot | G16H 10/60 705/3 |
| 2015/0142701 A1* | 5/2015 | Ashparie | G06F 19/345 706/11 |
| 2015/0317743 A1* | 11/2015 | Flam | G06Q 10/10 705/4 |
| 2015/0347599 A1 | 12/2015 | McMains et al. | |

\* cited by examiner

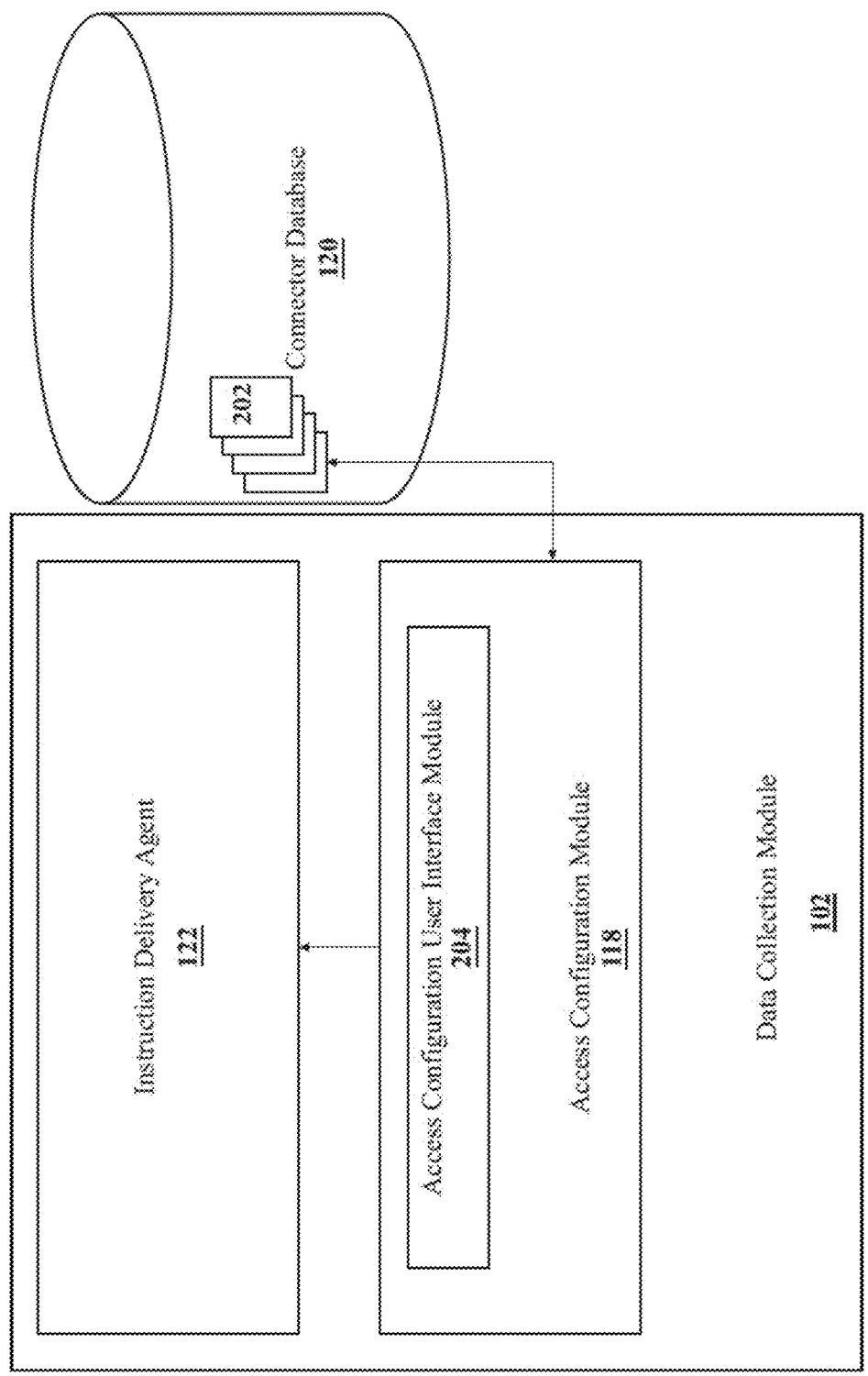

202A

| Edit | Delete |

Mapplet Details

| | |
|---|---|
| Mapplet Name:* | ARC_mplt_Intergy_6_Allergy_1 |
| Description: | Uploaded by the awesome SQL Transformer |
| Mapplet Type: | Active |
| Mapplet Xml File:* | Intergy_6_Allergy_1.xml |
| Created On: | Apr 7, 2014 12:15:33 AM May 22, 2014 |
| Updated On: | 2:33:33 PM |
| Created By: | email1@company.com |
| Updated By: | email2@company.com |

Mapplet Xml File Details (Intergy_6_Allergy_1.xml)

| Connections | |
|---|---|
| Connection Reference | Type |
| TheConnection | Microsoft SQL Server |

302 — Input Fields

| Info | Name |
|---|---|
| 📄 | DBID |
| 📄 | Lower_Bound |
| 📄 | Upper_Bound |
| 📄 | LoadedFromFile |
| 📄 | OtherParam |

308 304 — Output Fields

| Info | Name |
|---|---|
| 📄 | SQLError |
| 📄 | center_id |
| 📄 | allergy_id |
| 📄 | patient_id |
| 📄 | encounter_id |
| 📄 | type |
| 📄 | description |
| 📄 | reaction |
| 📄 | ndc_code |

Mapping Configuration Task Wizard (Encounter_1)

| 1 Definition | 2 Sources | 3 Targets | 4 Other Parameters | 5 Schedule |

[< Previous] [Next >] [Save ▼] [Cancel] | [Validate]

Mapplet Details
Smpt_Intergy_6_Encounter_1S(The Connection): *  [SQL_Intergy ▼] [View]
☑ Display technical field names instead of labels
☑ Display Mapplet fields in alphabetical order

302A

Other Parameter Details ⟵ 404

$DBD$:*  
[001]

$ExcludedrsncdDescriptionList$:*  
[]|CHR(39)|[No Show]|CHR(39)|[]

$LoadedFromFile$:*  
[2014_05_28_102748_001_001_Encounter.csv]

$Lower_Bound$:*  
[05/27/2014]

$OfficeD$:*  
[]|CHR(39)|[DGLN]|CHR(39)|[]

$OtherParam$:*  
[/**/]

$UpperBound$:*  
[05/28/2014]

Task Flow Details

| | |
|---|---|
| Task Flow Name:* | Intergy_Extract |
| Description: | |
| Schedule: | |
| Created On: | Apr 23, 2014 6:03:14 PM May 27, 2014 |
| Updated On: | 1:30:03 PM |
| Created By: | email1@company.com |
| Updated By: | email2@company.com |
| Last Run: | May 6, 2014 2:08:50 PM |

List of Tasks

List of Sequence:* — 502:
- Intergy_Allergy_1
- Intergy_Appointment_1 SLVTN_Intergy_Assessment_1
- Intergy_Charge_1
- Intergy_Encounter_1 SLVTN_Intergy_Immunization_1
- Intergy_Medicationlist_1
- Intergy_Order_1
- Intergy_Patient_1
- Intergy_Payer_1
- Intergy_Prescription_1
- Intergy_Problem_1
- Intergy_Provider_1
- Intergy_Results_1
- Intergy_Vitals_1
- Intergy_Maintenance_ClinicalCustomFinding_1
- Intergy_Maintenance_MedcinFinding_1
- Intergy_Maintenance_iETLReasonCodeEncounter_1
- Intergy_Maintenance_iETLReasonCodeAppointment_1
- Intergy_Maintenance_CTMTask_1
- Intergy_Maintenance_PatientEHRFile_1
- Intergy_Maintenance_ODSCustomFinding_1
- Intergy_Encrypt
- Intergy_SFTP SLVTN_Intergy_Delete_SFTP_SuccessFiles

Email Notification Options

Use custom email notification options for this task:

FIG. 5A

New Schedule

A schedule specifies when and how often a job runs. Enter a name, start time, and repeat frequency for the schedule.

Schedule Name:* `Test Schedule`

Description: `Run once a day`

Starts:* `05/27/2014` at `14` : `30`

Repeats: `Daily`

---

Repeat Frequency Options: Daily

Run the task:
- ○ Every day
- ● Every weekday

Repeat Options:
- ● Repeat indefinitely
- ○ Repeat until `05/27/2014` at `15` : `00`

[OK] [Cancel]

FIG. 5B

| Tablename | ColumnName | CodeSet | CodeSet | CodeCount | tableRecords | As % of Patients | As % of Visits | Index |
|---|---|---|---|---|---|---|---|---|
| Encounter | Enc Updated Timestamp | | | 482997 | 2464824 | 100% | 100% | l_encounterle |
| Encounter | Tencounterid | | | 482997 | 2464824 | 100% | 100% | l_encounterlT |
| Immunization | Completed Date | | | 257399 | 3168612 | 100% | 53% | l_immunizatio |
| Immunization | Delete Ind | | N | 257399 | 3168612 | 100% | 53% | l_immunizatio |
| Immunization | Enc Id | | | 38398 | 3168612 | 59% | 23% | l_immunizatio |
| Immunization | Imm Type | Imm Type | Dtp | 36981 | 3168612 | 57% | 22% | l_immunizatio |
| Immunization | Imm Type | Imm Type | Flu | 47774 | 3168612 | 73% | 29% | l_immunizatio |
| Immunization | Imm Type | Imm Type | Hepa | 8606 | 3168612 | 36% | 5% | l_immunizatio |
| Immunization | Imm Type | Imm Type | Hepb | 26715 | 3168612 | 40% | 16% | l_immunizatio |
| Immunization | Imm Type | Imm Type | Hib | 26765 | 3168612 | 41% | 16% | l_immunizatio |
| Immunization | Imm Type | Imm Type | Ipv | 29895 | 3168612 | 74% | 18% | l_immunizatio |
| Immunization | Imm Type | Imm Type | Mcv | 4550 | 3168612 | 19% | 3% | l_immunizatio |
| Immunization | Imm Type | Imm Type | Mmr | 14681 | 3168612 | 91% | 9% | l_immunizatio |
| Immunization | Imm Type | Imm Type | Pcv | 23361 | 3168612 | 22% | 14% | l_immunizatio |
| Immunization | Imm Type | Imm Type | Rot | 5179 | 3168612 | 21% | 3% | l_immunizatio |
| Immunization | Imm Type | Imm Type | Td | 4666 | 3168612 | 19% | 3% | l_immunizatio |
| Immunization | Imm Type | Imm Type | Vrc | 11691 | 3168612 | 48% | 7% | l_immunizatio |
| Immunization | Patient Id | | | 257399 | 3168612 | 100% | 15% | l_immunizatio |
| Maintenance | Maint Completed By Prov | | | 19993 | 67859096 | 80% | 12% | l_maintenanc |
| Maintenance | Maint Completed Date | Maintenance | | 499704 | 67859096 | 20% | 20% | l_maintenanc |
| Maintenance | Maint Completed Date | | | 499704 | 67859096 | 20% | 30% | l_maintenanc |

1. Minimal/No Pre-Visit Planning
2. Front Office Answering Phones and Greeting, Patient Waits
3. Roomed and Left Alone
4. Physician Arrives Late, Does All Documentation and History
5. Handoff Discussion Between Physician and Mid, Orders Made
6. Check-Out, Told to Call for Follow-Ups
7. Closes Record After-Hours, Orders Additional Labs/Referrals Requiring Call the Next Day

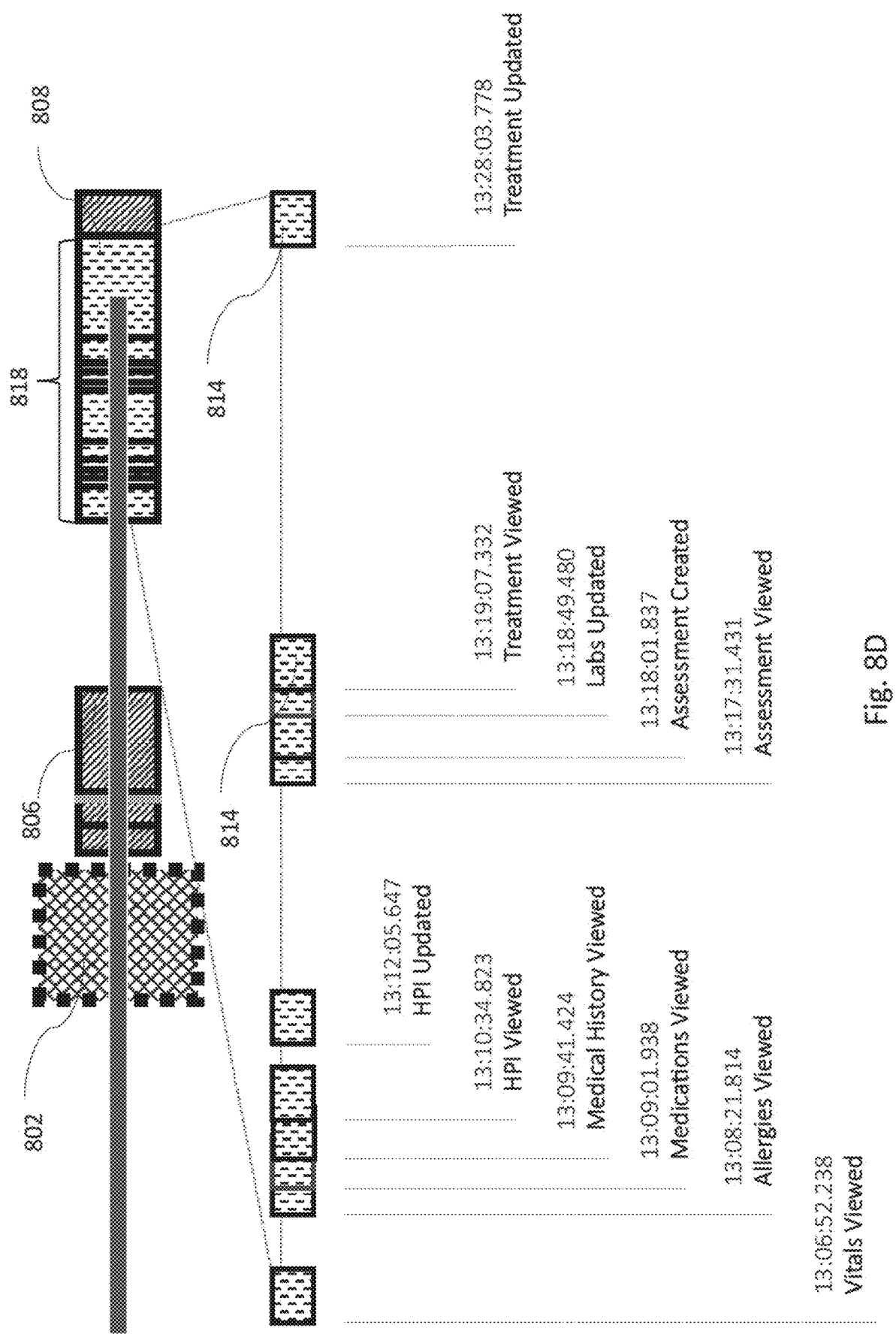

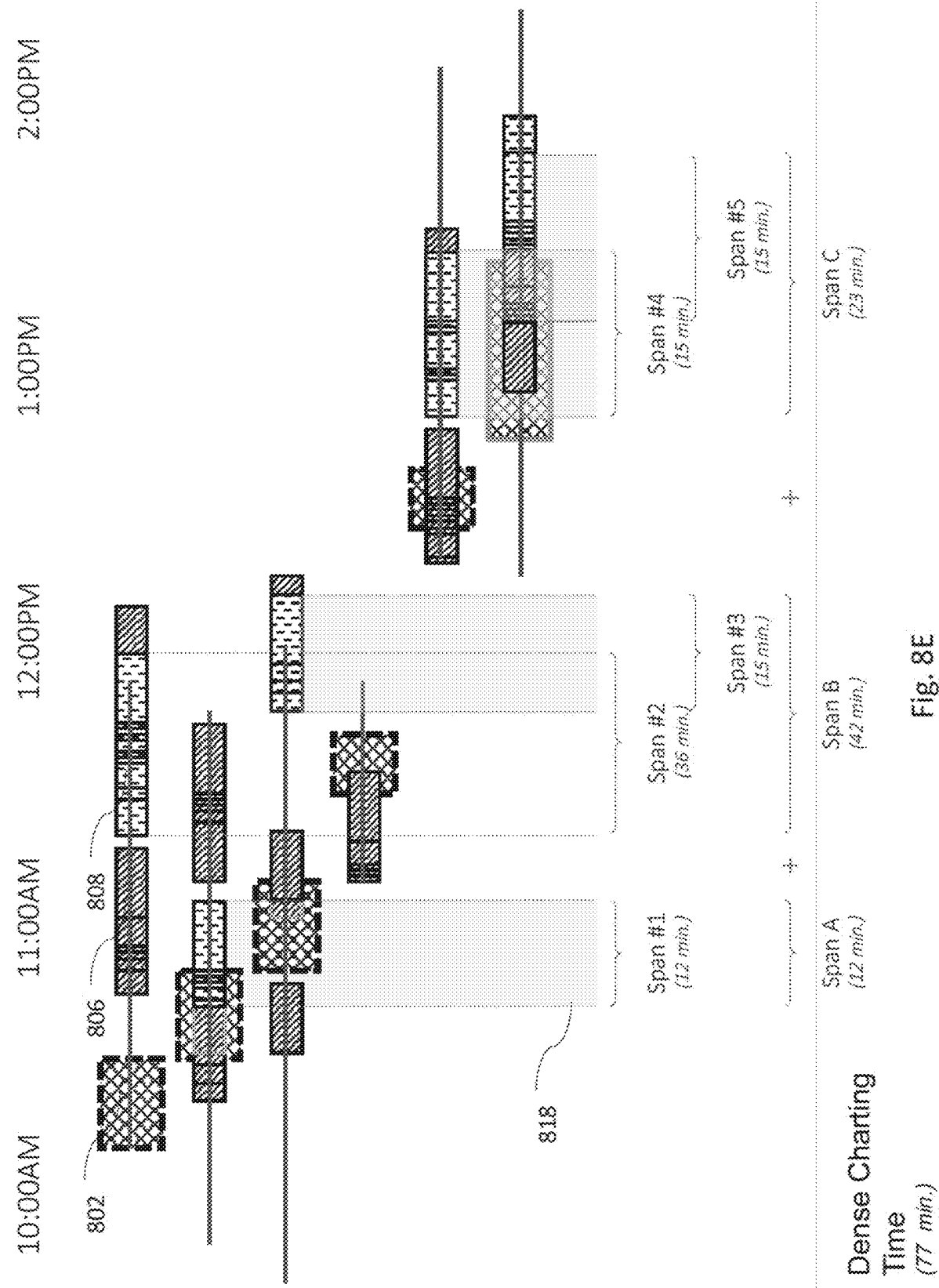

FIG. 9A

PERFORMANCE    UTILIZATION    PATIENT
MANAGEMENT      ANALYSIS      MANAGEMENT                    ADMIN    LOGOUT

USER: USER1@COMPANY.COM
              ╲ 1108
User is Admin?
User Attribution:     Facilities  ☑All
User Type:            clinical    ▶
Provider Attribution: functional  ▶
                                  ▶
                                              ╲ 1110
                                  Providers   ☑All Save 1112 ─ (User is Admin?)
1102 ─ (User Attribution)
1104 ─ (Provider Attribution)

HEALTHCARE SOLUTIONS        USER MANUAL    REPORT ISSUE    CONTACT US

HIGH RISK

| | Name | Risk Score | Pmpy Actual | Pmpy Annual | Most Recen... | Rendering P... |
|---|---|---|---|---|---|---|
| | Filter... | =10 | >50,000 | Filter... | >1/1/2014 | Filter... |
| ☒ | Abbott, Catri... Marquez, Elmer | 10 | $99,000 | $237,600 | 5/3/2014 | |
| ☒ | ABBOTT, MAD... Alvarado, Cas... | 10 | $72,000 | $123,429 | 5/15/2014 | |
| ☒ | Acevedo, Cha... Arnold, Dahlia | 10 | $71,000 | $170,400 | 5/17/2014 | |
| ☒ | Acosta, Carisa t Sears, Deven | 10 | $90,000 | $216,000 | 3/10/2014 | |
| ☒ | Acosta, Gem... Levy, Merrit | 10 | $80,000 | $137,143 | 3/10/2014 | |
| ☒ | Adkins, Dina t Emerson, Neva | 10 | $94,000 | $225,600 | 5/20/2014 | |
| ☒ | Adkins, Letitia t Chapman, Mi... | 10 | $88,000 | $211,200 | 5/17/2014 | |
| ☒ | Aguilar, Alexa... Trujillo, Jeani... | 10 | $71,000 | $121,714 | 2/24/2014 | |
| ☒ | AGUILAR, CA... Durham, Carley | 10 | $85,000 | $204,000 | 5/21/2014 | |
| ☒ | Aguilar, Cress... Odonnell, Jaret | 10 | $58,000 | $99,429 | 5/22/2014 | |
| ☒ | Aguirre, Cheri... Barton, Riya | 10 | $54,000 | $129,600 | 5/22/2014 | |
| ☒ | Alexander, Im... Ewing, Aline | 10 | $88,000 | $150,857 | 4/11/2014 | |
| ☒ | Alexander, Ja... Benjamin, Be... | 10 | $52,000 | $89,143 | 5/16/2014 | |
| ☒ | Alexander, Ro... Soto, Alpha | 10 | $51,000 | $87,429 | 5/22/2014 | |
| ☒ | Alford, Anna... Sherman, Gust | 10 | $93,000 | $159,429 | 5/20/2014 | |
| ☒ | Alford, Jolene e Vazquez, Doris | 10 | $82,000 | $140,571 | 4/26/2014 | |

FIG. 12A-1

| | Next Appol... Filter | Next Appol... Filter | Most Recen... Filter | Most Recen... Filter |
|---|---|---|---|---|
| | 6/16/2014 | Mcconnell, K... | 5/3/2014 | Type: Inpatient |
| | 6/7/2014 | Charles, Shalon | 5/15/2014 | Type: Emerge... |
| | 5/26/2014 | Ford, Damion | 5/17/2014 | Type: Emerge... |
| | | | 3/10/2014 | Type: Emerge... |
| | | | 1/26/2014 | Type: Inpatient |
| | | | 5/20/2014 | Type: Inpatient |
| | 6/29/2014 | Trujilo, Jeani... | 5/7/2014 | Type: Emerge... |
| | 2/18/2015 | Odonnell, Janet | 5/21/2014 | Type: Emerge... |
| | 6/7/2014 | Wynn, Shandra | 5/22/2014 | Type: Inpatient |
| | 5/23/2014 | Walker, Felecia | 3/26/2014 | Type: Emerge... |
| | 5/31/2014 | Webb, Kori | 1/28/2014 | Type: Emerge... |
| | 6/2/2014 | Joyner, Julús | 5/22/2014 | Type: Inpatient |
| | 6/13/2014 | Joyner, Hake... | 4/26/2014 | Type: Inpatient |
| | | | 4/14/2014 | Type: Inpatient |

1212

Results per Page: 20

FIG. 12A-2

Hypothetical example of CMS-HCC (version 12) expenditure predictions and risk score community-residing, 76-year-old woman with AMI, angina pectoris, COPD, renal failure, chest pain and ankle sprain

| Risk Marker | Risk Type | Incremental Prediction | TOTAL Relative Risk Coefficient | CLOSED Relative Risk Coefficient |
|---|---|---|---|---|
| Female, age 75-79 | CLOSED | $3,409 | 0.457 | 0.457 |
| Acute myocardial infarction (HCC 81) | OPEN | $2,681 | 0.359 | -- |
| Angina pectoris (HCC 83)¹ | CLOSED | $0 | -- | 0.150 |
| Chronic obstructive pulmonary disease (HCC 108) | CLOSED | $2,975 | 0.399 | 0.399 |
| Renal failure (HCC 131) | OPEN | $2,745 | 0.368 | -- |
| Chest pain (HCC 166)² | CLOSED | $0 | -- | -- |
| Ankle Sprain (HCC 162)² | OPEN | $0 | -- | -- |
| Total | TOTAL RISK | $11,810 | 1.583 | |
| | CLOSED RISK | | | 1.006 |

NOTES:
1. HCC 83 Angina Pectoris has an incremental prediction, but the amount is not added because HCC 81 Acute Myocardial Infarction is within the same hierarchy and is the more severe manifestation of cardiovascular disease.
2. Chest pain (symptom associated with a variety of medical conditions from minor to serious) and ankle sprain (typically transitory) are excluded from the payment model.

SOURCE: RTI International

FIG. 12F

| HCC | DESCRIPTION | CATEGORY | UPSIDE | OPP TYPE |
|---|---|---|---|---|
| HCC135 | Acute Renal Failure | Kidney | $260 | 4| Investigate - Prescription/Medication |
| HCC023 | Other Significant Endocrine and Metabolic Disorders | Metabolic | $1,670 | 5| Opportunity - Problem List |
| HCC054 | Drug/Alcohol Psychosis | Substance Abuse | $3,698 | 6| Investigate - Non E&M Claim/Encounter |
| HCC170 | Hip Fracture/Dislocation | Injury | $4,014 | 7| Investigate - Historical HCC/Claim |
| HCC111 | Chronic Obstructive Pulmonary Disease | Lung | $3,120 | 7| Investigate - Historical HCC/Claim |
| HCC084 | Cardio-Respiratory Failure and Shock | Arrest | $2,243 | 7| Investigate - Historical HCC/Claim |
| HCC079_v12 | Cardio-Respiratory Failure and Shock | Arrest | $1,189 | 7| Investigate - Historical HCC/Claim |
| HCC104_v12 | Vascular Disease with Complications | Vascular | $264 | 7| Investigate - Historical HCC/Claim |
| HCC017 | Diabetes with Acute Complications | Diabetes | $0 | 7| Investigate - Historical HCC/Claim |

FIG. 13C

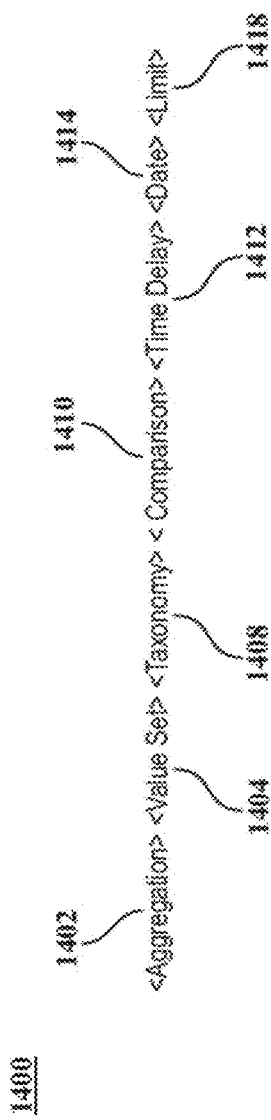
FIG. 14
FIG. 15A
FIG. 15B

1600 — "HEDIS CAD/IVD" Procedure During 3 Years Before Period End AND Age at Period End Between 18 and 85 AND "HEDIS CAD/IVD" Diagnosis During Period

FIG. 16A

| Logical 1602 | Aggregation 1402 | Value Set 1404 | Taxonomy 1408 | Comparison 1410 | Time Delay 1412 | Date 1414 | Limit 1418 |
|---|---|---|---|---|---|---|---|
| AND | Age at 1402C | HEDIS CAD/IVD 1404B | Procedure 1408B | During 1410B | 3 Years Before 1412B | Period End 1414B | |
| | | | | | | Period End 1414C | Between 18 and 85 1418C |
| AND | | HEDIS CAD/IVD 1404D | Diagnosis 1408D | During 1418D | | Period 1418D | |

Numerator 1702: Most recent LDL result during 1 year before period end < 100

Denominator 1704: HEDIS CAD/IVD procedure during 3 years before period end

FIG. 18

Numerator 1702E:

| Aggregation 1402 | Value Set 1404 | Taxonomy 1408 | Comparison 1410 | Time Delay 1412 | Date 1414 | Limit 1418 |
|---|---|---|---|---|---|---|
| Most recent 1402E | LDL 1404E | Result 1408E | During 1410E | 1 Year before 1412E | Period End 1414E | <100 1418E |

Numerator 1704E:

| Aggregation 1402 | Value Set 1404 | Taxonomy 1408 | Comparison 1410 | Time Delay 1412 | Date 1414 | Limit 1418 |
|---|---|---|---|---|---|---|
| | HEDIS CAD/IVD 1404E | Procedure 1408E | During 1410E | 3 Years before 1412E | Period End 1414E | |

```
CREATE function [rpt].[fnMeasureTest] (@period_start_date date,
@period_end_date date)

RETURNS TABLE AS
RETURN

WITH
most_recent_ldl_Result_during_1yearbeforeperiod_end as (
select
   IndividualID
   ,count(1) as aggregate
   ,max(case when rank = 1 then value end) Value
   -- TODO change max/case to just select rank = 1 when no aggregate
   ,max(case when rank = 1 then ValueStr end) ValueStr
   ,max(case when rank = 1 then ProviderID end) ProviderID
   ,max(case when rank = 1 then LocationID end) LocationID
   ,max(case when rank = 1 then SourceID end) SourceID
   ,max(case when rank = 1 then StartDate end) StartDate
   ,max(case when rank = 1 then EndDate end) EndDate
from
(select
e.IndividualID
           ,e.Value value
           ,e.ValueStr ValueStr
 ,e.ProviderId Provider ID
 ,e.LocationId LocationID
 ,e.SourceID SourceID
 ,e.StartDate StartDate
 ,e.StartDate EndDate
 ,ROW_NUMBER() over (PARTITION BY e.IndividualID order by e.StartDate desc,
e.value asc) rank
from
rpt.Event e with (nolock)

where
   EventCodeID in (33090)
   and SourceID <1000 and e.StartDate <= @period_end_date and e.StartDate >= dateadd(day, 1,
dateadd(year, -1, @period_end_date))

) a group by IndividualID)
```

FIG. 22A

```
,count_arcadia_hedis_cad_ivd_Procedure_during_3yearsbeforeperiod_end as (
select IndividualID ,count(1) as aggregate ,max(case when rank=1 then value end)Value
-- TODO change max/case to just select rank = 1 when no aggregate
,max(case when rank = 1 then ValueStr end) ValueStr
,max(case when rank = 1 then ProviderID end) ProviderID
,max(case when rank = 1 then LocationID end) LocationID
,max(case when rank = 1 then SourceID end) SourceID
,max(case when rank = 1 then StartDate end) StartDate
,max(case when rank = 1 then EndDate end) EndDate from
  (select
   e.IndividualID
        ,e.Value value
        ,e.ValueStr ValueStr
,e.ProviderId ProviderID
,e.LocationId LocationID
,e.SourceID SourceID
,e.StartDate StartDate
,e.StartDate EndDate
,ROW_NUMBER() over (PARTITION BY e.IndividualID order by e.StartDate desc,
e.value asc) rank from
   rpt.Event e with (nolock)
where          ~2204A
   EventCodeID in
(9298,9300,9302,9304,9306,9308,9309,9323,9325,9332,9887,9888,9889,9890,9891
,9892,9893,9894,9895,9896,9901,9902,9903,9907,9908,9909,9913,9914,9915,9916,
9917,9918,9919,9920,9921,9922,9923,9924,9931,9954,9955,9956,9957,9958,9959,
9960,9961,9962,9981,9982,9983,9984,9985,9986,9987,9988,9989,9990,9991,9992,
9993,9994,9995,9996,9997,9998,10003,10004,10005,10006,10017,10018)
   and SourceID<1000
   and e.StartDate <= @period_end_date and e.StartDate >=dateadd(day, 1,
dateadd(year, -3, @period_end_date))
) a
group by IndificualID)              ~2208B
```

```
SELECT 1 as denominator

, case when
most_recent_ldl_Result_during_1yearbeforeperiod_end_value          ← 2210
100 then 1 else 0 end as numerator
,0 as exclusion
,0 as exception
,grp.IndividualID
,most_recent_ldl_Result_during_1yearbeforeperiod_end_StartDate,
most_recent_ldl_Result_during_1yearbeforeperiod_end_EndDate,
most_recent_ldl_Result_during_1yearbeforeperiod_end_ValueStr,
most_recent_ldl_Result_during_1yearbeforeperiod_end_ProviderId,
most_recent_ldl_Result_during_1yearbeforeperiod_end_LocationId,
most_recent_ldl_Result_during_1yearbeforeperiod_end_SourceID,most_r
ecent_ldl_Result_during_1yearbeforeperiod_end_Value,most_recent_ldl_
Result_during_1yearbeforeperiod_end_count ,count_arcadia_hedis_cad_ivd_Procedure_during_3yearsbeforeperiod_and
_StartDate,
count_arcadia_hedis_cad_ivd_Procedure_during_3yearsbeforeperiod_and
_EndDate,
count_arcadia_hedis_cad_ivd_Procedure_during_3yearsbeforeperiod_and
_ValueStr,
count_arcadia_hedis_cad_ivd_Procedure_during_3yearsbeforeperiod_and
_ProviderId,
count_arcadia_hedis_cad_ivd_Procedure_during_3yearsbeforeperiod_and
_LocationId,
count_arcadia_hedis_cad_ivd_Procedure_during_3yearsbeforeperiod_and
_SourceID,count_arcadia_hedis_cad_ivd_Procedure_during_3yearsbefore
period_end_Value,count_arcadia_hedis_cad_ivd_Procedure_during_3year
sbeforeperiod_end_count
```

FIG. 22C

```
FROM (

SELECT
IndividualID
,max(case when MetricName =
'most_recent_ldl_Result_during_1yearbeforeperiod_end' then StartDate end) as
'most_recent_ldl_Result_during_1yearbeforeperiod_end_StartDate
,max(case when MetricName =
'most_recent_ldl_Result_during_1yearbeforeperiod_end' then EndDate end) as
'most_recent_ldl_Result_during_1yearbeforeperiod_end_EndDate
,max(case when MetricName =
'most_recent_ldl_Result_during_1yearbeforeperiod_end' then ValueStr end) as
'most_recent_ldl_Result_during_1yearbeforeperiod_end_ValueStr
,max(case when MetricName =
most_recent_ldl_Result_during_1yearbeforeperiod_end' then Value end) as
'most_recent_ldl_Result_during_1yearbeforeperiod_end_Value
,max(case when MetricName =
most_recent_ldl_Result_during_1yearbeforeperiod_end' then ProviderID end) as
'most_recent_ldl_Result_during_1yearbeforeperiod_end_ProviderId
,max(case when MetricName =
most_recent_ldl_Result_during_1yearbeforeperiod_end' then LocationID end) as
'most_recent_ldl_Result_during_1yearbeforeperiod_end_LocationId
,max(case when MetricName =
most_recent_ldl_Result_during_1yearbeforeperiod_end' then SourceID end) as
'most_recent_ldl_Result_during_1yearbeforeperiod_end_SourceID
,snull(max(case when MetricName=
most_recent_ldl_Result_during_1yearbeforeperiod_end' then aggregate end),0)as
'most_recent_ldl_Result_during_1yearbeforeperiod_end_count
```

FIG. 22D

```
,max(case when MetricName=
'count_arcadia_hedis_cad_ivd_Procedure_during_3yearsbeforeperiod_end_StartDate
end) as
'count_arcadia_hedis_cad_ivd_Procedure_during_3yearsbeforeperiod_end_StartDate
,max(case when MetricName=
'count_arcadia_hedis_cad_ivd_Procedure_during_3yearsbeforeperiod_end_EndDate
end) as
'count_arcadia_hedis_cad_ivd_Procedure_during_3yearsbeforeperiod_end'then ValueStr
end) as
'count_arcadia_hedis_cad_ivd_Procedure_during_3yearsbeforeperiod_end_ValueStr
,max(case when MetricName=
'count_arcadia_hedis_cad_ivd_Procedure_during_3yearsbeforeperiod_end' then Value
end) as count_arcadia_hedis_cad_ivd_Procedure_during_3yearsbeforeperiod_end_Value
,max(case when MetricName=/                                                          910
'count_arcadia_hedis_cad_ivd_Procedure_during_3yearsbeforeperiod_end' then
ProviderID end) as
'count_arcadia_hedis_cad_ivd_Procedure_during_3yearsbeforeperiod_and_ProviderId
,max(case when MetricName=
'count_arcadia_hedis_cad_ivd_Procedure_during_3yearsbeforeperiod_end' then
LocationID and) as
'count_arcadia_hedis_cad_ivd_Procedure_during_3yearsbeforeperiod_end_LocationId
,max(case when MetricName=
'count_arcadia_hedis_cad_ivd_Procedure_during_3yearsbeforeperiod_end' then SourceID
end) as
'count_arcadia_hedis_cad_ivd_Procedure_during_3yearsbeforeperiod_end_SourceID
,isnull(max(case when MetricName=
'count_arcadia_hedis_cad_ivd_Procedure_during_3yearsbeforeperiod_end' then
aggregate end),0)as
'count_arcadia_hedis_cad_ivd_Procedure_during_3yearsbeforeperiod_end_count
FROM (
select 'most_recent_ldl_Result_during_1yearbeforeperiod_end'MetricName,
IndividualID, StartDate, EndDate, Value value, ValueStr ValueStr ,aggregate, LocationID,
SourceID, ProviderID from most_recent_ldl_Result_during_1yearbeforeperiod_end
union all select
'count_arcadia_hedis_cad_ivd_Procedure_during_3yearsbeforeperiod_end' MetricName,
IndividualID, Startdate, EndDate, Value value, ValueStr, aggrgate, LocationID,
SourceID, ProviderID from
'count_arcadia_hedis_cad_ivd_Procedure_during_3yearsbeforeperiod_end
)union_qry
GROUP BY IndividualID) qrp
WHERE
'count_arcadia_hedis_cad_ivd_Procedure_during_3yearsbeforeperiod_end_count>0
```

| Individual ID | Denominator | Numerator | Exclusion | Exception | Date-Most Recent Ldl Result During 1Year Before Period End | Provider-Most Recent Ldl Result During 1Year Before Period End | Location-Most Recent Ldl Result During 1Year Before Period End | Data Source-Most Recent Ldl Result During 1Year Before Period End | Value-Most Recent Ldl Result During 1Year Before Period End | Date-Cad/vd Procedure During 3 Years Before Period End | Code-Cad/vd Procedure During 3 Years Before Period End | Provider-Cad/vd Procedure During 3 Years Before Period End | Location-Cad/vd Procedure During 3 Years Before Period End | Data Source-Cad/vd Procedure During 3 Years Before Period End |
|---|---|---|---|---|---|---|---|---|---|---|---|---|---|---|
| Adams, John | 1 | 1 | 0 | 0 | 1/1/2015 | Dr Lewis | ABC Family Medicine | ABC EHR | 90 | 1/25/2015 | 92920 | Dr Jones | St Elizabeths | St Elizabeths EHR |
| Smith, Frank | 0 | 0 | 0 | 0 | | | | | | | | | | |
| Arugala, Kate | 0 | 0 | | | | | | | | | | | | |
| Frank, Adam | | | | | 2/15/2015 | Dr Lewis | ABC Family Medicine | ABC EHR | 85 | 3/3/13 | 92920 | Dr Jones | St Elizabeths | St Elizabeths |

| PERFORMANCE | UTILIZATION | PATIENTS | OPERATIONS | ADMIN LOGOUT |

DM LDL CONTROL 100

| Name | Functional PCP | Calc Numerat | Calc Denomin | Numerator | Denominator | Exclusions | Exceptions | Last Visit Date | Interaction Date | Next Appt Date |
|---|---|---|---|---|---|---|---|---|---|---|
| Filter... | Filter... | 0 | Filter... | Filter... | Filter... | Filter... | Filter... | Filter... | Filter... | Filter... |
| Adkins, Zek... | Joyner, Hake... | 0 | 1 | 0 | 1 | 0 | 0 | 2/28/2015 | 2/28/2015 | |
| AGUILAR, K... | Joyner, Hake... | 0 | 1 | 0 | 1 | 0 | 0 | 1/3/2015 | 1/3/2015 | |
| AGUILAR, K... | Joyner, Hake... | 0 | 1 | 0 | 1 | 0 | 0 | 4/24/2012 | 12/21/2013 | |
| AGUILAR, M... | Joyner, Hake... | 0 | 1 | 0 | 1 | 0 | 0 | 8/6/2013 | 5/24/2014 | |
| ALFORD, P... | Joyner, Hake... | 0 | 1 | 0 | 1 | 0 | 0 | 2/27/2015 | 2/27/2015 | |
| ALFORD, P... | Joyner, Hake... | 0 | 1 | 0 | 1 | 0 | 0 | 4/11/2008 | 5/3/2014 | |
| ALLISON, R... | Joyner, Hake... | 0 | 1 | 0 | 1 | 0 | 0 | 2/26/2015 | 2/26/2015 | |
| Alston, Hyf... | Joyner, Hake... | 0 | 1 | 0 | 1 | 0 | 0 | 11/11/2014 | 11/11/2014 | |
| Alston, La... | Joyner, Hake... | 0 | 1 | 0 | 1 | 0 | 0 | 3/12/2015 | 3/12/2015 | |
| ALSTON, R... | Joyner, Hake... | 0 | 1 | 0 | 1 | 0 | 0 | 9/8/2014 | 9/8/2014 | |
| Alvarado, C... | Joyner, Hake... | 0 | 1 | 0 | 1 | 0 | 0 | 2/17/2015 | 2/17/2015 | 9/27/2015 |
| ALVAREZ, B... | Joyner, Hake... | 0 | 1 | 0 | 1 | 0 | 0 | 12/14/2012 | 2/1/2014 | |
| Alvarez, Er... | Joyner, Hake... | 0 | 1 | 0 | 1 | 0 | 0 | 2/13/2015 | 2/13/2015 | 6/16/2015 |
| ANDERSON... | Joyner, Hake... | 0 | 1 | 0 | 1 | 0 | 0 | 6/9/2012 | 5/17/2014 | |
| Andrews, P... | Joyner, Hake... | 0 | 1 | 0 | 1 | 0 | 0 | 4/10/2015 | 4/10/2015 | 1/16/2016 |

Results per Page: 20

USER MANUAL   REPORT ISSUE

FIG. 27

SYSTEMS AND METHODS FOR ELECTRONIC HEALTH RECORDS

CROSS REFERENCE TO RELATED APPLICATION

This application is a continuation-in-part of U.S. application Ser. No. 14/724,478, filed May 28, 2015. U.S. application Ser. No. 14/724,478 claims the benefit of U.S. Provisional Application Ser. No. 62/004,167, filed on May 28, 2014, and entitled "Electronic Health Record Data Mining System".

The above applications are incorporated herein by reference in their entirety.

BACKGROUND

1. Field

The present disclosure is generally related to healthcare-related assessments involving a plurality of data sources.

2. Description of Related Art

There are currently a large number of commercially available systems for the capture and management of electronic health records (EHR). One anticipated benefit of EHR is the potential to analyze the collected data for trends in patient health, organizational operation and the like. However, it is currently relatively difficult to merge information stored in different EHR systems, as well as merge information across different instances of the same vendor system, as there may be limited consistency between these. Many EHR systems are custom installations with limited ability to leverage earlier installations. The complexity still further increases when attempts are made to merge other data such as health insurance claims, facilities usage, and the like.

Beyond the difficulty of gathering the data into a single organized data set, there may still be difficulties in extracting the information desired from the data. Historically, it can take a significant amount of time for a person skilled in database operations and organization to craft a complex database query. Although it may be possible for someone skilled with databases to generate queries to extract information, it may not be ideal, since, in addition to the time element of formulating the queries, such individuals typically do not have the clinical or healthcare system understanding to effectively develop appropriate queries.

SUMMARY

In accordance with exemplary and non-limiting embodiments, systems and methods for the configuration and operation of a system for extracting data from a plurality of electronic health record systems and facilitating quick, easy access to desired subsets of the data are described.

The present disclosure describes a method of query phrase extraction, the method according to one disclosed non-limiting embodiment of the present disclosure can include receiving a query phrase for data from electronic health records, the query phrase including a numerator and a denominator; translating the query phrase into a first database query with predefined query generation syntax associated with the numerator and a second database query with predefined query generation syntax associated with the denominator; and determining a relationship between the numerator and the denominator.

A further embodiment of any of the foregoing embodiments of the present disclosure may include, wherein the translating the query phrase into a database query with predefined query generation syntax includes parsing the query phrase into predefined fields.

A further embodiment of any of the foregoing embodiments of the present disclosure may include, wherein the predefined fields includes aggregation, value set, value identifies, taxonomy, data table ID, comparison, time delay, date, and limit.

A further embodiment of any of the foregoing embodiments of the present disclosure may include, wherein the relationship includes a ratio.

A further embodiment of any of the foregoing embodiments of the present disclosure may include, wherein the first database query is a subset of the second database query.

A further embodiment of any of the foregoing embodiments of the present disclosure may include, wherein the first database query includes a first multiple of database queries, and the second database query includes a multiple of second database queries.

A further embodiment of any of the foregoing embodiments of the present disclosure may include, wherein the query phrase is received in plain language A further embodiment of any of the foregoing embodiments of the present disclosure may include, further comprising generating a table of results for the ratio of the results of the numerator divided by the denominator.

A further embodiment of any of the foregoing embodiments of the present disclosure may include, further comprising generating a table of results for the ratio of the results of the numerator divided by the denominator.

A further embodiment of any of the foregoing embodiments of the present disclosure may include, further comprising providing detailed traceability of each result accessible through the table of results.

A further embodiment of any of the foregoing embodiments of the present disclosure may include, wherein the traceability of each result is provided in near real time.

A further embodiment of any of the foregoing embodiments of the present disclosure may include, further comprising generating a graphical user interface for the ratio of the results of the numerator divided by the denominator.

A further embodiment of any of the foregoing embodiments of the present disclosure may include, wherein the traceability of each result is provided in near real time.

A further embodiment of any of the foregoing embodiments of the present disclosure may include, wherein determining the relationship between the numerator and the denominator includes exclusions.

A further embodiment of any of the foregoing embodiments of the present disclosure may include, wherein the exclusion includes a factor non-applicable the numerator and the denominator.

A further embodiment of any of the foregoing embodiments of the present disclosure may include, wherein a ratio of the numerator and the denominator is a performance rate associated with the first database query and the second database query.

A further embodiment of any of the foregoing embodiments of the present disclosure may include, wherein the denominator is 1 and the relationship is an absolute count.

A method of query phrase extraction, the method according to one disclosed non-limiting embodiment of the present disclosure can include receiving a query phrase for electronic health records in plain language text; translating the query phrase into a first database query with predefined query generation syntax and a second database query with predefined query generation syntax, the first database query is a subset of the second database query; and determining a relationship between the first database query and the second database query.

A further embodiment of any of the foregoing embodiments of the present disclosure may include, wherein the first database query includes a first multiple of database queries, and the second database query includes a multiple of second database queries.

A further embodiment of any of the foregoing embodiments of the present disclosure may include, further comprising providing detailed traceability of the relationship.

A further embodiment of any of the foregoing embodiments of the present disclosure may include, wherein the traceability of each result is provided in near real time.

A further embodiment of any of the foregoing embodiments of the present disclosure may include, wherein the traceability includes indication of a numerator and a denominator.

A further embodiment of any of the foregoing embodiments of the present disclosure may include, wherein the denominator is positive if a predefined test was performed within a predetermined time period.

A further embodiment of any of the foregoing embodiments of the present disclosure may include, wherein the numerator is positive if the predefined test meets a predetermined outcome.

A method of generating a risk score, the method according to one disclosed non-limiting embodiment of the present disclosure can include collecting data from electronic health records; mapping the data to at least one condition category to generate at least one mapped conditioned category; refining the at least one mapped conditioned category into a hierarchy to generate a hierarchal mapped conditioned category; and determining a risk score for a person in response to the hierarchal mapped conditioned category.

A further embodiment of any of the foregoing embodiments of the present disclosure may include, wherein the collecting data includes the collection of at least one of lab results, prescription drug information, vitals, and diagnosis codes from immediate opportunity sources.

A further embodiment of any of the foregoing embodiments of the present disclosure may include, wherein the collecting data includes the collection of data from sources that are closed gaps that represent a condition for which there is documentation of an encounter.

A further embodiment of any of the foregoing embodiments of the present disclosure may include wherein the collecting data includes the collection of at least one of diagnosis codes, lab values, clinical measurements, clinical outcomes, medications and prescription data from non-immediate opportunity sources.

A further embodiment of any of the foregoing embodiments of the present disclosure may include, wherein the collecting data includes the collection of data from sources that are open gaps that represent a condition for which there is no documentation of an encounter.

A further embodiment of any of the foregoing embodiments of the present disclosure may include, further comprising refining the condition category by coefficients.

A further embodiment of any of the foregoing embodiments of the present disclosure may include, wherein the coefficients include a demographic coefficient A further embodiment of any of the foregoing embodiments of the present disclosure may include, wherein the mapped data is stored at a person level so that a user can view details at this level of granularity.

A further embodiment of any of the foregoing embodiments of the present disclosure may include, wherein refining the at least one mapped conditioned category into the hierarchy includes using the highest-certainty source in the hierarchy in response to a person having an hierarchical condition categories condition documented in multiple sources in the data.

A further embodiment of any of the foregoing embodiments of the present disclosure may include, wherein refining the at least one mapped conditioned category into the hierarchy includes excluding conditions that are lower in the hierarchy in response to a person having a multiple of conditions within an hierarchical condition categories hierarchy.

A further embodiment of any of the foregoing embodiments of the present disclosure may include, wherein determining the risk score includes summing all model-specific non-excluded coefficients to determine the raw risk score from the hierarchal mapped conditioned category.

A further embodiment of any of the foregoing embodiments of the present disclosure may include, wherein determining the risk score includes determining a total risk score is a quantitative representation of risk relative to an overall population.

A further embodiment of any of the foregoing embodiments of the present disclosure may include, wherein determining the total risk score includes utilizing all the coefficients from all sources.

A further embodiment of any of the foregoing embodiments of the present disclosure may include, wherein determining the risk score includes determining a closed gap risk score, the closed gap risk score includes only coefficients from sources that represent documented events during the service period.

A further embodiment of any of the foregoing embodiments of the present disclosure may include, wherein determining the risk score includes determining an open gap risk score, the open gap risk score includes only coefficients from diagnosis codes of non-immediate opportunity sources.

A further embodiment of any of the foregoing embodiments of the present disclosure may include, wherein determining the risk score includes determining a blended risk score, the blended risk score is a function of at least one model risk score, the model risk score includes an assignment of coefficients.

A further embodiment of any of the foregoing embodiments of the present disclosure may include, wherein determining the risk score includes calculating the risk score on a regular basis.

A further embodiment of any of the foregoing embodiments of the present disclosure may include, wherein determining the risk score includes calculating the risk score on a regular basis for each person based on the available clinical data for each person.

A method of generating a risk score, the method according to one disclosed non-limiting embodiment of the present disclosure can include collecting data from electronic health records; mapping the data to at least one condition category to generate at least one mapped conditioned category; refining the at least one mapped conditioned category into a hierarchy to generate a hierarchal mapped conditioned category; and determining a risk score for an person in response to the hierarchal mapped conditioned category on a regular basis for each person based on the available clinical data for each person.

A further embodiment of any of the foregoing embodiments of the present disclosure may include, wherein determining the risk score includes determining a closed gap risk score, the closed gap risk score includes only coefficients from sources that represent documented events during the service period.

A further embodiment of any of the foregoing embodiments of the present disclosure may include, wherein determining the risk score includes determining an open gap risk score, the open gap risk score includes only coefficients from diagnosis codes of non-immediate opportunity sources.

A further embodiment of any of the foregoing embodiments of the present disclosure may include, wherein determining the risk score includes determining an open gap risk score, the open gap risk score includes an inference of potential diagnoses.

A further embodiment of any of the foregoing embodiments of the present disclosure may include, wherein an interactive visualization presents the risk report data in a user-friendly and clickable mechanism.

A further embodiment of any of the foregoing embodiments of the present disclosure may include, wherein aggregate counts of open and closed gaps are presented.

A further embodiment of any of the foregoing embodiments of the present disclosure may include, wherein an aggregate counts of potential dollar revenue represented by closure of listed gaps is presented.

A further embodiment of any of the foregoing embodiments of the present disclosure may include, wherein counts of gaps are presented ordered by category and recovery opportunity.

A further embodiment of any of the foregoing embodiments of the present disclosure may include, wherein individual recovery opportunities can be toggled on and off by clicking on the visual, in order to highlight specific opportunity groupings.

A further embodiment of any of the foregoing embodiments of the present disclosure may include, wherein the user can select or click on any single category to refine all displayed gaps by that category.

A further embodiment of any of the foregoing embodiments of the present disclosure may include, wherein all persons with identified gaps are displayed visually.

A further embodiment of any of the foregoing embodiments of the present disclosure may include, wherein persons are color-coded according to opportunity groups currently being displayed.

A further embodiment of any of the foregoing embodiments of the present disclosure may include, wherein persons are organized by associated provider.

A further embodiment of any of the foregoing embodiments of the present disclosure may include, wherein persons are sorted in descending order by count or value of opportunities identified.

A further embodiment of any of the foregoing embodiments of the present disclosure may include, wherein the user can select or click any displayed person, revealing a list of all identified gaps for that person.

A further embodiment of any of the foregoing embodiments of the present disclosure may include, wherein person and provider information and aggregate counts of gaps and gap value are displayed.

A further embodiment of any of the foregoing embodiments of the present disclosure may include, wherein a list of all identified gaps are shown, in order of opportunity group and gap value represented, potentially with color-coding and other visual signifiers.

A further embodiment of any of the foregoing embodiments of the present disclosure may include, wherein the user can select or click any displayed gap, revealing a report of all evidence of that gap.

A further embodiment of any of the foregoing embodiments of the present disclosure may include, wherein the user can select or click some displayed evidentiary references to reveal a display of the original data source for the evidence.

A further embodiment of any of the foregoing embodiments of the present disclosure may include, wherein the report can be output to a file or other raw format for viewing in other programs.

A method of interpreting data from electronic health records, the method according to one disclosed non-limiting embodiment of the present disclosure can include receiving data from a multiple of different EHR implementations; and assigning a status to the data to generate a common format status variable for the data.

A further embodiment of any of the foregoing embodiments of the present disclosure may include, wherein the common format status variable includes a multiple of values for the data.

A further embodiment of any of the foregoing embodiments of the present disclosure may include, wherein the multiple of values include three values.

A further embodiment of any of the foregoing embodiments of the present disclosure may include, wherein assigning the status to the data includes pattern matching the data with an entry in a set of mapping data.

A further embodiment of any of the foregoing embodiments of the present disclosure may include, wherein assigning the status to the data includes pattern matching the data with an entry in a national code set.

A further embodiment of any of the foregoing embodiments of the present disclosure may include, wherein assigning the status to the data includes natural language processing of the data.

A further embodiment of any of the foregoing embodiments of the present disclosure may include, wherein assigning the common format status variable to the data includes assigning a status related to a patient record template.

A further embodiment of any of the foregoing embodiments of the present disclosure may include, wherein the common format status variable includes a multiple of values for the data.

A further embodiment of any of the foregoing embodiments of the present disclosure may include, wherein the multiple of values for each patient record template include a value extracted from the patient record template.

A further embodiment of any of the foregoing embodiments of the present disclosure may include, wherein the patient record template includes at least one of a questionnaire assessment, an order to the patient, and a note related to the patient status.

A further embodiment of any of the foregoing embodiments of the present disclosure may include, wherein assigning the common format status variable to the data includes assigning a status related to immunizations.

A further embodiment of any of the foregoing embodiments of the present disclosure may include, further comprising presenting the common format status variable for verification.

A further embodiment of any of the foregoing embodiments of the present disclosure may include, further comprising returning the common format status variable to a data manipulation module subsequent to verification.

An electronic health record data mining system according to one disclosed non-limiting embodiment of the present disclosure can include a data manipulation module operable to receive data from a multiple of electronic health records and assign a status to the data to generate a common format status variable in a data warehouse and a mapping library operable to receive unassigned data from the data manipulation module and pattern match the unassigned data with an entry in a set of mapping data to generate updated data that is returned to the data manipulation module for assignment.

A further embodiment of any of the foregoing embodiments of the present disclosure may include, further comprising presenting the status assignment for verification prior to return of the updated data to the data manipulation module.

A further embodiment of any of the foregoing embodiments of the present disclosure may include, wherein the mapping library tracks a multiple of patient record templates.

A further embodiment of any of the foregoing embodiments of the present disclosure may include, wherein the mapping library provides a comparison between a multiple of patient record templates and another integrated source.

A further embodiment of any of the foregoing embodiments of the present disclosure may include, further comprising an access configuration module in communication with the data manipulation module to deliver instructions to the mapping library.

A method of health care provider assessment according to one disclosed non-limiting embodiment of the present disclosure can include processing audit log data to create standardized format audit log data; categorizing the standardized format audit log data to define a plurality of events; associating each of the plurality of events with a visit with a patient; and processing data from each visit with the patient; and conveying a visual representation of each visit from the data.

A further embodiment of any of the embodiments of the present disclosure may include, wherein the audit log data includes at least that required by the Health Insurance Portability and Accountability Act (HIPPA).

A further embodiment of any of the embodiments of the present disclosure may include, wherein the audit log data includes an entry for each time an electronic heal record system is accessed.

A further embodiment of any of the embodiments of the present disclosure may include, wherein the entry includes data associated with at least one of a user, a patient, a date, a time, an electronic heal record module accessed, an activity, and scheduling data.

A further embodiment of any of the embodiments of the present disclosure may include, wherein the audit log data is processed by a data receipt module to create the standardized format audit log data.

A further embodiment of any of the embodiments of the present disclosure may include, wherein the data receipt module converts the received audit log data in its various formats into a single common format for all audit log records.

A further embodiment of any of the embodiments of the present disclosure may include, wherein the audit log data is processed by a data receipt module to create the standardized format audit log data.

A further embodiment of any of the embodiments of the present disclosure may include, wherein processing data from each of the visits to determine the efficiency of the health care provider is performed by a data manipulation module.

A further embodiment of any of the embodiments of the present disclosure may include, wherein determining the efficiency of the health care provider includes determining a wait time.

A further embodiment of any of the embodiments of the present disclosure may include, wherein determining the efficiency of the health care provider includes determining a length of each visit.

A further embodiment of any of the embodiments of the present disclosure may include, wherein determining the efficiency of the health care provider includes determining when a patient was roomed.

A further embodiment of any of the embodiments of the present disclosure may include, wherein determining the efficiency of the health care provider includes determining who participated in the visit.

A further embodiment of any of the embodiments of the present disclosure may include, wherein who participated in the visit includes distinguishing between staff and a provider.

A further embodiment of any of the embodiments of the present disclosure may include, wherein processing data from each of the visits occurs in near real time.

A further embodiment of any of the embodiments of the present disclosure may include, wherein processing data from each of the visits provides visibility into a change in schedule.

A further embodiment of any of the embodiments of the present disclosure may include, wherein processing data from each of the visits provides visibility into relative workloads.

A further embodiment of any of the embodiments of the present disclosure may include, wherein categorizing the standardized format audit log data to define a plurality of events includes indexing each event entry by patient and ordering the entries by date and time.

A further embodiment of any of the embodiments of the present disclosure may include, wherein events for each patient are processed by determining if there are other events for the patient earlier the same day.

A further embodiment of any of the embodiments of the present disclosure may include, wherein a first event for the patient will result in a creation of a new appointment.

A further embodiment of any of the embodiments of the present disclosure may include evaluating each of the plurality of events to determine if the event is associated with a support staff role.

A further embodiment of any of the embodiments of the present disclosure may include determining of the support staff role is not an administrative role.

A further embodiment of any of the embodiments of the present disclosure may include evaluating each of the plurality of events to determine if the event occurs in a vitals module of the electronic heal record.

A further embodiment of any of the embodiments of the present disclosure may include assigning the event to a patient room time in response to the event occurring in the vitals module.

A further embodiment of any of the embodiments of the present disclosure may include, wherein events for each patient are processed by determining if there are other events for the patient earlier the same day and the duration of time between a previous event's timestamp and a current event's timestamp.

A further embodiment of any of the embodiments of the present disclosure may include, wherein determining the efficiency of the health care provider includes determining a dense charting time.

A further embodiment of any of the embodiments of the present disclosure may include determining a support staff charting ratio that includes the ratio of the dense charting time for support staff resources compared to the dense charting time for provider resources.

A further embodiment of any of the embodiments of the present disclosure may include determining a support staff charting ratio that includes the ratio of the dense charting time for support staff resources compared to the dense charting time for provider resources.

A further embodiment of any of the embodiments of the present disclosure may include, wherein determining the efficiency of the health care provider includes determining a support staff documentation ratio that includes a number of events by support staff resources compared to the number of events by provider resources.

A further embodiment of any of the embodiments of the present disclosure may include, wherein determining the efficiency of the health care provider includes determining a percent charting before patient visit that includes a percentage of all provider events occurring before a patient roomed time.

A further embodiment of any of the embodiments of the present disclosure may include determining the percent charting during each patient visit that includes a percentage of all provider events occurring between the patient roomed time and patient check-out time.

A further embodiment of any of the embodiments of the present disclosure may include, wherein processing data from each visit with the patient includes determining a percent of all provider events occurring after patient check-out.

A further embodiment of any of the embodiments of the present disclosure may include, wherein processing data from each visit with the patient includes determining a duration between a patient check-in and a first interaction with a support staff.

A further embodiment of any of the embodiments of the present disclosure may include, wherein processing data from each visit with the patient includes determining a duration between a patient check-in and a first interaction with a provider.

A further embodiment of any of the embodiments of the present disclosure may include, wherein processing data from each visit with the patient includes determining an amount of computer time for each visit.

A further embodiment of any of the embodiments of the present disclosure may include, wherein processing data from each visit with the patient includes determining an amount of computer time for each visit.

A further embodiment of any of the embodiments of the present disclosure may include, wherein processing data from each visit with the patient includes determining an amount of computer time after close of business hours.

A further embodiment of any of the embodiments of the present disclosure may include, wherein processing data from each visit with the patient includes determining an order with respect to another patient.

A further embodiment of any of the embodiments of the present disclosure may include, wherein processing data from each visit with the patient includes determining a time associated with the visit.

A further embodiment of any of the embodiments of the present disclosure may include, wherein processing data from each visit with the patient includes compliance with a pre-visit planning protocol for the visit.

A further embodiment of any of the embodiments of the present disclosure may include determining an efficiency of a health care provider from the data, the efficiency of the health care provider is output via interactive graphics for a graphical user interface.

A further embodiment of any of the embodiments of the present disclosure may include, wherein the interactive graphics provide for identifying a physician efficiency.

A further embodiment of any of the embodiments of the present disclosure may include, wherein the interactive graphics provide for identifying a documentation efficiency of a physician.

A further embodiment of any of the embodiments of the present disclosure may include, wherein the audit log data is derived from metadata in an electronic health record.

A method of health care provider assessment according to another disclosed non-limiting embodiment of the present disclosure can include processing audit log data to create standardized format audit log data; categorizing the standardized format audit log data to define a plurality of events; associating each of the plurality of events with a visit with a patient; and processing the data to determine approximate real time tracking of each health care resource from each visit.

A further embodiment of any of the embodiments of the present disclosure may include, wherein the audit log data includes at least that required by the Health Insurance Portability and Accountability Act (HIPPA).

A further embodiment of any of the embodiments of the present disclosure may include, wherein the audit log data includes an entry for each time an electronic heal record system is accessed.

A further embodiment of any of the embodiments of the present disclosure may include determining a dense charting time from the data.

A further embodiment of any of the embodiments of the present disclosure may include determining a support staff charting ratio that includes the ratio of the dense charting time for support staff resources compared to the dense charting time for provider resources.

A further embodiment of any of the embodiments of the present disclosure may include determining a support staff charting ratio that includes the ratio of the dense charting time for support staff resources compared to the dense charting time for provider resources.

A further embodiment of any of the embodiments of the present disclosure may include, wherein processing the data to determine each health care resource associated with each visit from the data includes determining an about real time tracking of each resource in relation to a presence with the patient.

A further embodiment of any of the embodiments of the present disclosure may include, wherein processing the data to determine each health care resource associated with each visit from the data includes determining an about real time tracking of each resource in relation to a presence with the patient.

A method of health care provider assessment according to another disclosed non-limiting embodiment of the present disclosure can include processing audit log data to create standardized format audit log data; categorizing the standardized format audit log data to define a plurality of events; associating each of the plurality of events with a visit with a patient; and processing the data to determine approximate real time tracking of each patient from the visits.

A further embodiment of any of the embodiments of the present disclosure may include, wherein the audit log data includes at least that required by the Health Insurance Portability and Accountability Act (HIPPA).

A further embodiment of any of the embodiments of the present disclosure may include, wherein the audit log data includes an entry for each time an electronic heal record system is accessed.

A further embodiment of any of the embodiments of the present disclosure may include determining a dense charting time from the data.

A further embodiment of any of the embodiments of the present disclosure may include determining a support staff charting ratio that includes the ratio of the dense charting time for support staff resources compared to the dense charting time for provider resources.

A further embodiment of any of the embodiments of the present disclosure may include determining a support staff charting ratio that includes the ratio of the dense charting time for support staff resources compared to the dense charting time for provider resources.

A further embodiment of any of the embodiments of the present disclosure may include, wherein processing the data to determine each health care resource associated with each visit from the data includes determining an about real time tracking of each resource in relation to a presence with the patient.

A further embodiment of any of the embodiments of the present disclosure may include, wherein processing the data to determine each health care resource associated with each visit from the data includes determining an about real time tracking of each resource in relation to a presence with the patient.

A graphical user interface for a health care provider assessment according to another disclosed non-limiting embodiment of the present disclosure can include displaying an appointment from check-in to check-out as a span; displaying a scheduled appointment time along the span; displaying a period of dense charting activity by support staff along the span; displaying a period of dense charting activity by provider along the span.

A further embodiment of any of the embodiments of the present disclosure may include, wherein the span is a line.

A further embodiment of any of the embodiments of the present disclosure may include, wherein the period of dense charting activity by support staff is represented as a rectangle.

A further embodiment of any of the embodiments of the present disclosure may include, wherein the period of dense charting activity is representative of a series of inputs by the support staff A further embodiment of any of the embodiments of the present disclosure may include, wherein the period of dense charting activity is representative of a series of events by the support staff A further embodiment of any of the embodiments of the present disclosure may include, wherein the period of dense charting activity is representative of a series of clicks by the support staff A further embodiment of any of the embodiments of the present disclosure may include, wherein the period of dense charting activity by support staff is represented as a multiple of at least partially overlapping rectangles.

A further embodiment of any of the embodiments of the present disclosure may include, wherein the period of dense charting activity by provider is represented as a rectangle.

A further embodiment of any of the embodiments of the present disclosure may include, wherein the period of dense charting activity is representative of a series of inputs by the provider.

A further embodiment of any of the embodiments of the present disclosure may include, wherein the period of dense charting activity is representative of a series of events by the provider.

A further embodiment of any of the embodiments of the present disclosure may include, wherein the period of dense charting activity is representative of a series of clicks by the provider.

A further embodiment of any of the embodiments of the present disclosure may include, wherein the period of dense charting activity by provider is represented as a multiple of at least partially overlapping rectangles.

The present disclosure describes a method of generating a clinically supplemented risk score by an electronic health record system having one or more processors, the method according to one disclosed non-limiting embodiment of the present disclosure can include collecting, via at least one of the one or more processors, data from a plurality of electronic health records of a patient; parsing, via at least one of the one or more processors, the data into defined fields to generate parsed data; comparing, via at least one of the one or more processors, the parsed data to at least one look-up table to generate an inferred diagnostic condition; comparing, via at least one of the one or more processors, the inferred diagnostic condition to a documented diagnostic condition of the patient in the plurality of electronic health records; mapping, via at least one of the one or more processors, the inferred diagnostic condition to at least one condition category to generate at least one mapped inferred diagnostic condition; refining, via at least one of the one or more processors, the at least one mapped inferred diagnostic condition into a hierarchy to generate a hierarchal mapped conditioned category; and determining, via at least one of the one or more processors, a risk score in response to the inferred diagnostic condition for the patient in response to the hierarchal mapped conditioned category, the risk score representing an expected total cost of care for the patient relative to the average per-patient cost of care over an entire population.

A further embodiment of any of the foregoing embodiments of the present disclosure may include identifying a physician associated with determining the documented diagnostic condition.

A further embodiment of any of the foregoing embodiments of the present disclosure may include identifying that the inferred diagnostic condition is associated with a medication.

A further embodiment of any of the foregoing embodiments of the present disclosure may include, wherein the inferred diagnostic condition is determined retroactively.

A further embodiment of any of the foregoing embodiments of the present disclosure may include, wherein the collecting data includes the collection of data from a source that is a closed gap that represents a condition for which there is documentation.

A further embodiment of any of the foregoing embodiments of the present disclosure may include, wherein the closed gap is associated with the documented diagnostic condition.

A further embodiment of any of the foregoing embodiments of the present disclosure may include, wherein the closed gap is associated with a physician that delivered the documented diagnostic condition.

A further embodiment of any of the foregoing embodiments of the present disclosure may include, wherein the parsed data is based on a presence of a diagnosis code.

A further embodiment of any of the foregoing embodiments of the present disclosure may include, wherein comparing the parsed data includes processing text notations to identify phrases that are then mapped to the diagnosis code.

A further embodiment of any of the foregoing embodiments of the present disclosure may include, wherein comparing the parsed data includes identifying a previously un-notated condition.

A further embodiment of any of the foregoing embodiments of the present disclosure may include, wherein the inferred diagnostic condition is inferred from medication records.

A further embodiment of any of the foregoing embodiments of the present disclosure may include, wherein the inferred diagnostic condition is inferred from laboratory results.

A further embodiment of any of the foregoing embodiments of the present disclosure may include, wherein the inferred diagnostic condition is inferred from patient vitals over a time period.

A further embodiment of any of the foregoing embodiments of the present disclosure may include determining the inferred diagnostic condition from a subset of the data; determining the lack of an associated diagnosis code for the inferred diagnostic condition in the plurality of electronic health records of a patient; and identifying the inferred diagnostic condition as a risk.

A further embodiment of any of the foregoing embodiments of the present disclosure may include, wherein the subset of the data is from at least one of medication records, laboratory results and patient vitals over a time period.

The present disclosure describes a method for generating a clinically supplemented risk score, the method according to one disclosed non-limiting embodiment of the present disclosure can include collecting data from a plurality of electronic health records of a patient via an electronic health record system having one or more processors; determining, via at least one of the one or more processors, an inferred diagnostic condition from the plurality of electronic health records; determining, via at least one of the one or more processors, the lack of an associated documented diagnostic condition for the inferred diagnostic condition; identifying, via at least one of the one or more processors, the inferred diagnostic condition as a risk; and determining, via at least one of the one or more processors, a risk score including the inferred diagnostic condition for the patient, the risk score representing an expected total cost of care for the patient relative to the average per-patient cost of care over an entire population.

A further embodiment of any of the foregoing embodiments of the present disclosure may include, wherein the documented diagnostic condition is based on a diagnosis code.

A further embodiment of any of the foregoing embodiments of the present disclosure may include processing text notations to identify phrases that are then mapped to the diagnosis code.

A further embodiment of any of the foregoing embodiments of the present disclosure may include, wherein determining the inferred diagnostic condition is from parsed data.

A further embodiment of any of the foregoing embodiments of the present disclosure may include, wherein the parsed data includes at least one of medication records, laboratory results, and patient vitals over a time period.

The present disclosure describes a method of generating a care gap workflow by an electronic health record system, the method according to one disclosed non-limiting embodiment of the present disclosure can include collecting data from a plurality of electronic health records of a patient of an electronic health record system; determining an inferred diagnostic condition from the plurality of electronic health records; determining the lack of an associated documented diagnostic condition for the inferred diagnostic condition; and generating a chase list indicative of a care gap between the associated documented diagnostic condition and the inferred diagnostic condition.

A further embodiment of any of the foregoing embodiments of the present disclosure may include, wherein the care gap is representative of a lack of service given a patient's condition.

A further embodiment of any of the foregoing embodiments of the present disclosure may include, wherein the care gap is representative of a documentation gap between care delivered and billed.

A further embodiment of any of the foregoing embodiments of the present disclosure may include, wherein the chase list is color coded to indicate a type of opportunity associated with the lack of the associated documented diagnostic condition for the inferred diagnostic condition.

A further embodiment of any of the foregoing embodiments of the present disclosure may include, wherein the chase list is interactive such that selection of a patient in the chase list reveals detailed records of the patient.

A further embodiment of any of the foregoing embodiments of the present disclosure may include, wherein the chase list identifies a physician associated with the documented diagnostic condition.

A further embodiment of any of the foregoing embodiments of the present disclosure may include identifying the inferred diagnostic condition as a risk; and determining a risk score including the inferred diagnostic condition for the patient, the risk score representing an expected total cost of care for the patient relative to the average per-patient cost of care over an entire population.

A further embodiment of any of the foregoing embodiments of the present disclosure may include, wherein the chase list includes the risk score.

A further embodiment of any of the foregoing embodiments of the present disclosure may include, wherein the chase list is displayed as a comparison of a plurality of patients.

A further embodiment of any of the foregoing embodiments of the present disclosure may include, wherein the comparison of the plurality of patients is ordered by at least one of a care gap, an opportunity and a likelihood of recovery.

A further embodiment of any of the foregoing embodiments of the present disclosure may include, wherein the chase list includes a series of circular icons arranged in a row for each patient.

The present disclosure describes a method for generating a care gap workflow by an electronic health record system, the method according to one disclosed non-limiting embodiment of the present disclosure can include collecting data from a plurality of electronic health records of a patient of an electronic health record system; determining an inferred diagnostic condition from the plurality of electronic health records; and generating a chase list indicative of a care gap associated with the inferred diagnostic condition.

A further embodiment of any of the foregoing embodiments of the present disclosure may include determining the lack of an associated documented diagnostic condition for the inferred diagnostic condition, the care gap associated with a difference between a documented diagnostic condition and the inferred diagnostic condition A further embodiment of any of the foregoing embodiments of the present disclosure may include, wherein the chase list is color coded to indicate a type of opportunity associated with the lack of the associated documented diagnostic condition for the inferred diagnostic condition.

A further embodiment of any of the foregoing embodiments of the present disclosure may include, wherein the chase list is displayed as a comparison of a plurality of patients.

A further embodiment of any of the foregoing embodiments of the present disclosure may include, wherein the chase list is interactive such that selection of a patient in the chase list reveals detailed records of the patient.

A further embodiment of any of the foregoing embodiments of the present disclosure may include, wherein the chase list includes a series of circular icons arranged in a row for each patient.

The foregoing features and elements may be combined in various combinations without exclusivity, unless expressly indicated otherwise. These features and elements as well as the operation thereof will become more apparent in light of the following description and the accompanying drawings. It should be understood, however, the following description and drawings are intended to be exemplary in nature and non-limiting.

BRIEF DESCRIPTION OF THE FIGURES

The disclosures and the following detailed description of certain embodiments thereof may be understood by reference to the following figures:

FIG. 2 shows a more detailed system diagram for the data collection module.

FIG. 3 shows a sample allergy template.

FIG. 4 shows a sample user interaction screen.

FIG. 5A shows a sample task list.

FIG. 5B shows a sample scheduling agent.

FIGS. 6D-1 and 6D-2 show a performance comparison table between different baseline sites.

FIGS. 8B-8E show more detailed examples of a visual representation of a single appointment.

FIG. 9A shows an example of a visual representation of EHR access by module and user.

FIG. 11A shows a user administrator screen.

FIG. 11B shows an example of data filtering.

FIGS. 12A-1 and 12A-2 show an example of filtering risk report.

FIG. 12F shows an example of tracking risk markers and contributions to risk score.

FIG. 13C shows an example of a chase list.

FIG. 14 shows an example of a query generation syntax

FIG. 15A shows an example of a query phrase.

FIG. 15B shows the query phrase parsed into different syntax fields.

FIG. 16A shows an example of a complex multi phrase query.

FIG. 16B shows the complex multi phrase query parsed into different syntax fields.

FIG. 17 shows a metric expressed as a ratio of simple query phrases.

FIG. 18 shows the numerator and denominator of the metric parsed into different syntax fields.

FIGS. 22A-22E show an example of a database query.

FIG. 23 shows an example of a table of results from a query.

FIGS. 25-26 show examples demonstrating the ability to view subsets of the query response data by filtering.

FIG. 27 shows an example of underlying patient detail.

DETAILED DESCRIPTION

Figure 1:
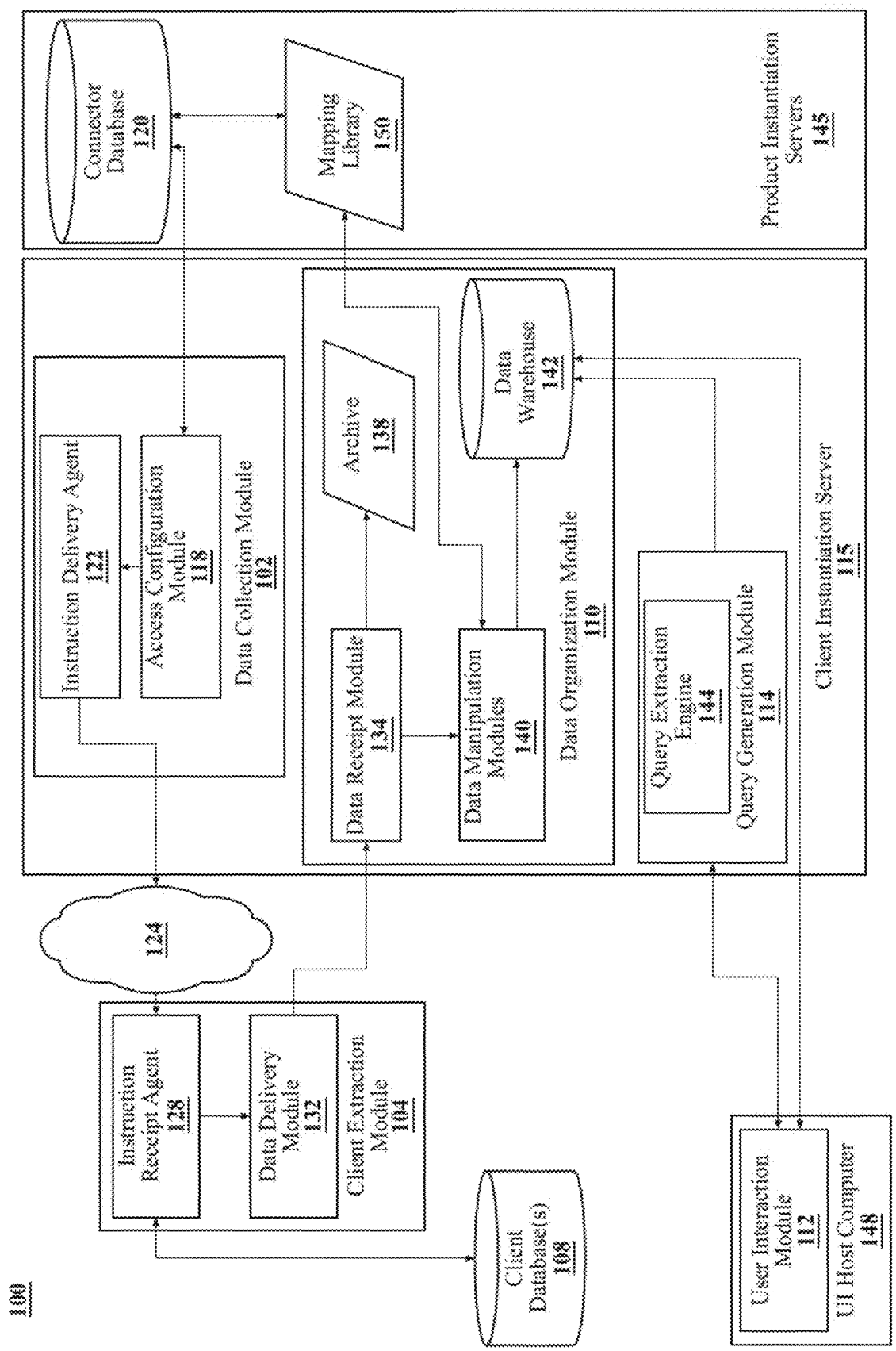
FIG. 1 shows a system diagram for the extraction and organization of health care related data from a plurality of systems.

Referring to FIG. 1, an electronic health record data mining system 100 generally includes a data collection module 102 for specifying data to be collected and optionally initiating data collection, in communication with a client extraction module 104 for extracting specified data from one or more client databases 108. The client extraction module is in communication with a data organization module 110 for processing the extracted data. A user interaction module 112 is in communication with a query generation module 114 for transforming or converting data requests in the form of structured phrases from the user interaction module 112 into a formalized data base query. The data collection module 102, the data organization module 110, and the query generation module 114, may be located on a client instantiation server 115. It should be appreciated that there may be a unique client instantiation server 115 for each client. A connector database 120 and a mapping library 150 may be located on a product instantiation server 145. The product instantiation server 145 may include the mapping library 150 and the connector database 120 which may include data from one or more clients such as mapping data, templates 202 and such.

The data collection module 102 generally includes an access configuration module 118 which facilitates developing requests for specific data to be collected, the connector database 120 which may provide request templates and configuration information for a plurality of vendor and client data systems, and an instruction delivery agent 122 which communicates the requests to the client extraction module 104.

The client extraction module 104 generally includes an instruction receipt agent 128 for receiving and executing data requests. The instruction receipt agent 128 receives a data request from the instruction delivery agent 122 and extracts the requested data from one or more client databases 108. The instruction receipt agent 128 then communicates the extracted data to a data delivery module 132 for communicating the requested data to the data receipt module 134.

The data organization module 110 generally includes a data receipt module 134 for receiving extracted data from the data delivery module 132, an archive 138 for storing data received, one or more data manipulation modules 140 for processing the received data, and a data warehouse 142 for storing the received data and extracted information. The data manipulation modules 140 may be in communication with the mapping library 150 in response to the receipt of unknown data (described later herein).

The query generation module 114 generally includes a query translation engine 144 to facilitate the creation of complex, database-executable data queries based on query phrases that correspond intuitively to the types of measures typically handled by a given client. The query generation module 114, facilitates data retrieval from the data warehouse 142. The query generation module 114 may facilitate system optimization by pre-retrieving common data requests such as most recent blood pressure test, date of last physical, and pre calculating common measures such as categorizing chronic conditions, and storing the results as additional parameters in the data warehouse 142. The query generation module 114 may be adapted to handle a variety of measures, statistics, figures of merit, variables, or the like (collectively referred to herein as "measures" except where context indicates otherwise) that are typically reported by the client extraction module 104 or that otherwise characterize the data collected from a client database 108. Without limitation, a measure may include quantified health care processes and their outcomes.

The user interaction module 112, which may be accessed using a user interaction host computer 148, facilitates retrieval of data and informational reports derived from data stored in the data warehouse 142.

The data collection module 102 facilitates the specification of data to be collected from the client databases 108. Client databases 108 may include one or more of Electronic Health Records (EHR) systems, Enterprise Performance Management (EPM) systems, insurance claims databases, and the like. The client databases 108 may also include various payor data sources (e.g., administrative clams data of insurance providers) as well as clinical data sources (e.g., tracking diagnosis, treatment, and outcomes, among many other things).

The client databases 108 may include one or more installations from one or more vendors with disparate types of data from disparate sources. Such data typically involves use of various brokers, connectors, and other mechanisms to allow the extraction, translation and loading of data as it is moved from database to database. Data sources may be hybrid environments, such as on customer premises, in private/secure clouds, or in public clouds, requiring the use of application programming interfaces (APIs) for different architectures in order to acquire all relevant data for a given client measure or report. Additional customization may occur during each client installation such as variations in naming of encounter types, mapping of patient statuses, location of where primary care physician (PCP) data is stored, database ID, variations in data organization, labeling and parameterization of the data. The resulting data organizational structures may vary between databases at a single client as well as between databases at different clients.

The access configuration module 118 facilitates the specification and collection of desired data across the plurality of systems, vendors etc. The access configuration module 118 may access a plurality of templates 202 stored in the connector database 120 (FIG. 2) on a product instantiation server 145. These templates 202 facilitate mapping the data stored in a client or vendor database to standard system parameters used by the data receipt module 134 and the data warehouse 142. The templates 202 in the connector database 120 facilitate rapid creation and configuration of data collection tools such as database queries.

An allergy template 202A lists data to be collected 304, information about the location of the data in the client database 308, and customization fields 302 (FIG. 3). The templates 202 may include, for example, information such as: parameters to be collected; default locations for parameter data in a plurality of vendor systems; customization fields 302 such as location of database, target data warehouse; frequency or schedule for data collection; and the like.

The access configuration module 118 may include an access configuration user interface module 204 to facilitate the creation of data requests. The access configuration user interface module 204 may include a graphical user interface using standard templates 202. The access configuration user interface module 204 may show, for example, templates or maps of desired parameterized data, data fields on client databases 108 to be mapped to parameterized data, resulting SQL queries to be sent to instruction receipt agent 128, and the like. A screen 400 from the access configuration user interface module 204 facilitates the entry of values 404 for customization fields 302 to create a customized template 502 for a particular client (FIG. 4).

Once the template 202 has been customized, the instruction delivery agent 122 may communicate these requests to the client extraction module 104. A plurality of customized templates 502 are connected into a task list 500 (FIG. 5). Data requests may be made on a scheduled basis, a periodic basis, as a one-time delivery, and the like. A scheduling agent 600 may schedule delivery of data requests in the form of customized templates 502 and task lists 500 by the instruction delivery agent 122 to the client extraction module 104 (FIG. 6).

The instruction delivery agent 122 may send the data request directly to an instruction receipt agent 128 on the client extraction module 104. It should be appreciated that the instructions may be sent through one or more intermediate devices or servers to enhance data security such as by operating as a firewall, a single access point between the client extraction module 104 and the data collection module 102. These one or more intermediate devices may reside in one or more locations such as in a cloud 124, on third party servers, and the like. The instruction delivery agent 122 may use an API to interact with a cloud architecture for data access, such as the commercially available Informatica™ cloud architecture. The cloud architecture may contact the instruction delivery agent 122 on a schedule, initiating the transmission of a data request by the instruction delivery agent 122.

The client extraction module 104 facilitates extraction of the specified data from the client databases 108 and providing the extracted data to the data organization module 110. The client extraction module 104 may include an instruction receipt agent 128 and a data delivery module 132. This functionality may reside on a single computing device, be distributed across a plurality of computing devices, reside on the cloud, or the like. The instruction receipt agent 128 receives data requests from the instruction delivery agent 122. The instruction receipt agent 128 then extracts the requested data from one or more client databases 108 to be made available to the data delivery module 132. The data extraction may be periodic, scheduled, on demand, and the like. Data extraction may be limited such as extracting recently modified data, data entered within a certain time frame and the like.

The client database 108 may include one or more data storage systems implemented across one or more computing devices. The data extracted from the one or more of the client databases 108 may be sent to the data delivery module 132 for transmission to the data receipt module 134. The data delivery module 132 may process the extracted data prior to transmission using methodologies such as: compression; encryption; restructuring the data to conform to a common schema, facilitating compliance with regulations covering protected health information such as HIPAA; and the like. The data delivery module 132 may deliver the data through a direct connection with the data receipt module 134, over a wireless or Internet connection, and the like. The data may be delivered directly to the data receipt module 134 or through one or more intermediate devices or servers designed to enhance data security by operating as a firewall, a single access point between the client extraction module 104 and the data organization module 110, and the like. These one or more intermediate devices may reside in one or more locations such as in the cloud 124, on third party servers, and the like.

The data organization module 110 processes the extracted data and stores the processed data in a data warehouse 142. The data organization module 110 may include a data receipt module 134 which may perform processing steps such as decompressing and decrypting the data, performing error checking, normalizing the data, and the like. This received data may then be provided to an archive 138 prior to any data processing. Further, the received data may be provided to one or more data manipulation modules 140.

Different data manipulation modules 140 may be directed to different use cases such as practice health assessment, smoking assessment, and others. A data manipulation module 140 for a particular use case may include processing the data received from different sites, various EHR implementations, different EHR manufacturers, a plurality of providers and others into a set of precisely defined data points, statuses, metrics, and such. EHR data may vary in how the data is labeled, the order of data, the meaning of particular data terms, the use of unstructured and pseudo structured written data and notes as opposed to structured selections from a set, and others. A data manipulation module 140 may be operable to interpret the various incoming data and create output data and metrics in a common format.

Figure 6A:
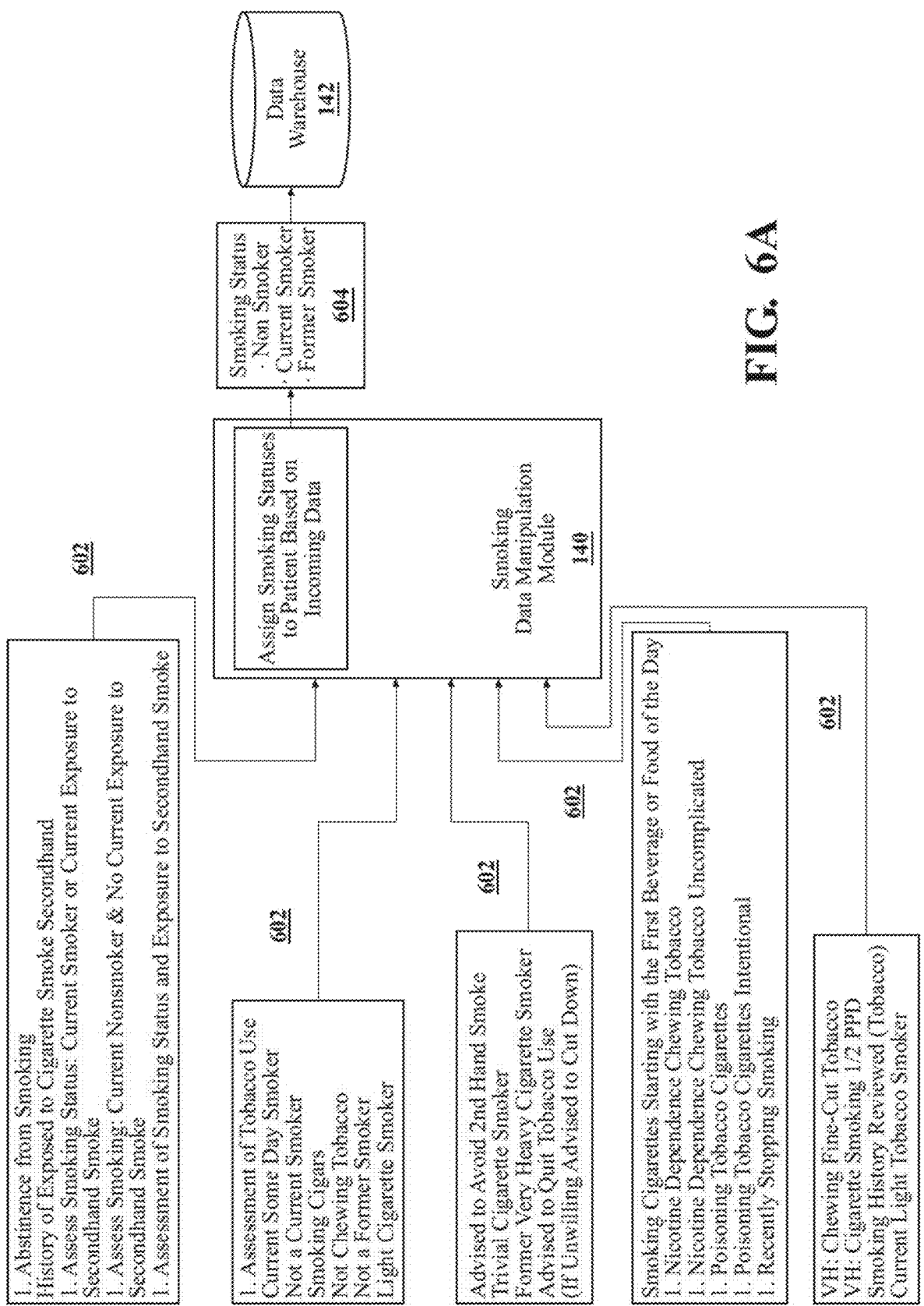
FIG. 6A shows a partial system diagram for a data manipulation module and examples of received data

Referring to FIG. 6A, an illustrative example of incoming data, is that of smoking data 602 from a variety of input sources. The data manipulation module 140 processes the incoming smoking data 602 to output a smoking status variable 604 with defined values. As shown (FIG. 6A) there may be significant variety in the descriptions used in the incoming smoking data 602. The output of the data manipulation module has reduced the variety to a single status variable 604 with three values. This is but an illustrative example and it should be appreciated that incoming data may map to one or more variables having a defined set of values.

Figure 6B:
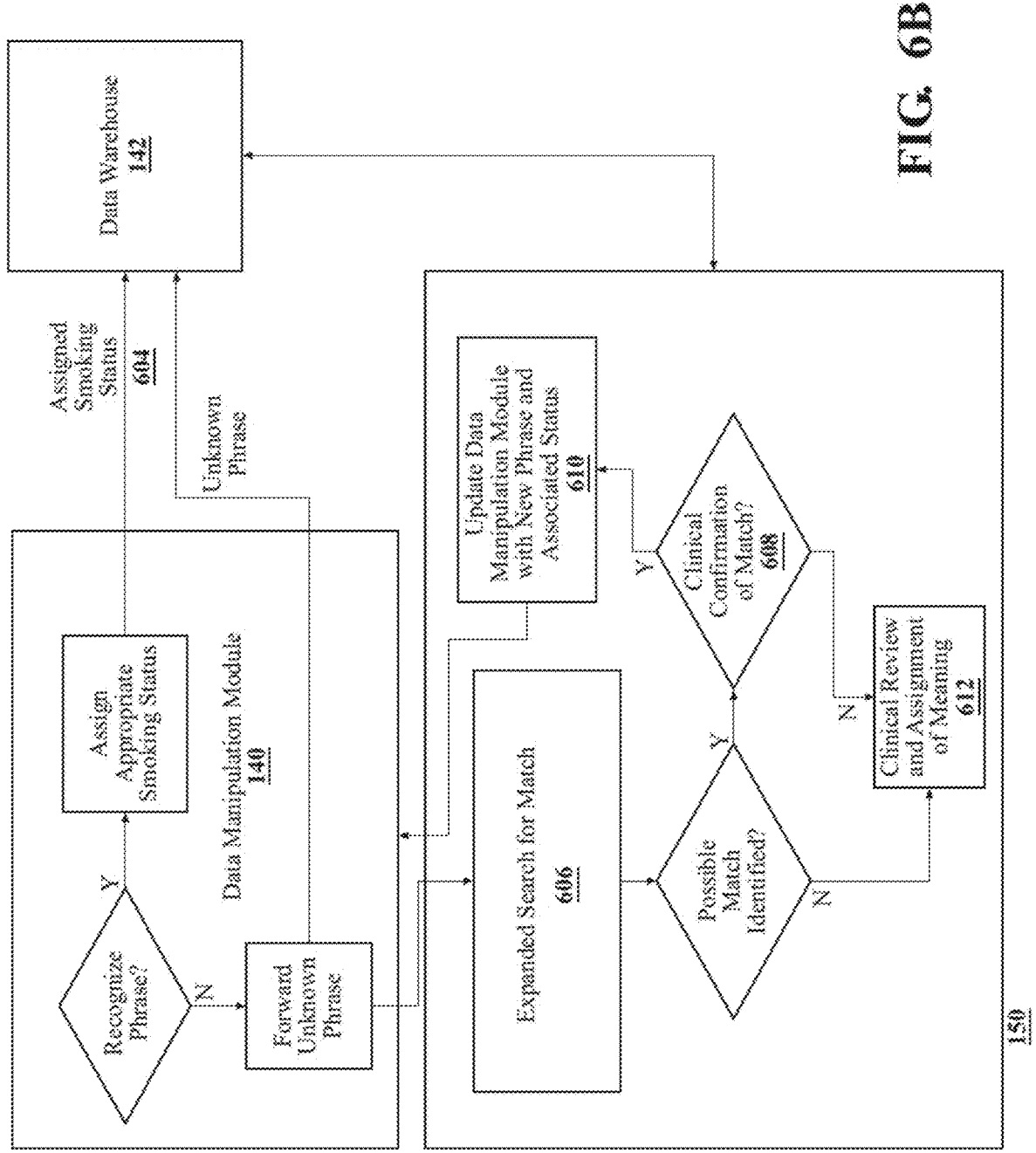
FIG. 6B shows a system diagram for a mapping library.

Referring to FIG. 6B, the data manipulation module 140 may include a set of rules, dictionaries, maps and such to evaluate each incoming smoking datum 602. If the incoming smoking datum 602 conforms to the rules or has a mapping entry, a value is assigned to the smoking status variable 604 and that is sent to the data warehouse 142. If the data manipulation module 140 is unable to successfully map the incoming smoking datum 602 to a specific value for the smoking status variable 604, the incoming smoking datum may be saved to the data warehouse 142 then communicated to the mapping library 150 for further processing. The mapping library 150 may include an expanded search for a match 606 comparing the incoming smoking datum 602 to additional mapping data from other sites and clients, existing national code sets, and others. National code sets used may include: SNOMED (Systematized Nomenclature of Medicine), Common Procedural Terminology (CPT), Healthcare Common Procedure Coding System (HCPCS), National Drug Codes (NDC), US National Library of Medicine RxNorm, Vaccine Administration CVX codes, Logical Observation Identifiers Names and Codes (LOINC), International Classification Disease versions 9 and 10, and others.

Figure 6C:
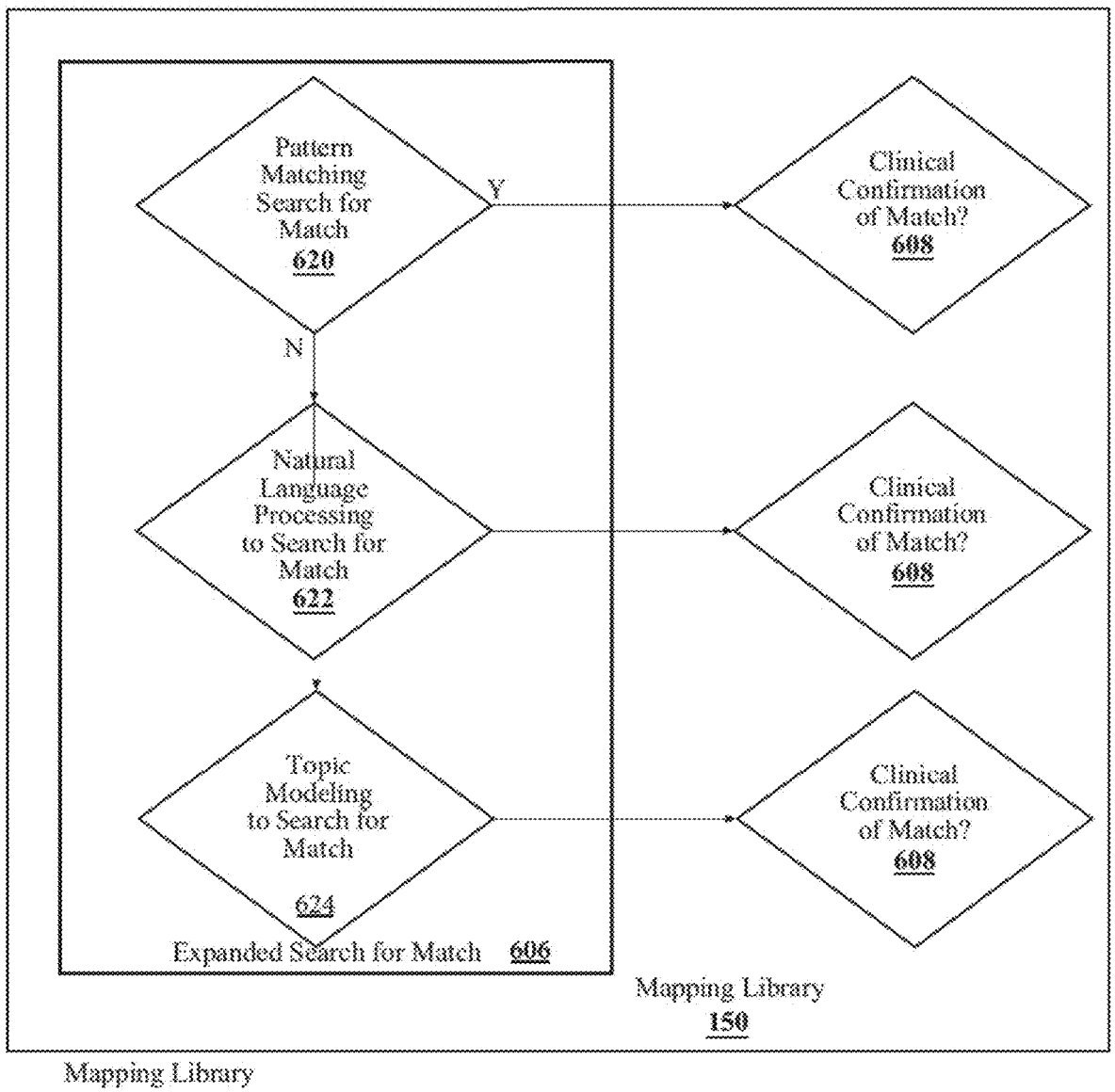
FIG. 6C shows a more detailed system diagram for a mapping library.

Referring to FIG. 6C, an expanded search for a match 606 may include pattern matching 620 the incoming datum 602 with an entry in broader set of mapping data or in the national code sets. The expanded search for a match 606 may include one or more layers of analysis to identify a match of incoming data including one or more techniques such as: directed and stochastic-assisted pattern matching 620; natural language processing 622; and topic modeling 624. Directed and stochastic-assisted pattern matching 620 may attempt to directly match incoming datum 602 with an entry in broader set of pattern mapping data based on previously known patterns identified through experience with other clients and other systems; stochastic-assisted pattern matching which may utilize a library of functions to normalize across misspellings and acronym usage to provide additional accuracy in the pattern matching. Topic modeling 624 may include analysis of inbound terminology to identify trends in subject matter and word usage. This may provide additional patterns which may be used in later processes Once a potential rule or mapping has been identified, it may be presented to a trained clinician for verification of the rule or mapping (step 608). If confirmed, the rule or mapping may then be added to the set used by the data manipulation module 140 that sent the datum 602 to the mapping library 150138 (step 610). Additionally, the previously unprocessed data in the data warehouse 142 are processed. In an illustrative and non-limiting example, on a regular basis, for example daily, the system may automatically identify the presence of unprocessed data and initiate one or more of the data manipulation modules 140 to process the previously unprocessed data.

The accuracy of the data manipulation modules 140 may be evaluated, in part, by comparing the results output from the data manipulation modules 140 with the results generated for comparable baseline sites which have, for example, similar numbers of patients, similar patient demographics, similar source system IT configuration and source organization business lines, and such. One or more of these factors may be considered in the selection of baseline sites for use in the automated reporting.

Figures 2, 6D:
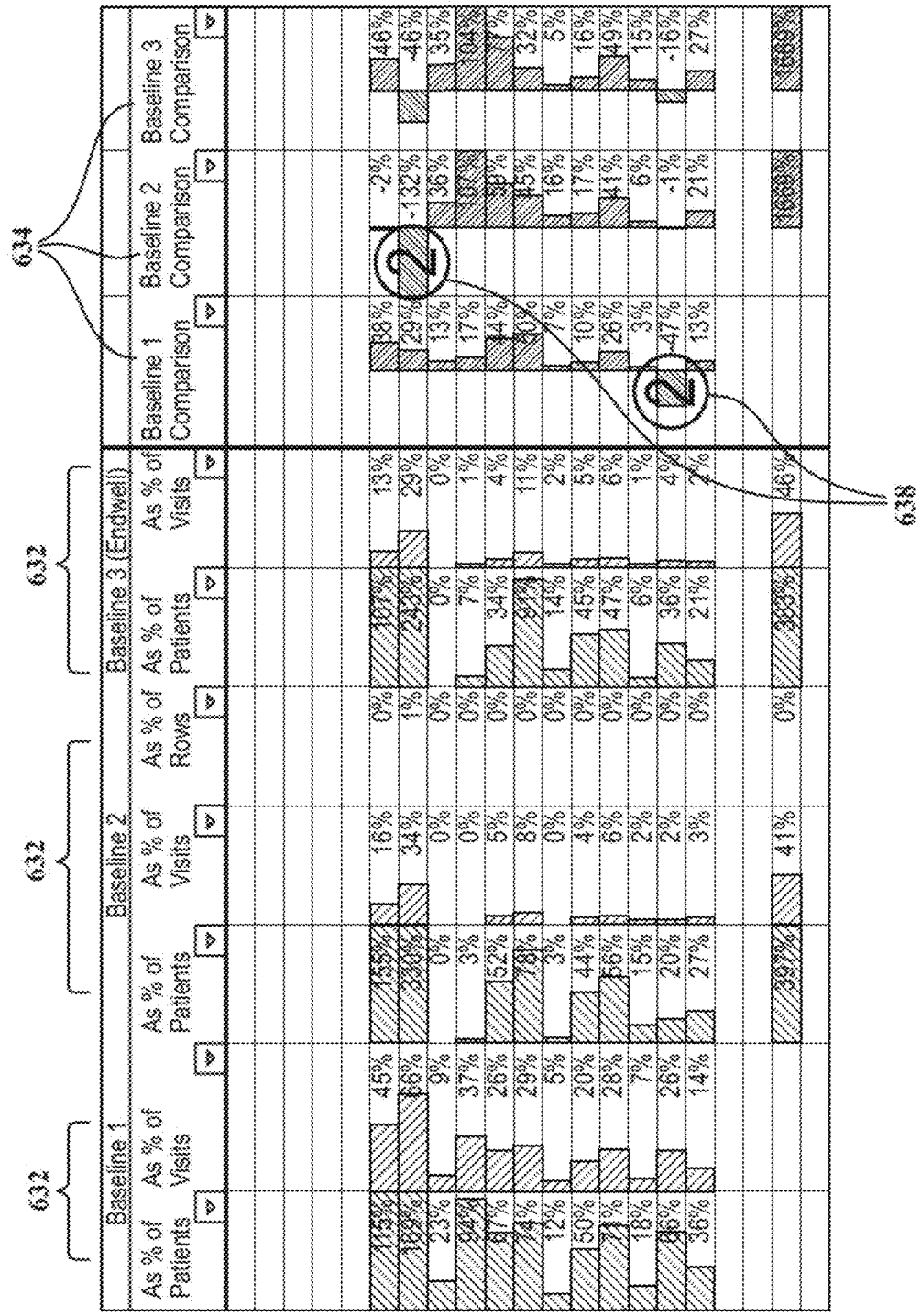

Referring to FIG. 6D, an illustrative summary comparison table 630 is shown displaying information about different immunizations including data on immunizations per patient and per visit basis together with similar data for baseline comparison sites 632. Also included in the summary comparison table 630 is data showing relative performance 634 of the site relative to the baseline comparison sites. When differences in relative performance 634 between the site and one or more baseline comparison sites exceeds a predefined threshold, for example 10%, the efficacy of the associated data manipulation module 140 that processed those data may need to be evaluated. In response to an exceeded threshold, the system may automatically alert an appropriate analyst via e-mail, text and the like. The recipient analyst may then choose to configure the mapping library 150 to use an expanded set of mappings based on criteria similar to that described for the baseline sites above. Alternately, the mapping library 150 may automatically process additional mappings sourced from areas such as the selected baseline sites and all other sites. The expanded mappings may be used on a 'pending' basis to generate a simulated baseline comparison for review by the analyst. Upon approval by the analyst, the mappings may be promulgated by at least one of full incorporation into the data manipulation module 140, inclusion in the mapping library 150, incorporation in the connector database 120, and such.

The data manipulation modules 140 may include one or more modules to provide: data normalization, data cleansing, practice health assessment, and the like. Once the data is processed by the one or more data manipulation modules 140, the resulting data may be stored in a parameterized format in the data warehouse 142.

The data warehouse 142 and the archive 138 may each include data related to a single client, or to a plurality of clients. It should be appreciated that the archive 138 and the data warehouse 142 may be hosted in various locations such as a provider server, a client server, in the cloud, or other locations.

Figure 7A:
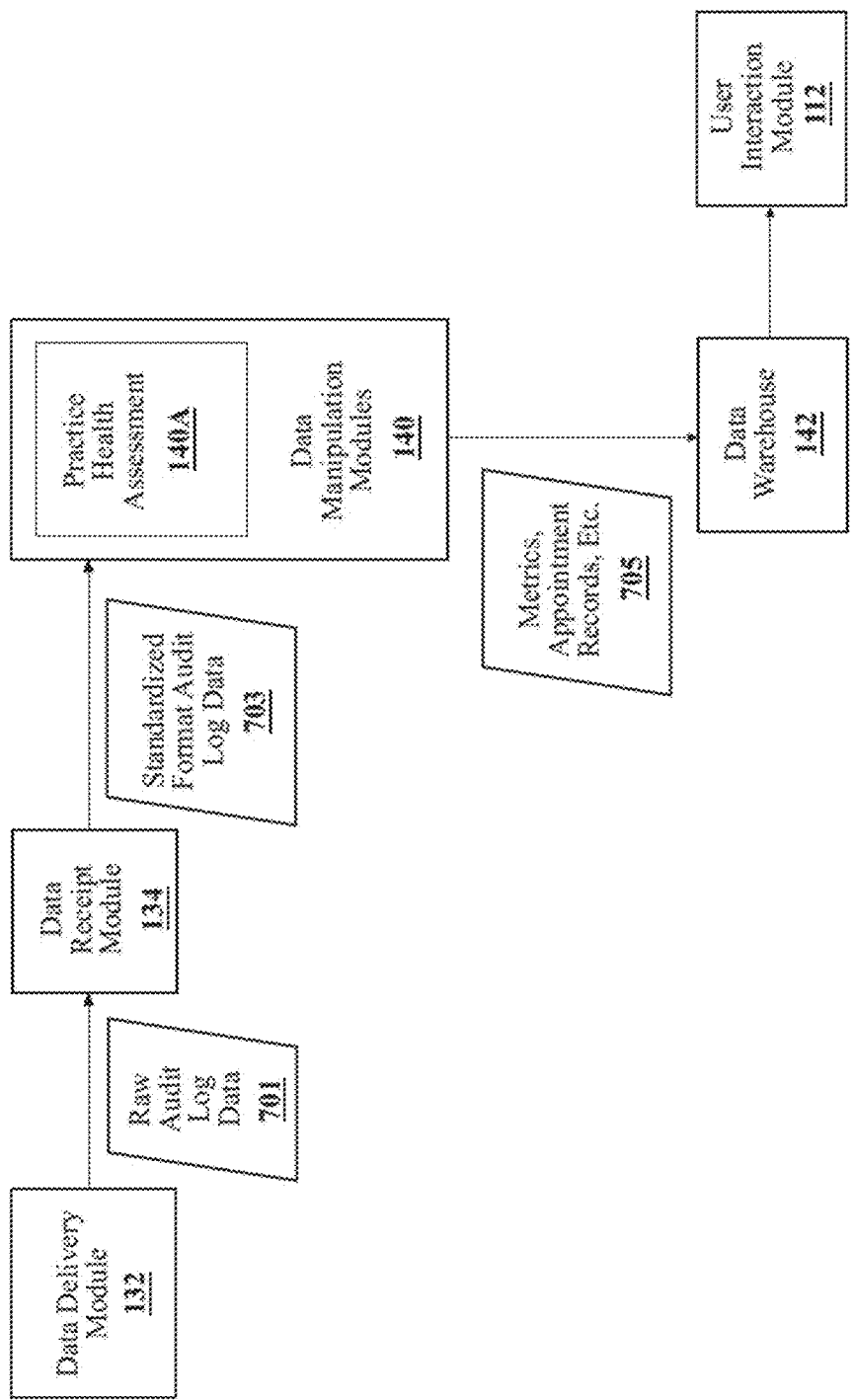
FIG. 7A shows a partial system diagram or interactions with the data delivery module and the data manipulation modules.

With reference to FIG. 7A, an illustrative example of the data delivery module 132 may be utilized to deliver data extracted from audit logs required by the Health Insurance Portability and Accountability Act (HIPPA). The audit logs include an entry for each time an EHR system accessed where each entry may include information such as user, patient, date and time, EHR module accessed, activity, scheduling data, and others. In an illustrative and non-limiting example, an audit log file may be created in the absence of a HIPPA audit log generated by an EHR, by the client extraction module using timestamps associated with other database entries and combining and flattening all metadata tagged to data records in a system into a simulated audit log file.

The audit log data 701 may be processed by the data receipt module 134 to create standardized format audit log records 703. The audit log data 701 as sent may vary significantly in format, terms, types of data included, and others depending on the originating practice, EHR vendor, and other factors. The data receipt module 134 converts the received audit log data in its various formats into a single common format for all audit log records, the standardized format audit log records 703. A data manipulation module 140, such as a practice health assessment module 140A, may then process the standardized format audit log data 703. The practice health assessment module 140A may then process the data from the standardized format audit log data 703 to determine the details of each patient's visit to a practice. Examples of the details which may be determined include, for example, when the patient arrived, when the patient was roomed, when the patient was first seen by the provider, the time spent by the provider with the patient at a particular occurrence, and others. The practice health assessment module 140A may then generate unified appointment records; calculate representative metrics; and others 705.

Figure 7B:
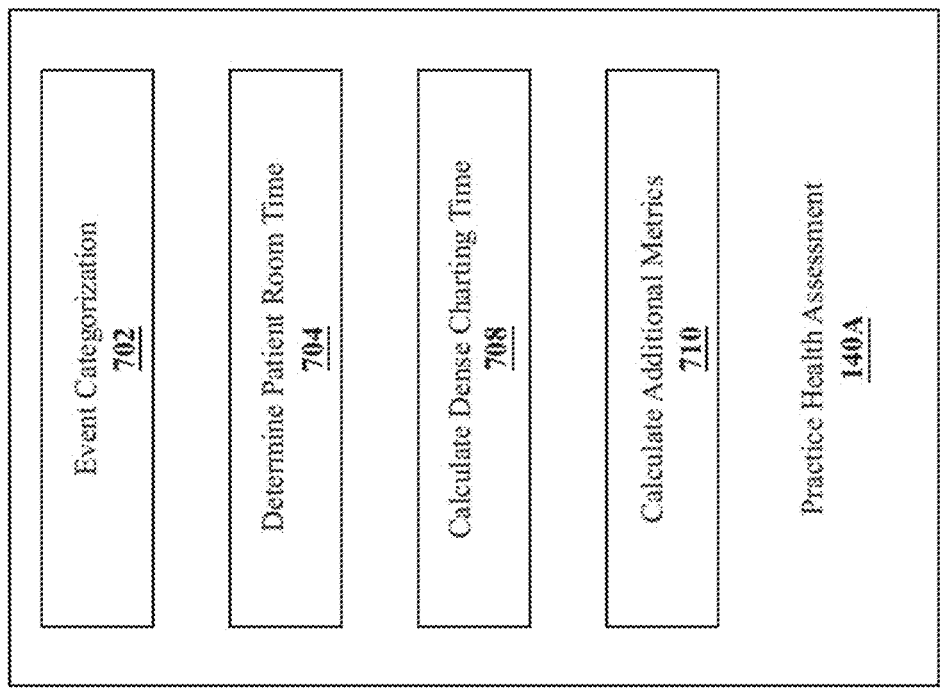
FIG. 7B shows the steps of a practice health assessment module.

With reference to FIG. 7B, the practice health assessment module 140A may begin with categorization of the event (step 702) described elsewhere herein. Once all the entries in the audit log have been associated with individual appointments, data for an individual appointment may be processed to determine when the patient was roomed (step 704). Data for an individual appointment may be further processed to calculate dense charting time (step 708) which is an estimate of active charting time or time spent by a provider or support staff personnel in front of a monitor interacting with the EHR. Data for all the appointments may be processed to calculate a variety of high-level metrics (step 710) described elsewhere herein.

The processing done by the practice health assessment module 140A on the client instantiation server 115 may occur on a periodic basis as a tool for high level review of operations. The processing may occur in near real time to facilitate operations management by providing visibility into schedule slip and relative workloads to help enable the rebalancing of resources, and such. Real-time visibility may alert administrators to increased patient wait time, increased or excessive provider charting effort, decreasing quality of data capture, and the like. Visibility into these situations may help enable near real-time adjustments to operations such as altering staffing ratios, changing patient assignments and the like to smooth staffing and balance provider and support staff workloads.

Figure 7C:
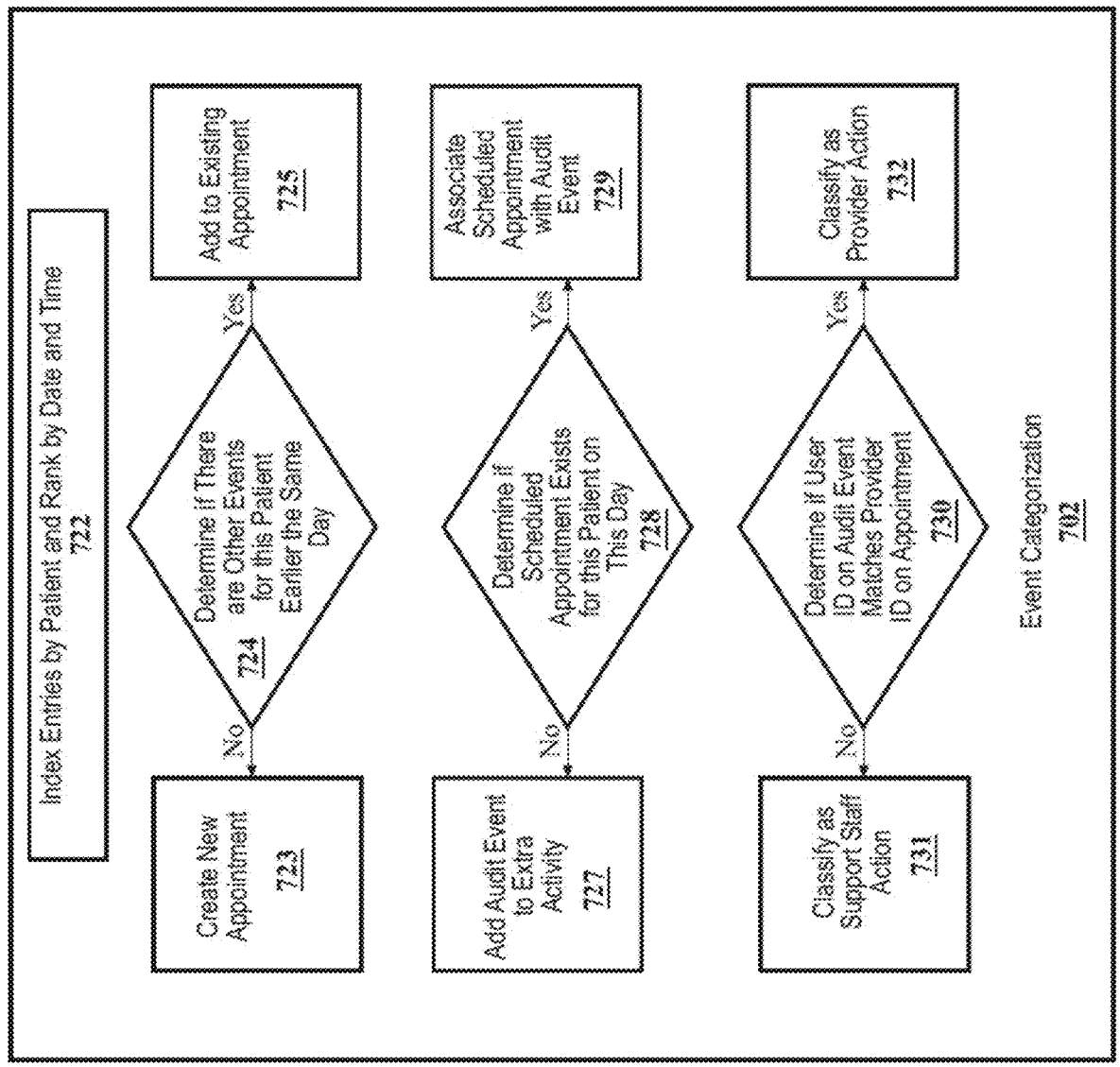
FIG. 7C shows the steps of an event characterization method.

With reference to FIG. 7C, event categorization may begin with indexing each event entry by patient and ordering the entries by date and time (step 722). Once the event entries are indexed by patient, the events for a single patient may be processed beginning with determining if there are other events for the patient earlier the same day (step 724). For example, if this is the first event for the patient the system will create a new appointment (step 723) to associate with the patient, otherwise, the event will be added to the existing appointment (step 725). The schedule for the day will be reviewed to determine if scheduled appointment exists for this patient on this day (step 728). If a schedule appointment exists, it will be associated with the event entry (step 729) otherwise; the event entry will be categorized as extra activity (step 727).

Figure 7D:
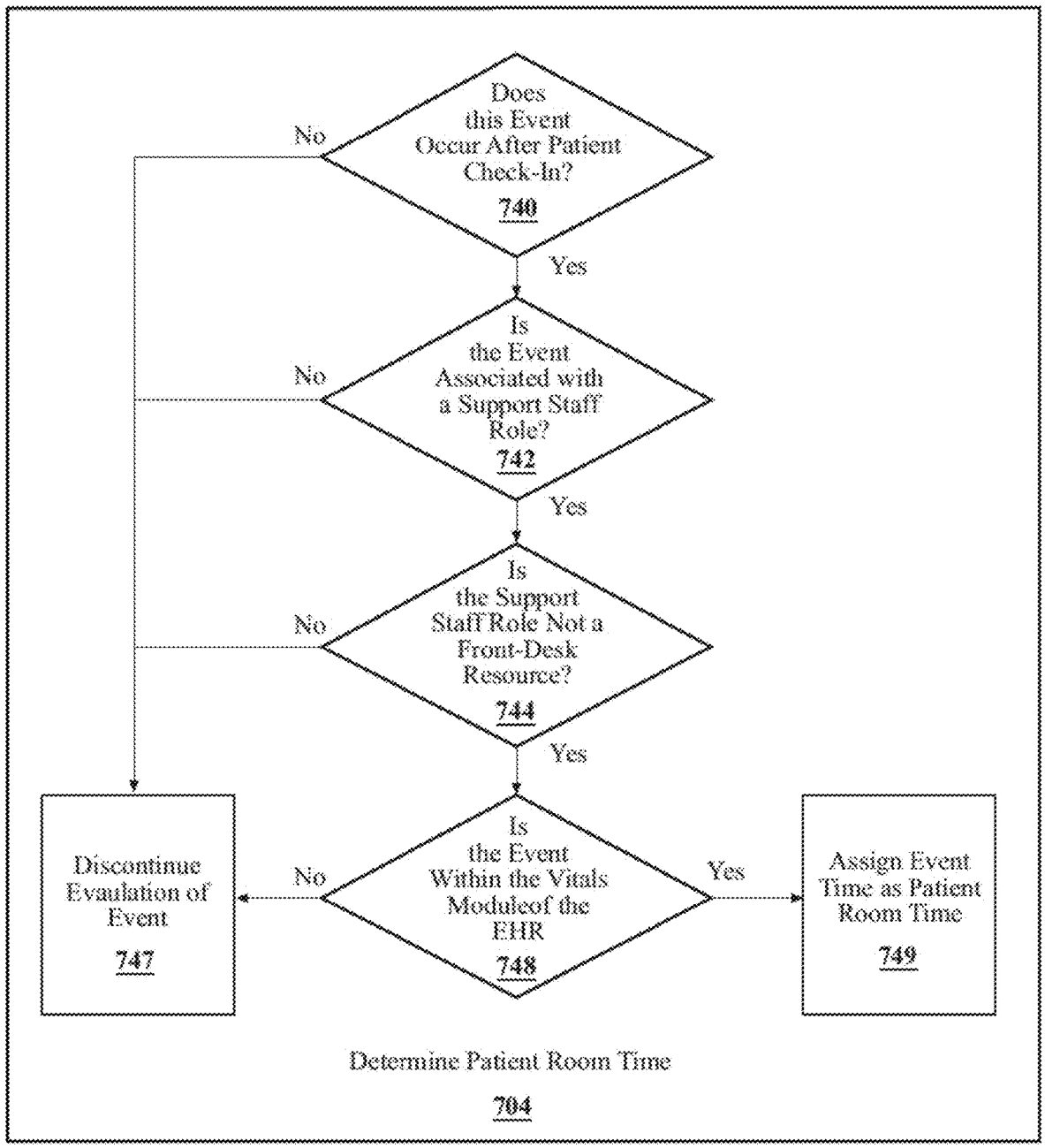
FIG. 7D shows the steps of determining a patient room time.

With reference to FIG. 7D, determining the time a patient was roomed may begin with evaluating an event to determine whether it occurs after patient check-in (step 740). If so, evaluate whether the event is associated with a support staff role (step 742) and if so, whether the support staff role is NOT a front desk role (step 744), that is, not an administrative type role. A negative response in any of the steps discontinues evaluation of that event (step 747). If the event is still under consideration, the event is evaluated to determine whether the event occurs in the vitals module of the EHR (step 748). If the event is in the vitals module, meaning that the patient's vital measurements are being recorded, then that event time will be assigned as the patient room time (step 749).

Figure 7E:
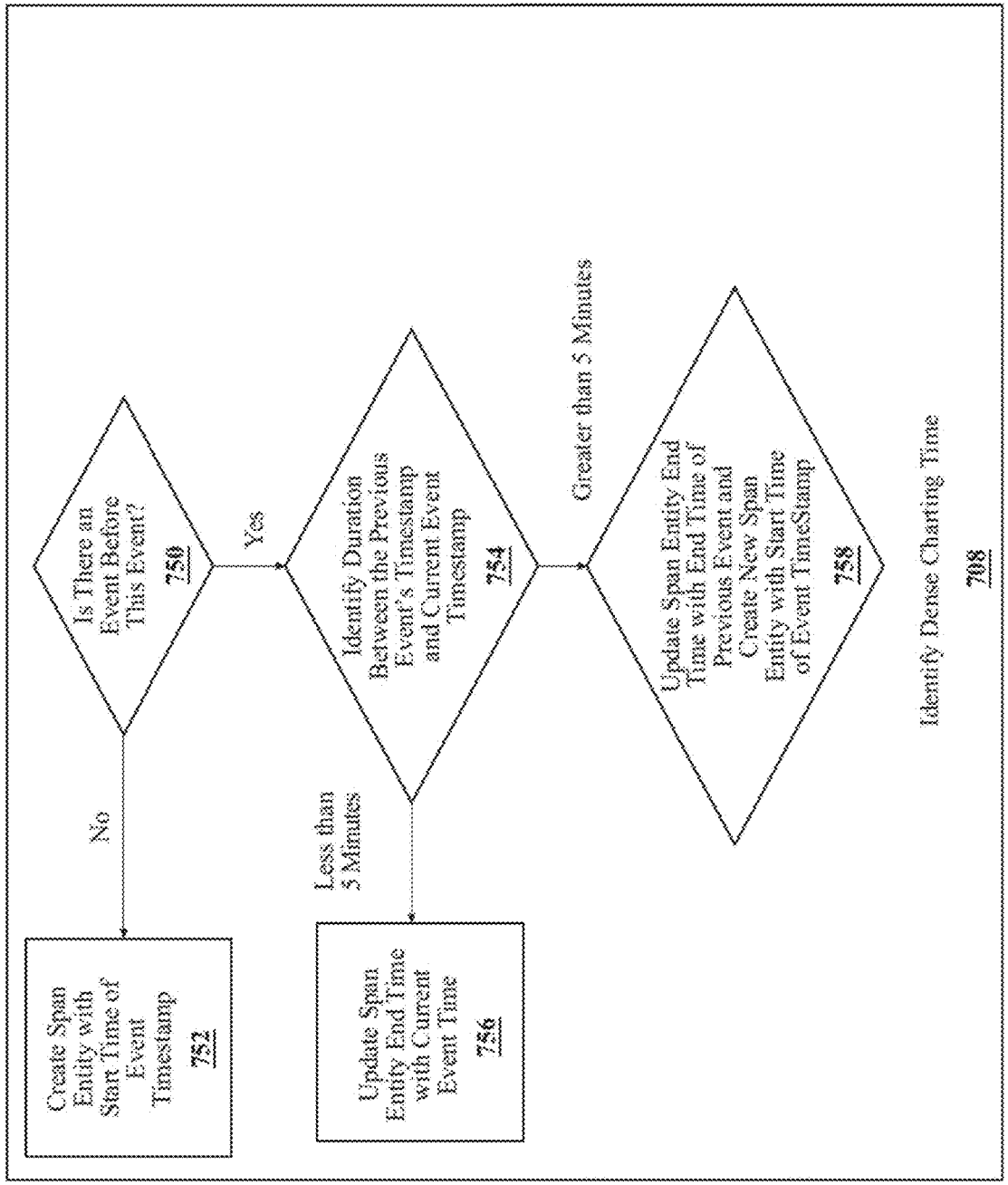
FIG. 7E shows the steps of determining dense charting times.
Figure 8A:
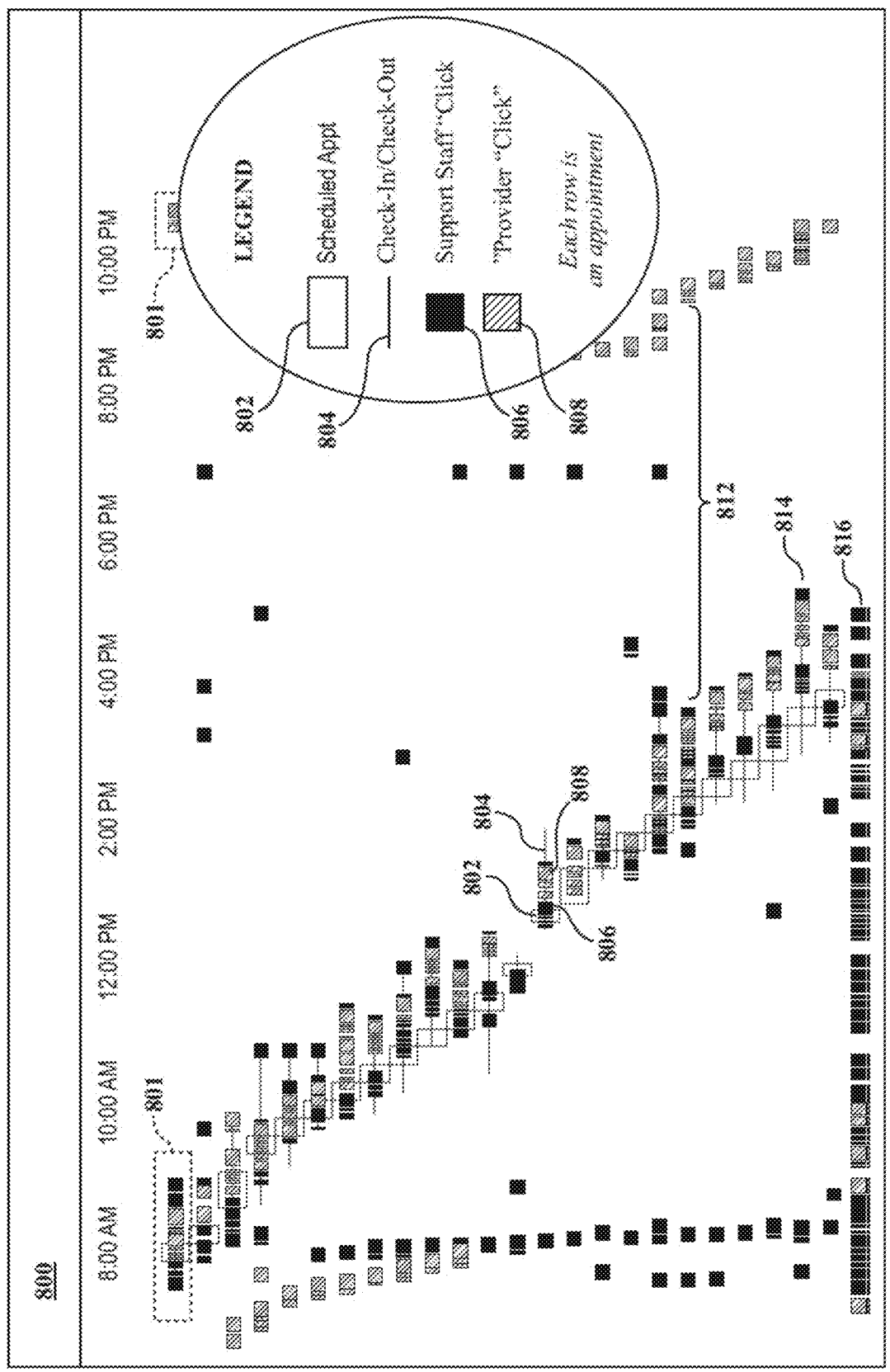
FIG. 8A shows an example of a visual overview representation of appointments.
Figure 8B:
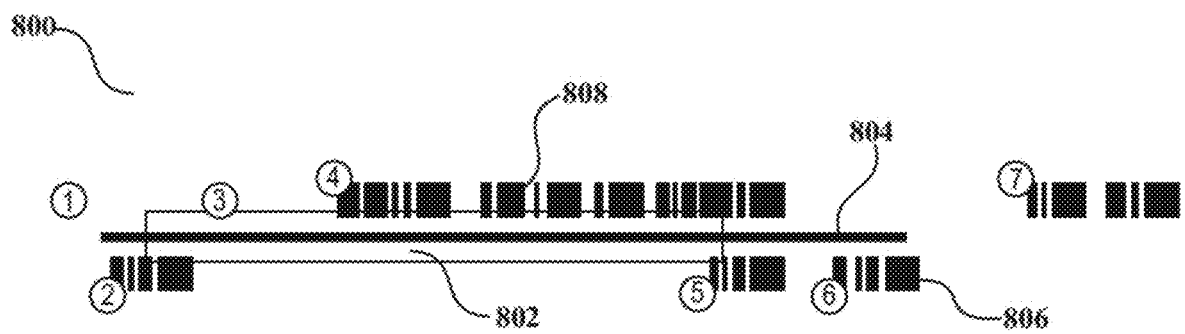
Figure 8C:
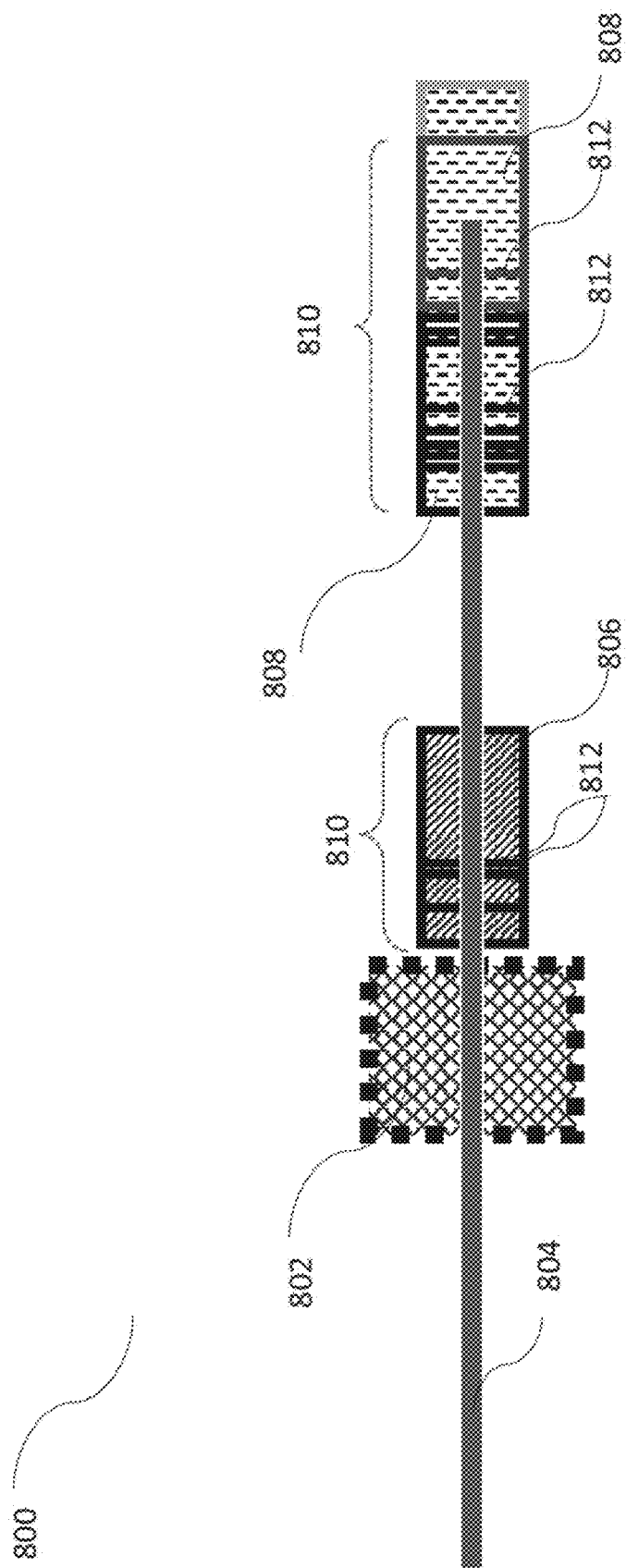

The calculation of dense charting time (FIG. 7E) may be performed separately on events associated with different groups such as support staff, providers, and others. Proceeding through the time ordered events associated with a patient and the group of interest, the process may begin with identifying whether the event is the first event associated with a patient or whether there is a preceding event (step 750). If the event under evaluation is the first event, a span entity is created with a start time and stop time set to the event time (step 752). For subsequent events, the duration of time between the previous event's stop timestamp and current event's start timestamp is calculated (step 754). If the duration between the two events is less than, for example, five minutes, the span entity end time is updated with the current event time stop time (step 756). Otherwise, if the duration of time between events is greater than, for example, five minutes, update the span entity end time with the end time of the previous event and create a new span entity with a start and end time set to the current event time (step 758). Once all the day's events have been processed, the duration between end time and start time for each of the span entities may be calculated and added to a dense charting time metric. This dense charting time may be displayed as overlapping rectangles 814 representing the individual EHR events where the length of the overlapping rectangles grouped in a single span entity 818 (FIG. 8E) represents dense charting time. The individual rectangles 814 may be selected to see the details of a specific EHR interaction.

The "calculate additional metrics" (step 710) may include calculations for the metrics such as: support staff charting ratio (the ratio of the dense charting metric for support staff resources compared to the dense charting metric for provider resources); support staff documentation ratio (number of events by support staff resources compared to the number of events by provider resources); percent charting before patient visit (percentage of all provider events occurring before patient roomed time); percent charting during a patient visit (percentage of all provider events occurring between patient roomed time and patient check-out time); percent charting after (percentage of all provider events occurring after patient check-out); and others.

The metadata in the audit logs such as workstation ID, IP Address, username, and the like may facilitate near real-time tracking of human resources, such as providers and support staff, and help enable location determination such as whether those human resources are in an exam room, at the desk, at home, on the move between visits, and such. This information may facilitate, for example, the identification of insufficient support staff or inefficient support staff allocation among provider departments in near real-time and facilitate the adjusting of staffing ratios.

Additionally, the metadata in the audit logs such as workstation ID, IP Address, username, and the like may facilitate near real-time tracking of patient location as they move throughout the clinic and may include identifying transitions from the waiting room to the exam room to the lab and back to the front desk for check-out, and such.

The processed output of the practice health assessment module 140A may enable the creation of interactive graphics (FIGS. 8A-8G) for a graphical user interface accessed from one or more display devices such as a monitor, a laptop screen, a tablet or other mobile device that is carried by a provider throughout the day, and the like.

The graphical user interface may provide a visual overview representation of one or more appointments 800 in a given time period (FIG. 8A-8E). Each row may represent the interactions associated with a single patient visit 801. Information displayed may include scheduled appointment time 802, actual appointment from check-in to check-out 804, periods of dense charting activity by support staff 806, periods of dense charting activity by provider 808, and others. The periods of dense charting 806 808 may be represented by a series of overlapping rectangles representing individual events 814.

This visualization may facilitate observations such as: delay between patient interaction and completion of patient charts by provider 822; identifying patients who aren't seen until after their scheduled appointments 824; level of activity associated with walk-in clients 826; duration between patient check-in and first interaction with support staff and/or provider; amount of computer time while patient is in the room (to predict patient satisfaction); amount of computer time after close of business hours (to predict provider satisfaction); patients seen before others despite earlier check-in times and/or scheduled appointment start times; compliance with pre-visit planning protocols by identifying chart activity in the early morning before patient check-in; distribution of activity between provider and support staff; appointment slots associated to the longest/shortest wait times; and others.

Figure 8F:
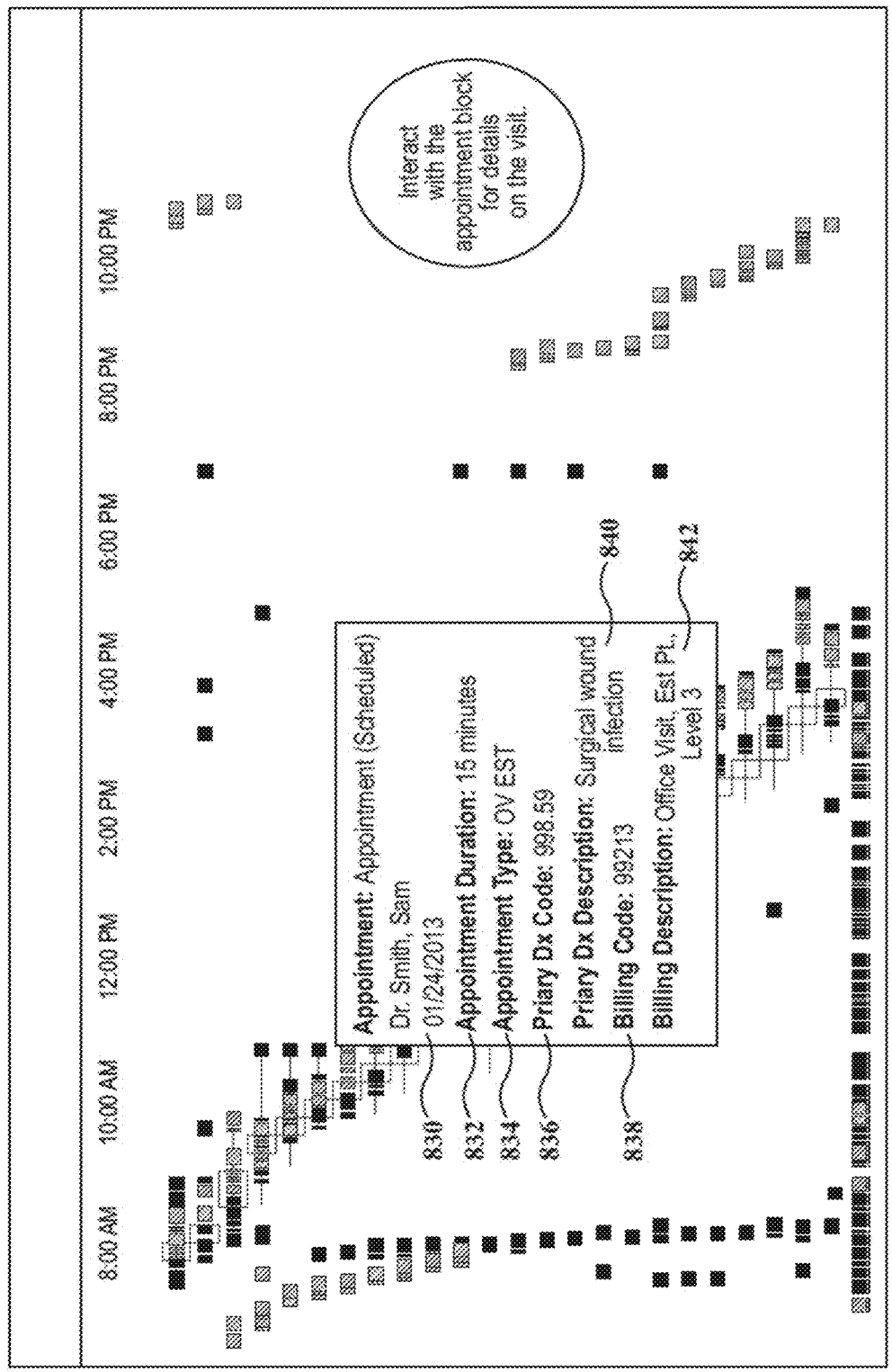
FIG. 8F shows an example of accessing the details of a single appointment.
Figure 8G:
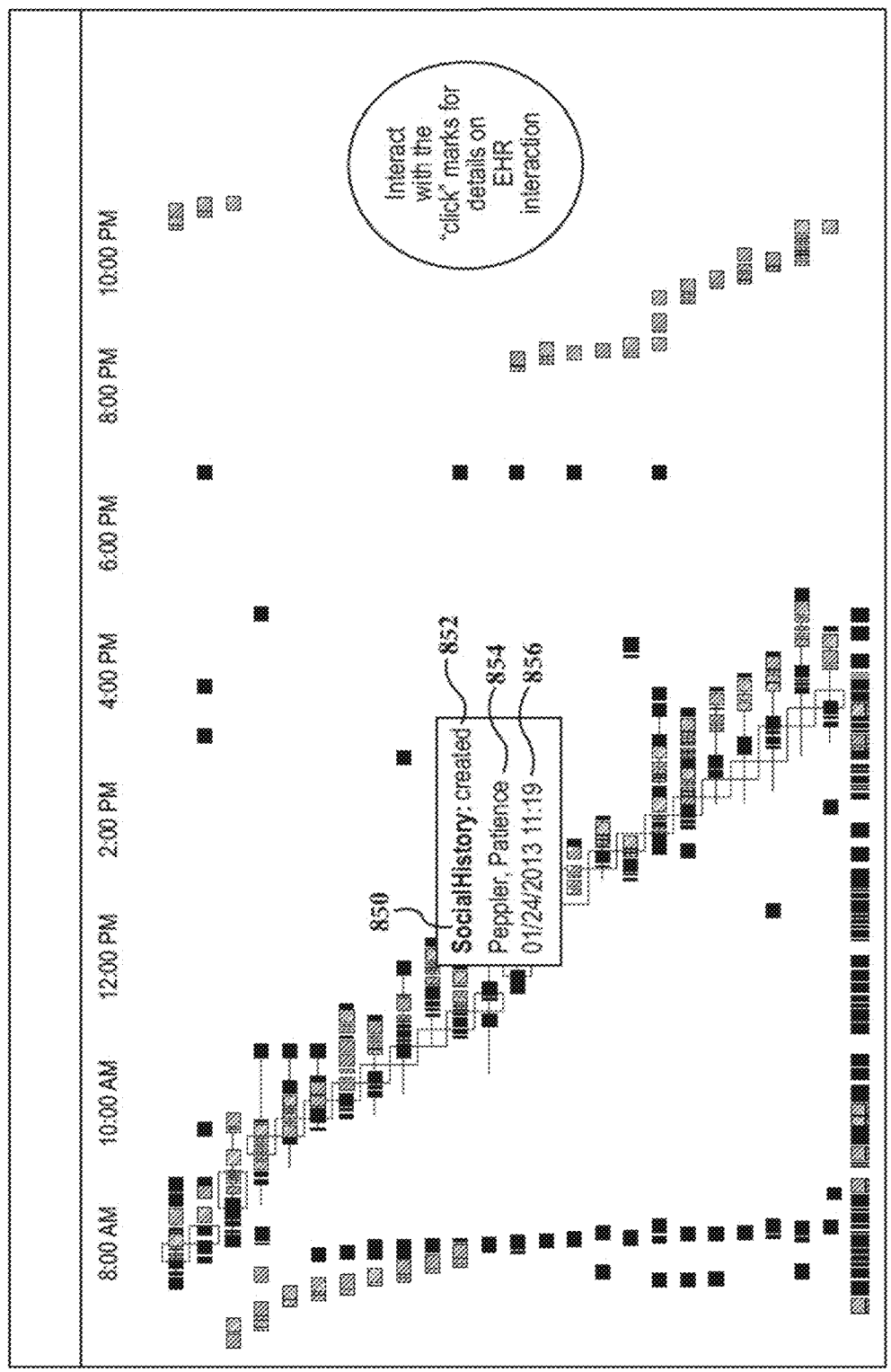
FIG. 8G shows an example of accessing the details of a single event.

The graphical user interface may facilitate interaction with the overview representation of appointments 800 to enable accessing the underlying details on a specific appointment (FIG. 8F). This may enable a user to pull up details on a particular appointment, such as one that has exceeded the time allotted in the schedule, and see information such as, for example, the provider 830, the scheduled appointment duration 832, the type of appointment 834, the primary diagnosis code (DX Code) 836, the primary diagnosis description 840, the billing code 838, the billing description 842, and such. Additionally, detail on a single event (FIG. 8G) may be accessed which may include the module accessed 850, what was done 852, the user 854 and a time and date stamp 856. Analysis of this detailed information may enable an audit of the types of activity that are occupying one or more of the provider and the support staff. Identification of this type of information may lead to changes in workflow. In an illustrative and non-limiting example, this type of audit may indicate that physicians are charting in the order management module at the time that the patient is in the room. This may be an inefficient use of time for the patient and provider and the charting in the order management module may be reassigned to a different member of the support staff to reduce computer time during the patient interaction and improve workflow efficiency.

Figure 9A:
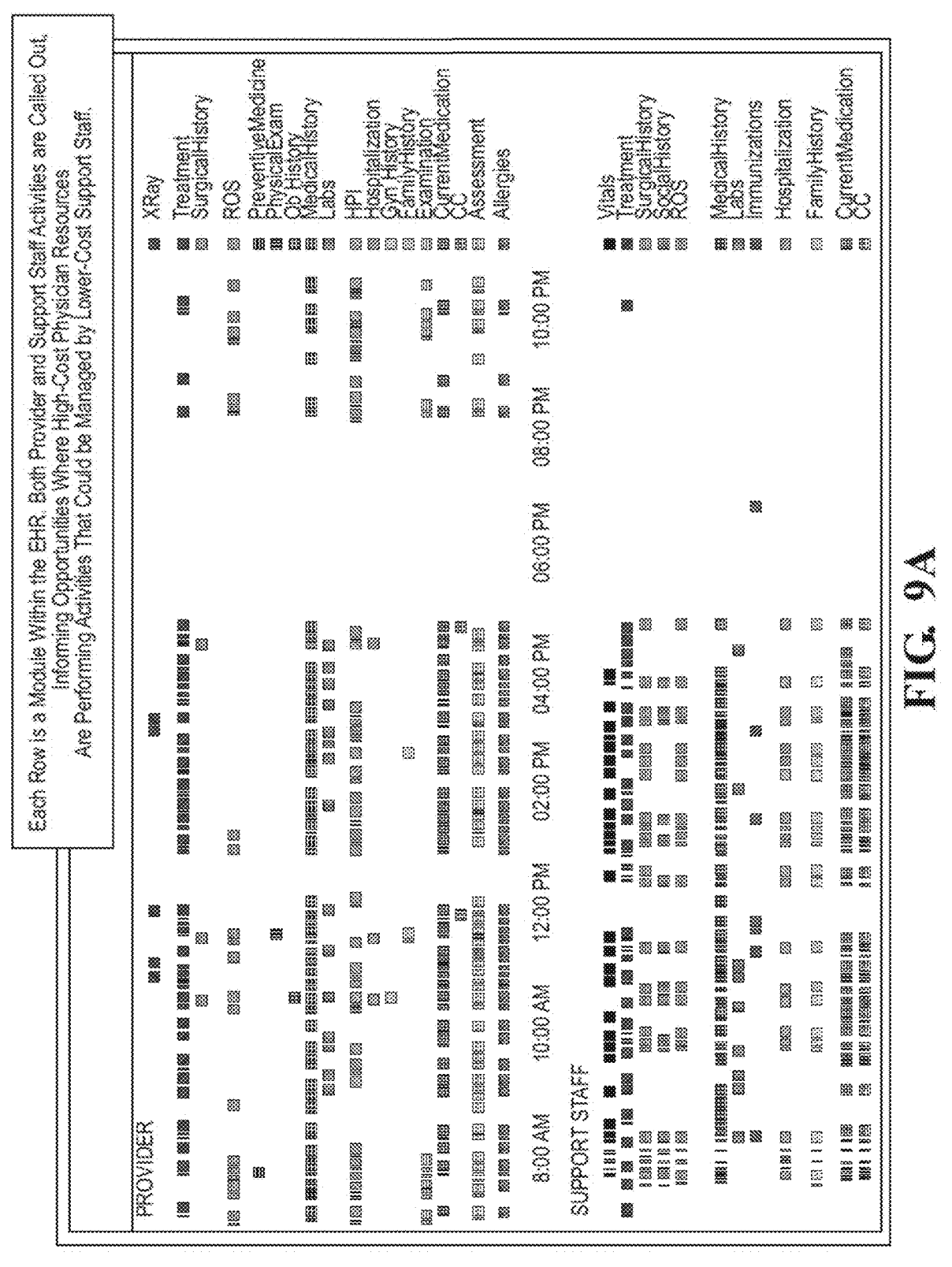
Figure 9B:
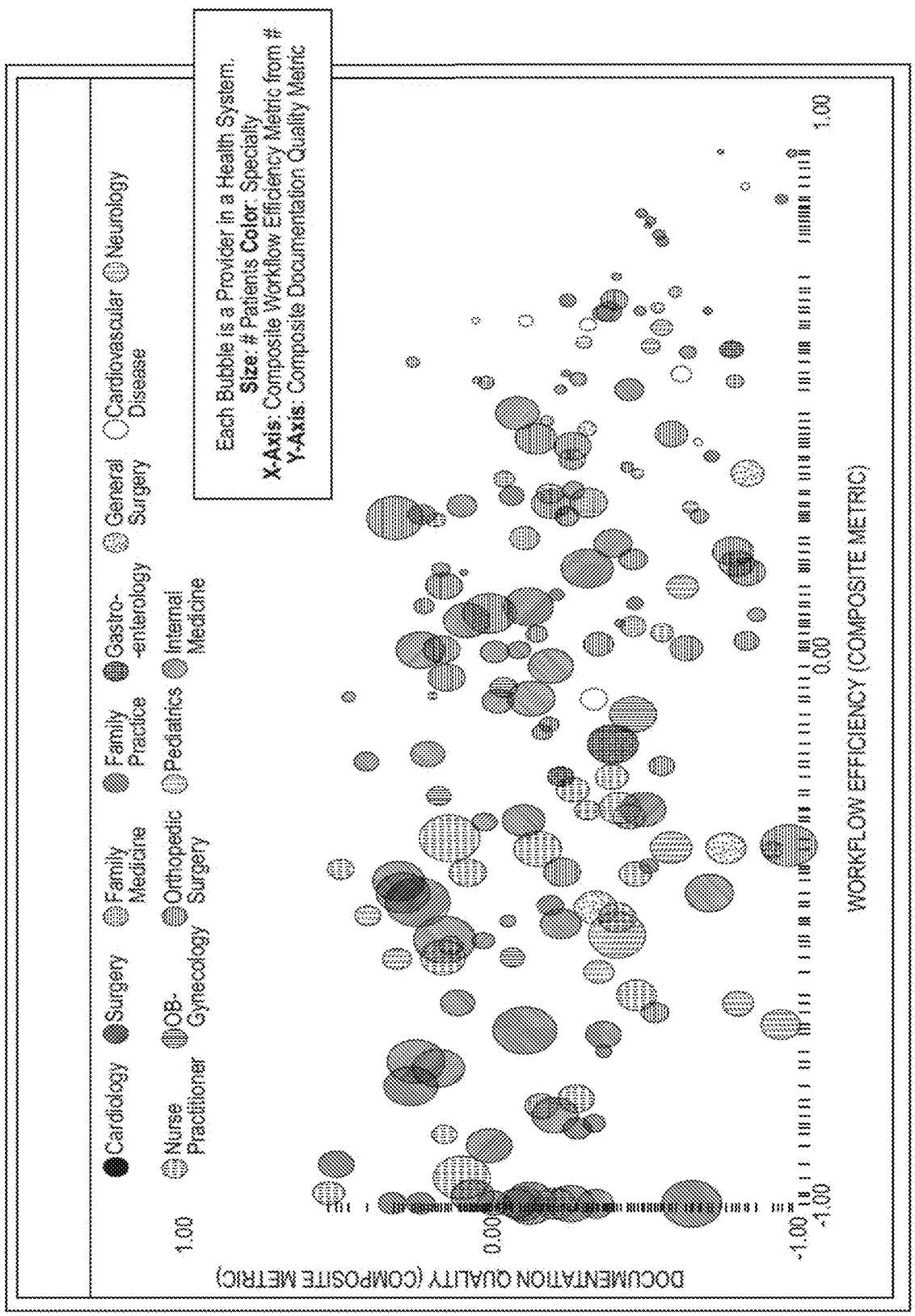
FIG. 9B shows an example of a visual representation of documentation quality vs. workplace efficiency.
Figure 9C:
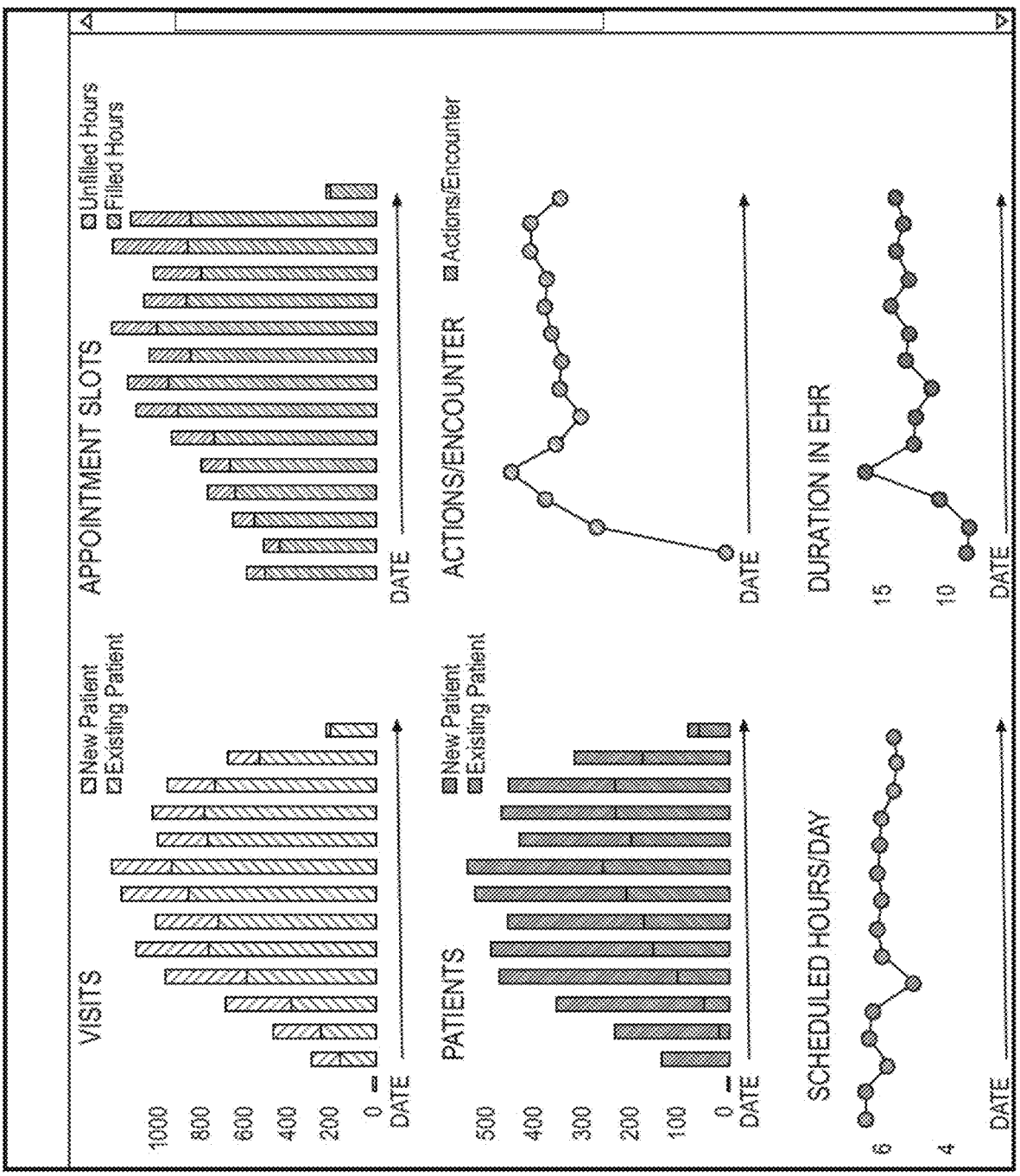
FIG. 9C shows an example of a visual representation of trend data for various metrics.

The processed output of the practice health assessment module 140A may facilitate the creation of interactive graphics (FIGS. 9A-9C) for a graphical user interface that provides additional visual overview representations of a practice. Representations may include a view of the distribution of daily events categorized by EHR module accessed for both supporting staff and providers (FIG. 9A) to facilitate efficiency insights such as whether providers are creating entries in EHR modules better done by supporting staff. In an illustrative and non-limiting example, FIG. 9A shows each "click" in the EHR by provider type, time and EHR module and may help enable a user to compare real workflow distribution against clinical protocols and identify possible discrepancies such as, for example, the provider spending time taking vitals when that should be the responsibility of the support staff With reference to FIG. 9B, another exemplary visual representation depicts an overview of documentation quality versus workflow efficiency. Documentation quality may represent a composite metric based on factors such as physician specialty, the capture of key information as structured data (e.g., vitals), completion of lab orders in a timely fashion, "locking" of an encounter for timely billing, and such. Workflow efficiency may represent a composite metric based on factors such as number of clicks per visit, duration of dense charting per day, and percentage of activity occurring after business hours for different specialties and provider groups, and such. This type of visual representation may facilitate comparisons between groups based on specialty, group size, and others and may enable identification of outliers whose performance is above or below that of their peers. It may be possible to identify a group or physician who is highly efficient but whose documentation is below average 920. Alternately, it may be possible to identify a group or physician with high quality documentation but who is less efficient than their peers 922. It is possible to see that some of the larger practices are internal medicine 924, family practice 926 and OB-gynecology 928. Another exemplary visual representation (FIG. 9C) may include trend data for a variety of metrics such as: distribution of visits each day between new and existing patients; filled and unfilled appointments each day; new and existing patients each day; scheduled hours per day; EHR events for each visit; duration of time in EHR per visit; and others. These trends may be plotted by practice, physician, specialty, and others.

The query generation module 114, together with the query translation engine 144, facilitates retrieval of desired data from the data warehouse 142. The query generation module 114 facilitates optimization of system response time by pre-calculating common measures, categorizing chronic conditions, identifying commonly requested data such most recent blood pressure and the like. The parameterized results are then stored in the data warehouse 142.

The query generation module 114 integrates, as appropriate, newly received patient data into existing patient records on the basis of rules to match patients/members based attributes such as name, date of birth, gender, address, policy numbers, social security numbers, telephone number(s), and other such data to determine the patient data across the multiple different client databases 108. Phonetic algorithms such as a double metaphone algorithms and the like may be used to account for typos/misspellings when matching between different client databases 108. Patient data from one client database may include only data from the practice or network and not include data from specialists and out of network inpatient/emergency visits. Insurance data may not include information such as vitals, lab results, family history, and the like. By integrating the data a much richer patient history is created, facilitating more complex analysis.

The query translation engine 144 allows a user to specify the desired information as relatively simple query phrases, reducing the time required to generate a complex database query from a few days to a few hours. The heretofore specific programming requirements necessary to extract the query are avoided and a user of the system may be one in a field associated with the collected data, familiar with clinical, medical or healthcare system terminology such as a nurse or other health care provider in the example of EHR. That is, the query phrases facilitate operation by users who are skilled in health care operations to craft queries from the data warehouse 142 as desired rather than rely on an intermediate individual skilled in database operations.

Figure 10A:
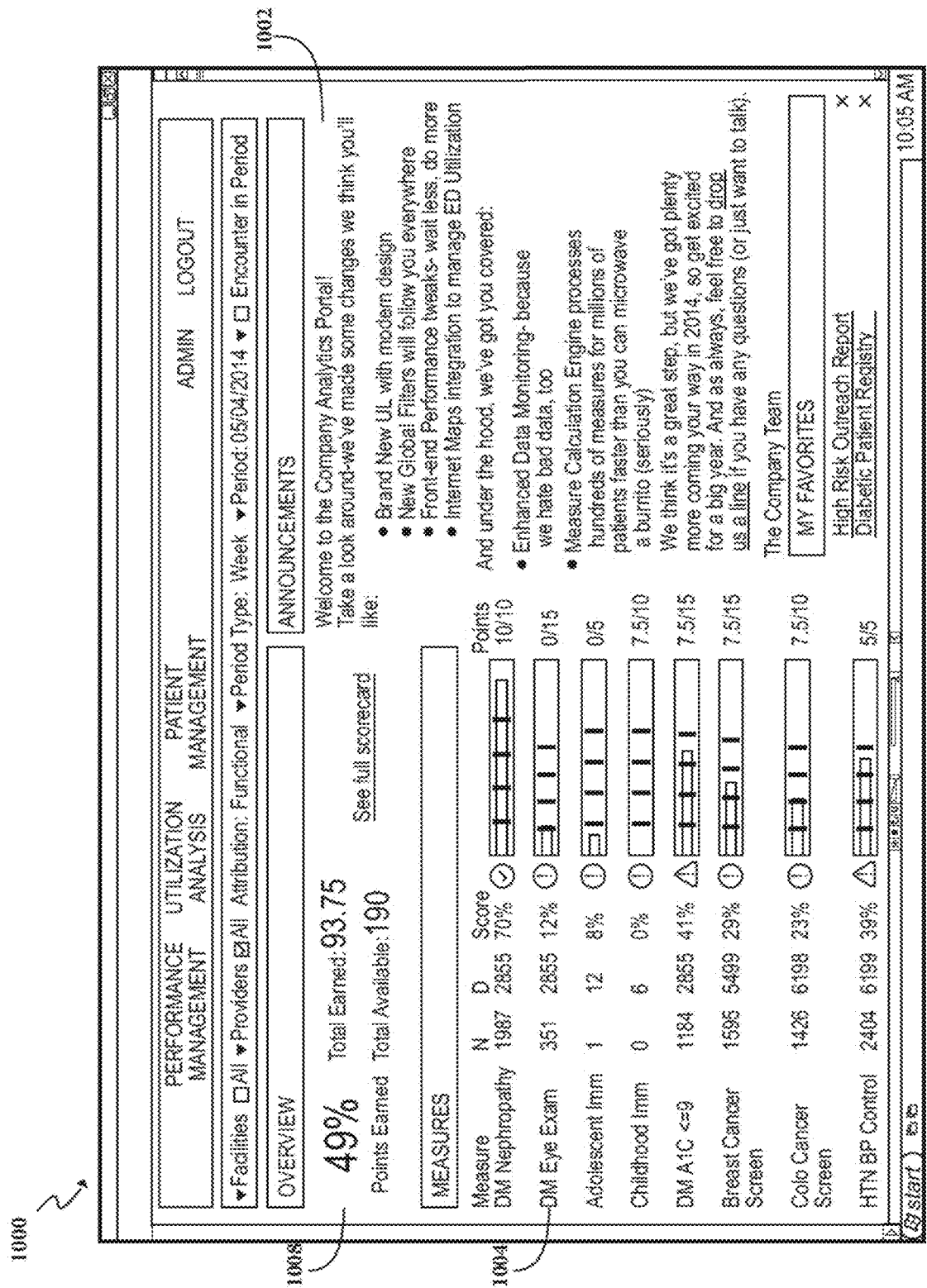
FIG. 10A shows a sample homepage screen.

The user interaction module 112, which may be accessed using a user interaction host computer 148, facilitates retrieval of data and informational reports derived from the contents of the data warehouse 142. The user interaction module 112 may include one or more access screens such as: administrative; home page; initiatives; utilization; patient management; and the like. Each access screen may provide access to various reports generated by queries of the data warehouse 142. The user interaction module 112 may support standard protocols such as Security Assertion Markup Language, SAML, and the like, to facilitate a single, common login with other systems on the client network. The access configuration user interface module 204 may be configurable with respect to the features shown on the various pages presented to a user. In a non-limiting example, a homepage 1000 (FIG. 10A) displays general announcements 1002, organizational initiatives and measures 1004, score cards, aggregate level organizational performance 1008, and/or other aggregate information.

Figure 10B:
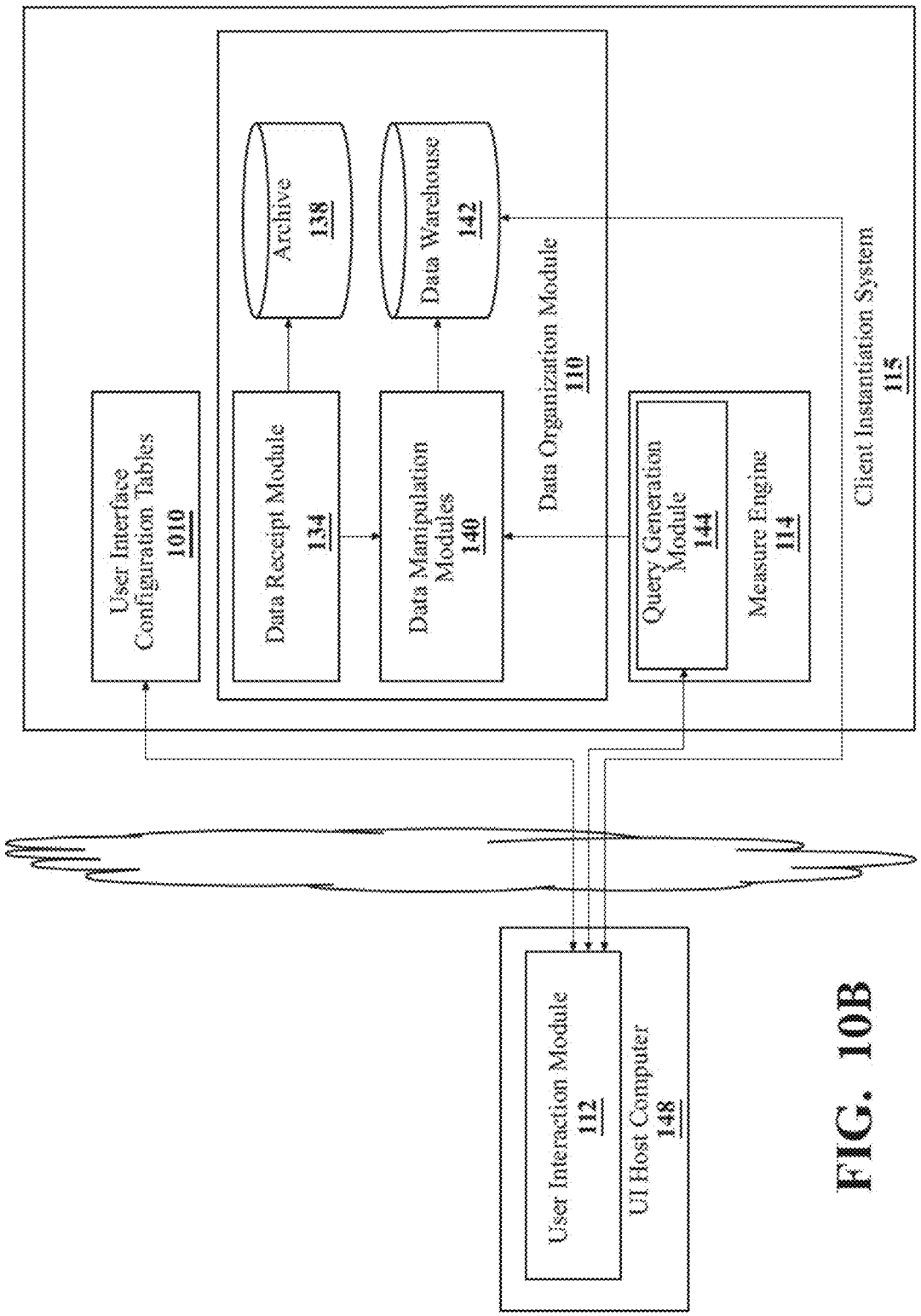
FIG. 10B shows a system diagram of the interactions of the user interaction module with the user interface configuration tables.

The user interaction module 112 may operate inside a web-enabled browser on the user interaction host computer 148. The user interaction host computer 148 may be a mobile device such as a tablet or smart phone and the user interaction module 112 may be built as a native mobile application using IOS or Android. The user interaction module 112 may be customized for individual clients based on parameters in UI configuration tables 1010 (FIG. 10B), to facilitate dynamic page configuration rather than changes to the source code.

Figure 10C:
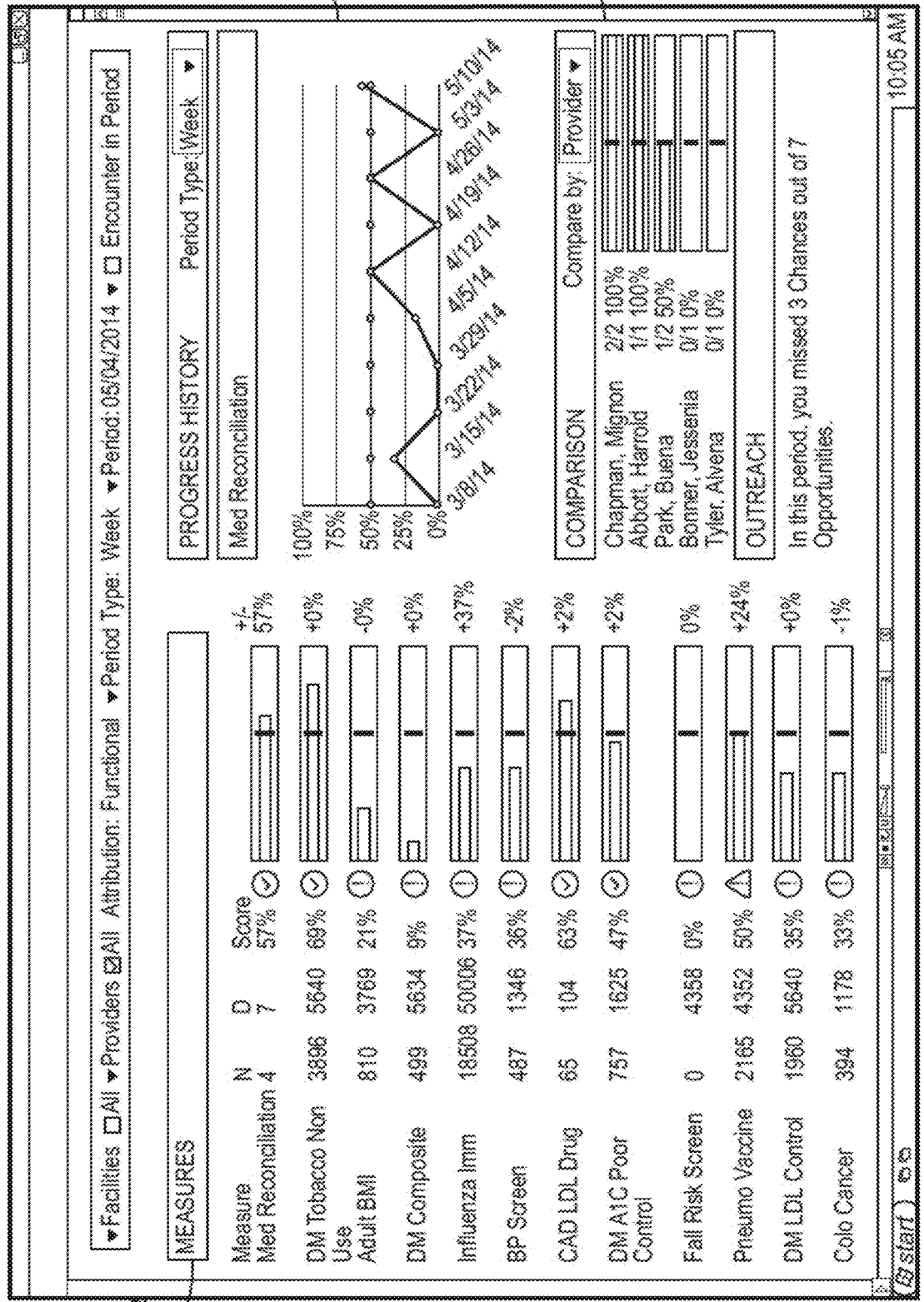
FIG. 10C shows a measure report.

The user interaction module 112 facilitates access to standard sets of reports related to such topics as: performance management including initiatives, collections of metrics and measures; utilization analysis of services and the like; patient management; and the like. The reports may include, for example, a measures report (FIG. 10C), regarding the measures 1022, a graphical representation of performance over time 1024, comparisons 1028 based on various criteria such as provider and the like.

Figure 10D:
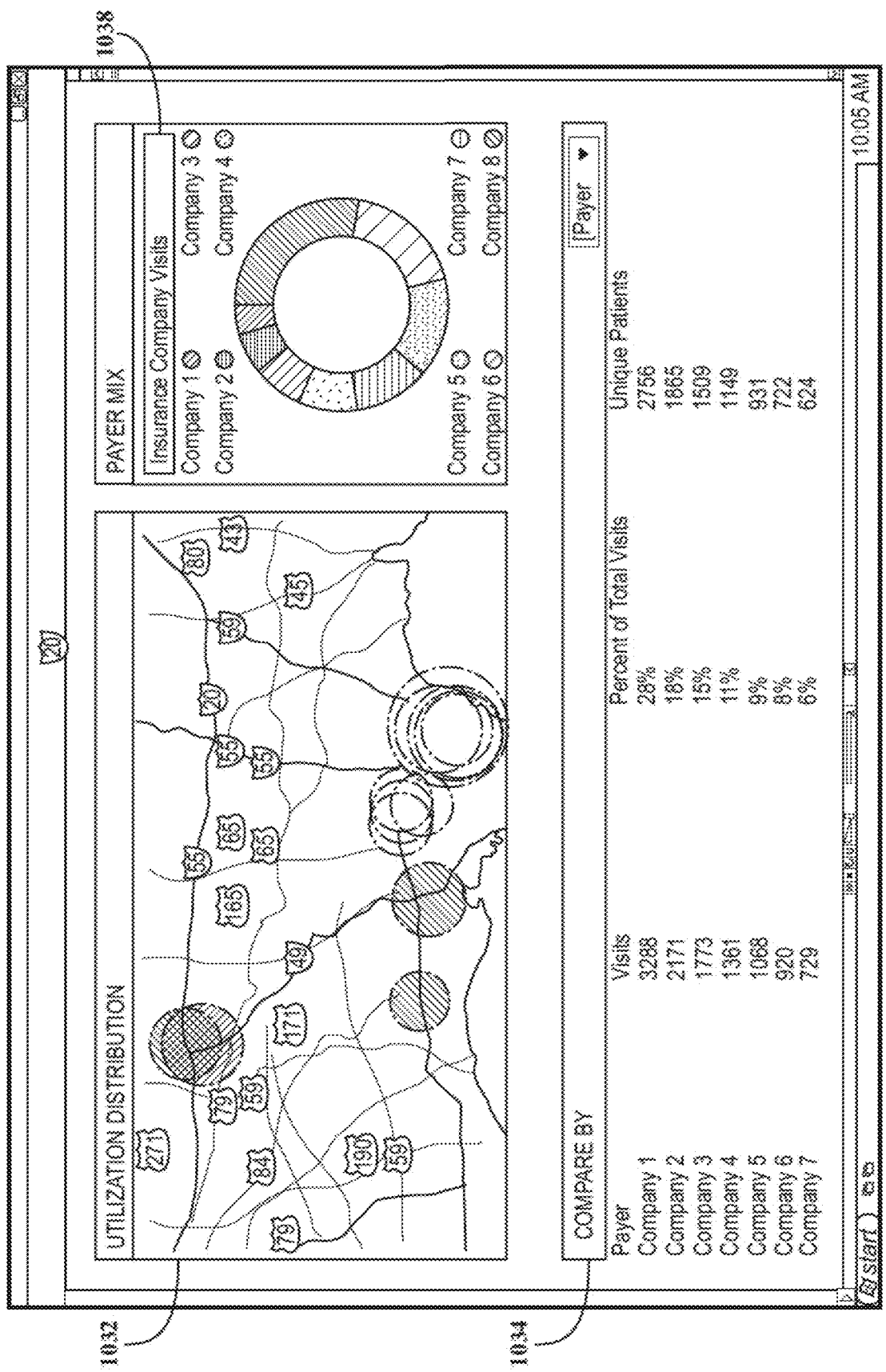
FIG. 10D shows the integration of data with mapping data.

The user interaction module 112 further provides for the integration of data with $3^{rd}$ party applications such as Google maps, and other such mapping interfaces (FIG. 10D). Data from the data warehouse 142 may be passed to an API to combine with a data from $3^{rd}$ party applications. The combined data may facilitate insights into the location-associated data. The location-associated data, for example, a map overlaid with utilization information 1032 in the form of bubbles of differing areas and detailed payer information 1034 is shown together with a graphical representation of payer contribution 1038. The user interaction module 112 may support integration with data from $3^{rd}$ party sources such as databases of health care locations clinical trial outcome data, medication data (e.g., including warnings, drug interaction data), transaction data sources (e.g., credit scores) and the like.

Data viewable, as well as filter options available, may vary for any given report by user login and class. For example, a health care provider may receive reports such as the day's patient list, the week's patient list, which patients are high risk, which of their patients has visited the emergency room recently, which patients are seen frequently, and the like. A facilities administrator may receive reports on facility usage, physician performance and the like.

An administrative user or lead operator may specify user permissions (FIG. 11A). An administrative screen 1100 may allow an administrative user to specify user privileges such as user type 1102, provider attribution 1104, viewable facilities 1108 and viewable providers 1110, administrative privileges 1112, and the like.

Figure 11B:
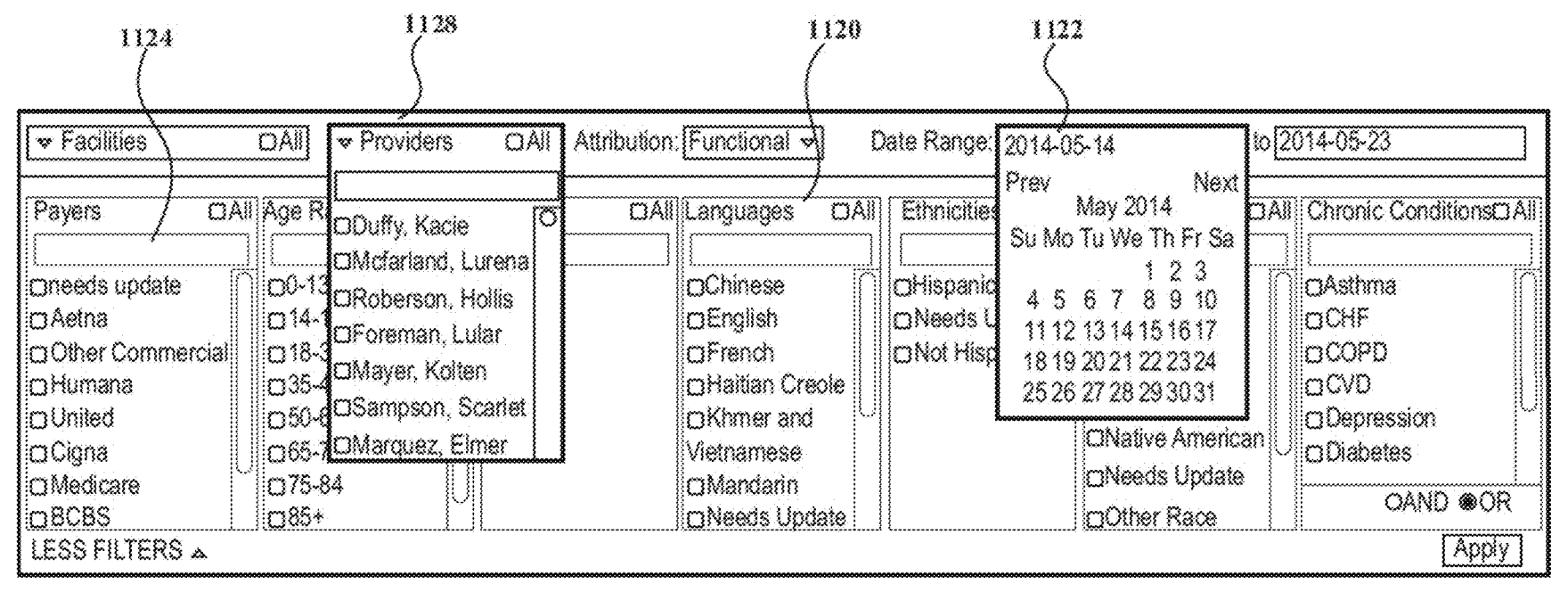

On a given page, individual users may further enhance their view of the data by filtering the data displayed (FIG. 11B). The reports may include, for example, attributes filtered by selection of one or more from a list of values such as providers 1128, languages 1120, payers 1124, ethnicities, facilities, location, demographics of patients, chronic conditions, rendering provider, or usual provider (PCP). A date may be visually selected from a calendar 1122. Individual users may select to display a subset of the data provided by a given report or the order in which it is displayed on the screen. Display preferences for a given report may also be saved as a favorite or default for use in the future.

The reports may include, for example, a risk report 1200 (FIGS. 12A-1 and 12A-2) that supports filtering data by specifying values for various attributes such as risk level 1202, per member per year (pmpy) cost 1204, date range 1208, rendering provider 1210, next appointment 1212, and the like.

Detailed patient information may be reached from a list that includes a subset of patients. In one non-limiting example, an administrator may chose to show telephone numbers when listing upcoming patients to facilitate reminder phone calls. Alternately, a physician may choose to view risk levels when viewing upcoming patients. In an illustrative and non-limiting example, data on an individual location may be selected from a higher-level report on the relative performance of different locations. Individual users may drill down within an individual report to see more detailed information about the supporting information.

The user interaction module 112 may have an option to export the complete data supporting a given report as a data file. The exported data file may be a comma separated value (csv) file, an Excel file, et.c, to enable a user to further analyze the data using other tools.

Risk scores are most typically calculated for a person based in part on: demographics such as age, gender, level of infirmity, and such; diagnosis information reported in claims data for that person; health care program enrollment; and others. Risk scores are calculated for people or groups of people who may be patients, members of a group or health care plan, providers, support staff, and others. References to "patients" herein, however, are not meant to be limiting, and should be understood to refer to any individual person, or group of people. It should be appreciated that any risk adjustment model based on the diagnosis codes, procedure codes, drug codes, laboratory codes, and any other code-based risk mechanism may be utilized to facilitate calculation of the risk scores. However, current methods, which involve time-consuming, manual review by trained individuals, may be cost prohibitive.

A risk score represents the expected total cost of care of a given patient relative to the average per-patient cost of care over the entire population. A clinically supplemented risk score for a given person may facilitate in managing care for that person by identifying specific risks for that person. The clinically supplemented risk score for a population of interest may facilitate attribution of costs and effort among a group or provider. Clinically supplemented risk scores by categories such as diabetes, depression and the like may facilitate current and future resource planning for an organization. The clinically supplemented risk score may also inform premium reimbursement rates from payers such as CMS/Medicare, Medicaid and the like such as providing higher reimbursement rates in response to higher risk levels.

A risk score may be calculated on a regular, often nightly, basis by the data warehouse 142 for each person therein based on the available clinical data for each individual. A risk score may be calculated in real time to include the most recent data available. The risk score may be personalized such that the risk scores are reflective of the actual medical history and current conditions for each person and for the population of interest as a whole.

A scoring process may be utilized to assign each individual one or more of a total risk score, an 'open' risk score based on inferred diagnostic conditions, a 'closed' risk score based on suspected or known conditions for which there exists a documented encounter, blended risk scores, assignment of an individual to one or more of a set of condition categories and such. Condition categories may be identified using 'Hierarchical Condition Categories' (HCC) logic based on an algorithm from the Centers for Medicare and Medicaid Service (the (CMS)-HCC algorithm), which may be reviewed annually. Conditions may be identified using other models, which may be adjusted outside of an annual process.

Figure 12B:
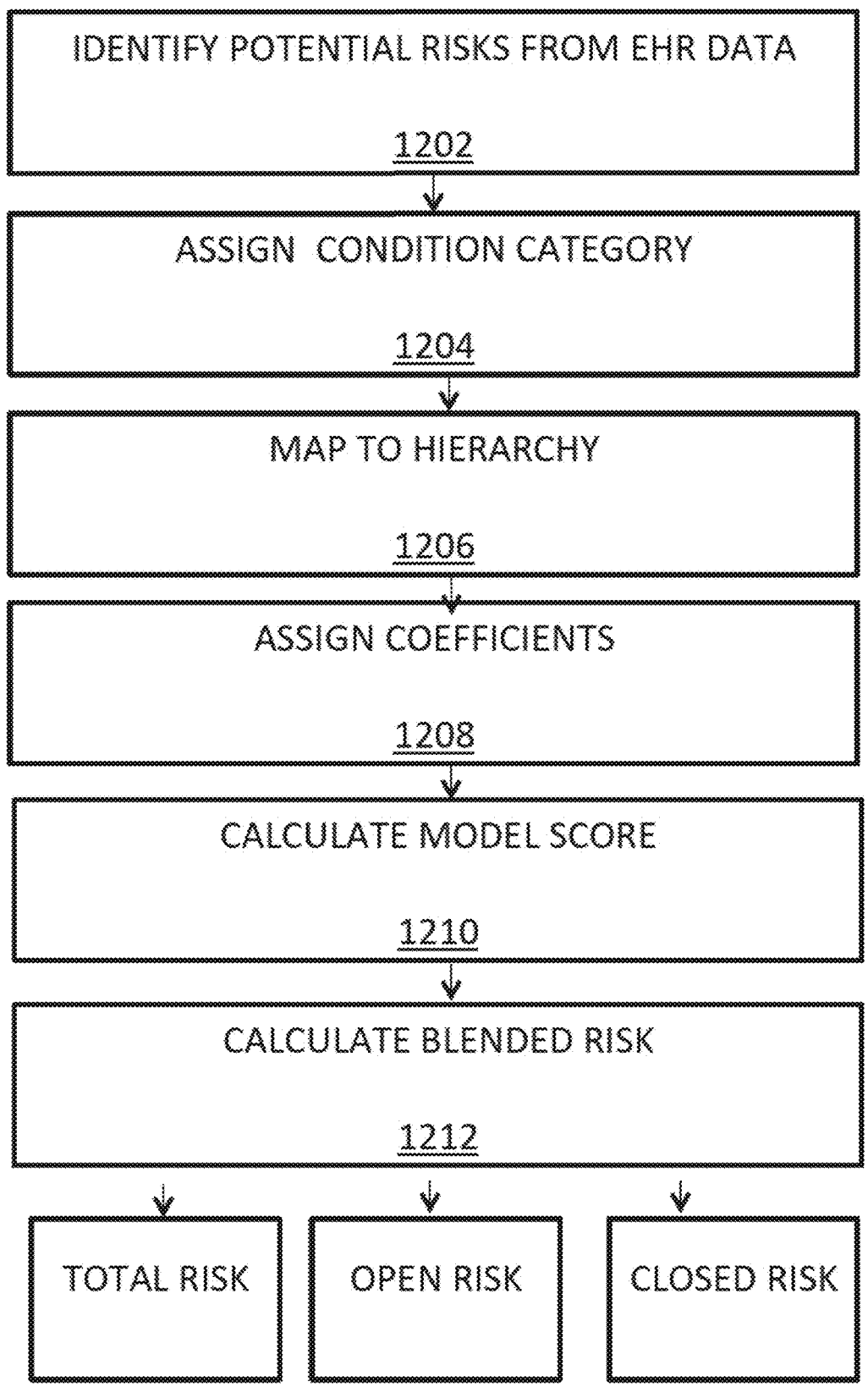
FIG. 12B shows a flowchart for calculating risk scores.

With reference to FIG. 12B, in one disclosed non-limiting embodiment, one or more risk scores and an associated risk report 1200 may be generated by identifying potential risks from a plurality of sources such as individual electronic health records (EHRs) (step 1202), claims data, payer reports, and other data sources. The collection of data may include documented diagnosis, which may be immediately actionable. Sources for such documented diagnoses may include: claims during the service period where the procedure code is for a medical encounter or inpatient procedure type; signed progress notes from a medical encounter during the service period; assessments from medical encounters during the service period; and such. For example, a signed progress note typically contains one or more assessments of diagnosis codes, which may be part of a HCC group. Risks or gaps identified from these sources are considered 'closed' gaps.

Data underlying a 'closed' source risk score may facilitate identifying opportunities for short-term action such as diagnoses related to claims, clinical data, and such during a service period. Illustrative examples of opportunities for short-term actions for a practice related to 'closed' scores may include: identification of a signed progress note documented in EHR but for which no claim was generated; a patient was seen and a claim was generated but no diagnosis code was received by the payer; a provider saw a person and in documentation of the visit made and recorded an assessment of an ongoing condition unrelated to the call, and the like. In some instances, the unrelated assessment and diagnosis may be put into the notes, either as text, a standard diagnostics codes, or a generic code, as described above, but not recorded in the encounter process note. In some instances, the presence of a "generic code" may result in additional processing of the notes, encounter process notes, and the like, using techniques such as pattern matching, topic modeling, natural language processing, other forms of machine learning and the like as described elsewhere herein.

The data may also be collected via diagnosis codes from non-immediate opportunity sources—these sources are considered 'open' gaps. An 'open' gap may be based in part on suspected or known conditions that are inferred from other sources such as prescription records, lab orders, patient vitals, and the like or may be related to older data such as, for example, claims or encounters from months or years prior to the start of the current service period. Examples of such data may include a problem list entry or other diagnosis annotation in the EHR. An example of a problem list includes an EHR module that documents known conditions, along with onset and offset (if applicable) using diagnosis codes, condition descriptions in open or closed text format comprising one or more of onset, offset, manifestation and severity for a prior period, such as, for example, in the previous 24 months. An entry in the problem list may indicate the presence of an ongoing or chronic condition. Presence in this group may reveal care gaps and/or documentation disconnect. A claim from any time in the prior period but before start of the service period where the CPT code is for medical encounter or inpatient procedure type. Other data includes notes and assessments from medical encounter any time in a prior service period but before the start of the service period.

Still other, non-immediate, opportunity sources may include medication listings and prescription records/claims that were prescribed or filled in a prior period. For example, a pharmacy claim, medication listing, lab order, or the result of a lab order may indicate the presence of a specific condition. Further, records of events, referrals, and medical history notes suggestive of a condition and notated in the prior service period may explicitly or implicitly indicate the presence of a condition, presently or in the past. This group may indicate a care gap or documentation disconnect.

Figure 12C:
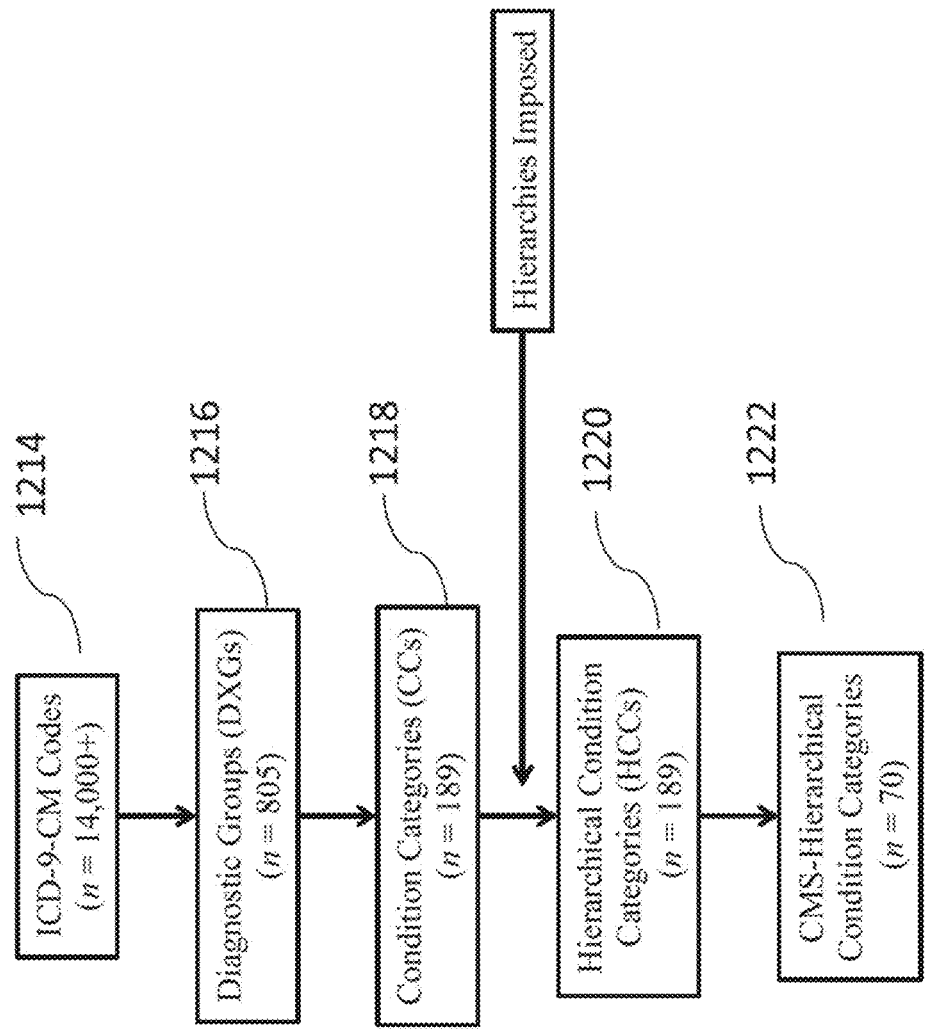
FIG. 12C shows an example of aggregating diagnoses into hierarchical conditions.
Figure 12D:
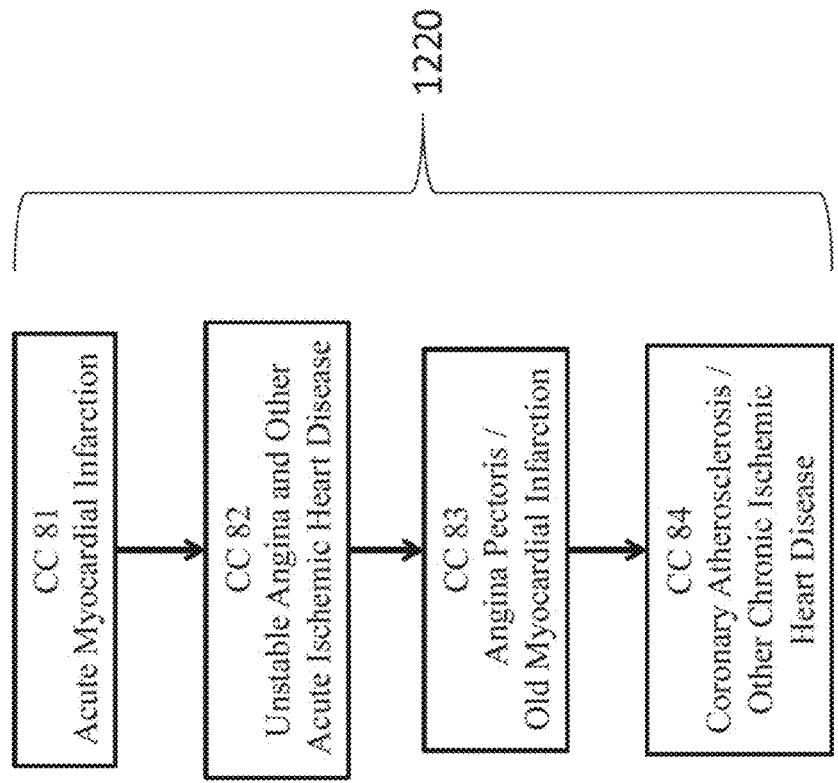
FIG. 12D shows an example of hierarchical conditions

Following the analysis of the EHR data and the identification of documented and inferred diagnostic conditions and risks, the identified risks may be assigned to one or more condition categories (step 1204) and these categories further mapped into a hierarchy (step 1206). An example of this type of mapping is represented in FIGS. 12C-12D where FIG. 12C shows the aggregation of individual diagnoses codes 1214 (in this example the International Classification of Diseases, Ninth Revision, Clinical Modification (ICD-9-CM) Codes) into Diagnostic Groups 1216 and Condition Categories 1218.

Figure 12E:
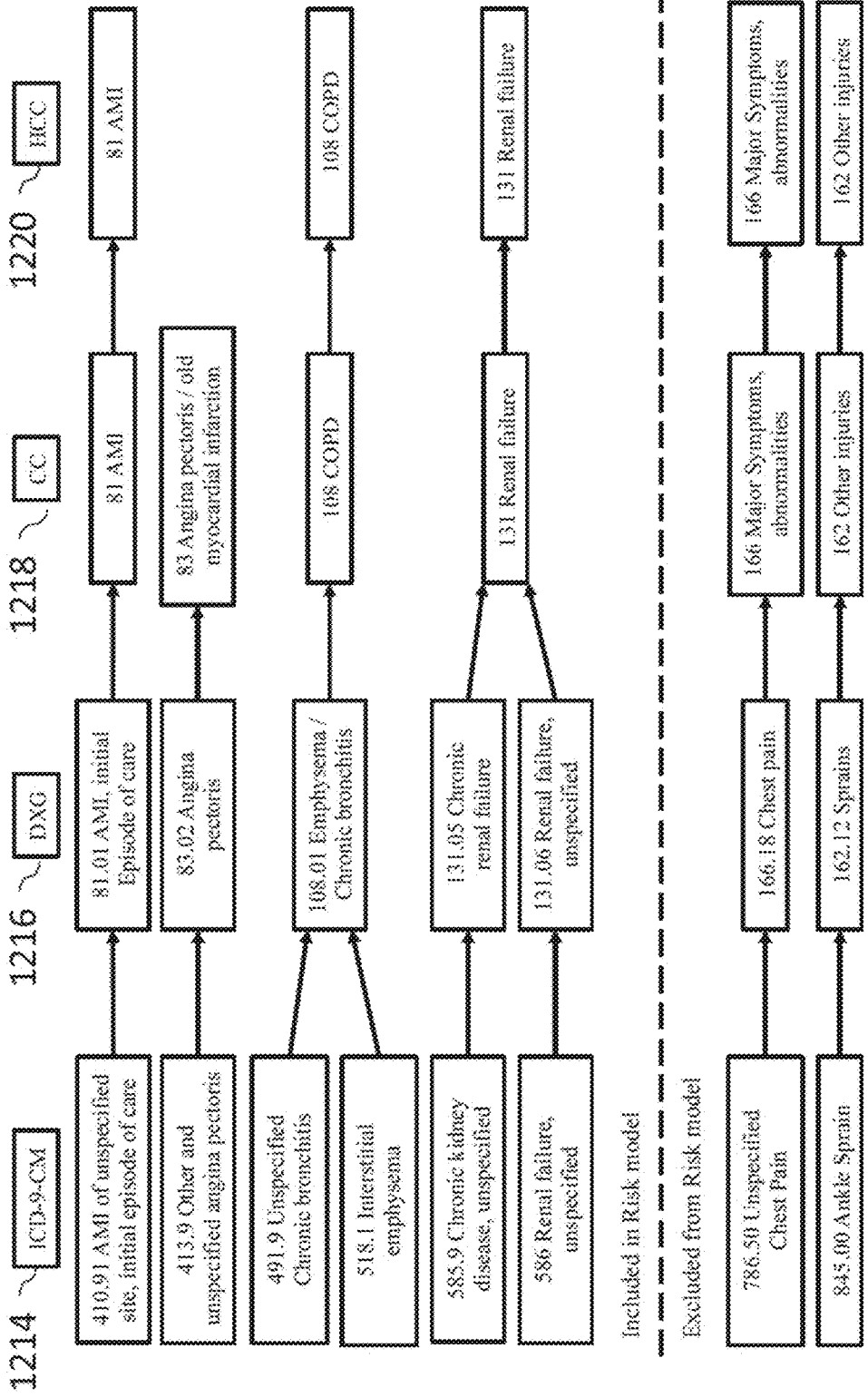
FIG. 12E shows an example of aggregating diagnoses into hierarchical conditions.

Next, the mapped conditioned categories may be refined into a hierarchy of condition categories (step 1206). An example of hierarchical condition categories is represented in FIG. 12D. Should a patient have an HCC condition documented in multiple sources, the highest-certainty ('closed') source may be used in the hierarchy. Should a patient have multiple conditions within an HCC hierarchy, conditions that are lower in the hierarchy may be excluded so they will not be added to the score (e.g. if patient has codes for "moderate" and "severe" diabetes, the code for "severe" diabetes may be used). Condition categories and hierarchies may also be further assigned to broader categories (e.g. "Infection", "Heart") for easier interpretation and use, such as using the CMS Hierarchical Condition Categories 1222. In an illustrative and non-limiting example, as shown in FIG. 12E, specific diagnostic codes 1214 are mapped to diagnostic groups 1216, condition categories 1218 and hierarchical condition categories 1220. The illustrative examples of FIGS. 12C-12E use the mapping provided by the Centers for Medicare and Medicaid Service. This is not intended to be limiting and other hierarchies may be used.

Next, each individual is assigned one or more applicable coefficients (step 1208) for use in the calculation of risk scores (step 1210). The coefficients for an individual patient may be based on the individual's demographics, identified risks, and the like where the coefficient for a condition may vary based on the type ('open' or 'closed') of source. The coefficients are generally linear and may be applied in any order. In some instances, where particular combinations of demographics, disabilities and conditions or multiple (pairs or trios) of conditions that interact exist, a different coefficient set may used to assign the coefficients, an additional interaction coefficient may be added into the model, coefficient weightings may be adjusted, and the like. These coefficients at the 'individual' level are in a traceable form facilitating the ability for a user to see the details of the condition, disease, and/or demographic codes that contributed to inclusion of certain coefficients and their impact on the individual's risk score/assessment. An illustrative example of the contribution of risk factors based on underlying conditions to total risk score is shown in FIG. 12F.

Finally, clinically supplemented risk scores may be calculated for one or more risk models (step 1210). A blended risk score may be calculated (step 1262) where the blended risk score may be a sum of all the model-specific, non-excluded coefficients to determine each person's raw model score. If desired multiple models may be blended using pre-assigned rules/coefficients and apply normalization factors for final, blended risk scores. For the Total Risk Score, all the coefficients from all sources, whether 'open' or 'closed' gaps are included—this score represents all evidence of chronic conditions. For the 'closed' gap risk score, only coefficients from sources reflecting 'closed' gaps are included—this score represents only the existing, documented events during the service period.

Identifying potential risks or 'gaps' from EHR data (step 1202) may comprise a plurality of techniques. The EHR data may be parsed based on data field or using one or more techniques such as direct string pattern matching (through tokenization of input), topic modeling, dictionary lookups through fuzzy matching, natural language processing, machine learning and the like to identify data of interest such as diagnosis codes, medications and medication codes, laboratory orders and results, vital statistics, annotations of interest, and the like. For example, the presence of diagnosis codes 1214 in a claim or billing document, notes for an assessment or encounter, a "Problem List" entry, or other diagnosis category may be used. Text notations may be processed using one or more techniques such as direct string pattern matching (through tokenization of input), topic modeling, dictionary lookups through fuzzy matching, natural language processing, machine learning and the like to identify words and phrases that may be mapped to a specific diagnosis code 1214, diagnostic groups 1216 or condition category 1218, as specified above. In addition to identifying sources of risk, this technique may be used to identify the presence of previously un-notated conditions and gaps in reimbursement documentation.

Medication list entries, medication prescriptions and the like may be identified using medication names, National Drug Code (NDC) designations, and such. These may be compared against a list of medications known to be highly correlated with specific risk conditions. That is, if the medication has only a single use or application the associated diagnostic condition may be inferred, such as inferring diabetes from a prescription for insulin. Medications or drugs associated with multiple uses are typically not used to infer risk unless there is a single predominant use or the other uses may be ruled out based on other data. Existing NCQA HEDIS specifications provide guidance on using administrative data like prescriptions to identify conditions or other identification schemes may be used.

Figure 12G:
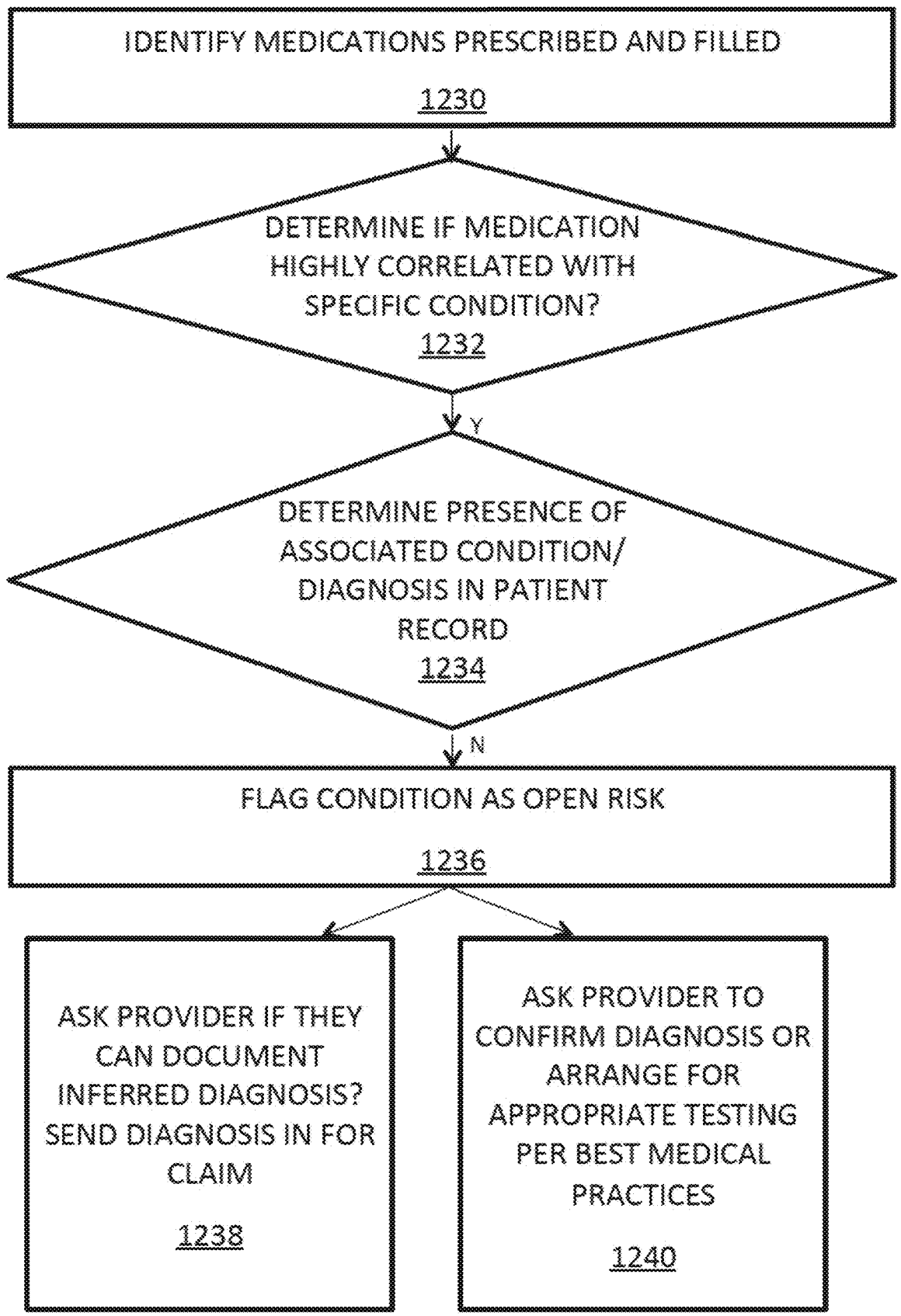
FIG. 12G shows a flowchart for inferring diagnostic conditions from medications.
Figure 12H:
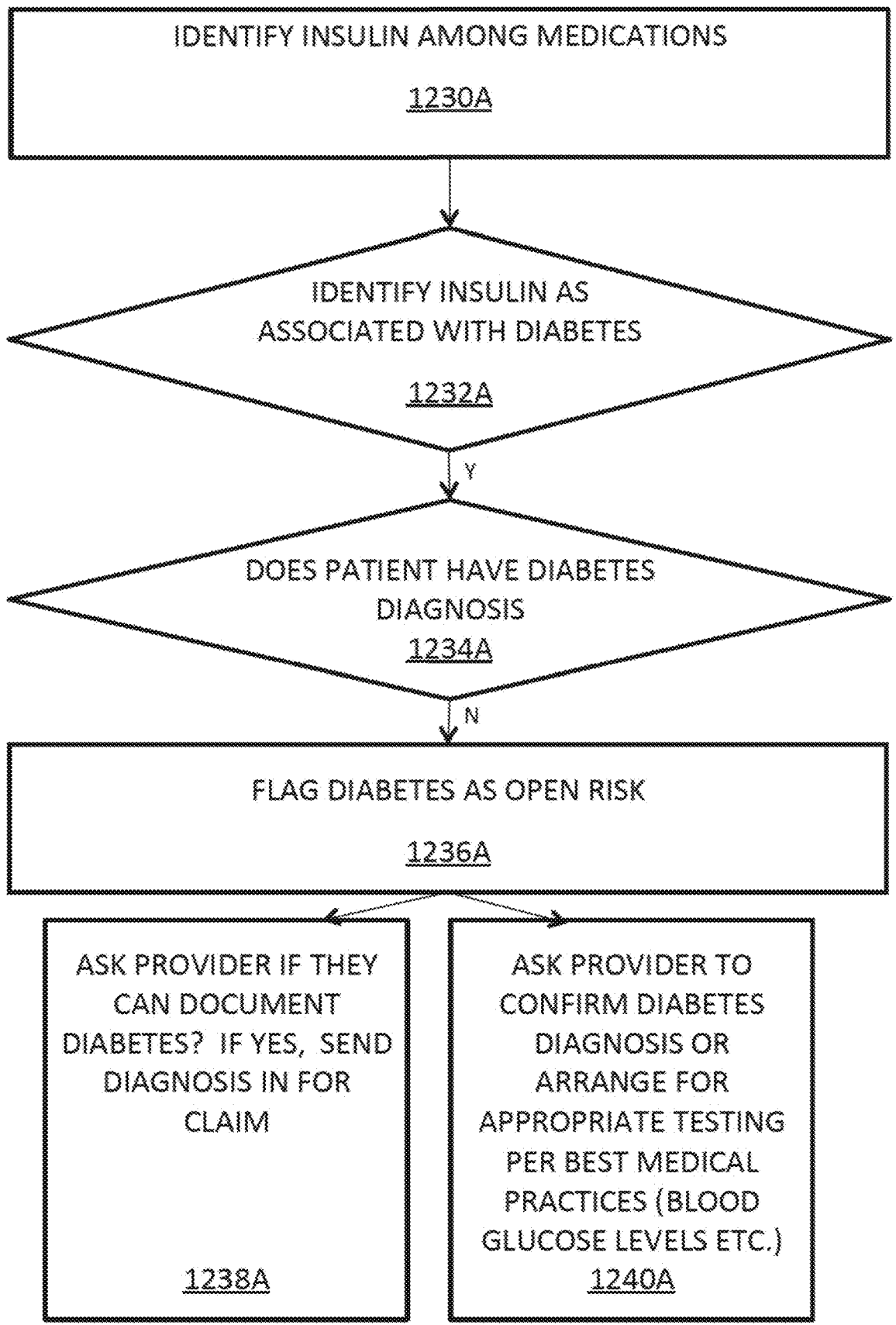
FIG. 12H shows an example of inferring a diagnostic condition from a medication.

In an illustrative and non-limiting example, FIG. 12G shows a flow chart for inferring conditions from medication records and acting upon the inferences. Identify medications prescribed and filled (step 1230) using techniques such as pattern recognition of known medication identifiers, including National Drug Code (NDC) designations and medication names, natural language processing and the like. Determine if medication is highly correlated with specific conditions and risks (step 1232). If a specific condition is identified, determine presence of associated condition/diagnosis in the patient's EHR (Step 1234). If the identified condition or diagnosis is not present, the condition may be flagged as a risk (step 1236) and one or more actions may occur such as contacting the care provider to see if they can document the inferred diagnostic condition (Step 1238), contacting the care provider to confirm the inferred diagnostic condition or arrange for appropriate testing and diagnosis of patient according to best medical practices (step 1240), and the like. FIG. 12H walks through the flow chart of FIG. 12G using an example of a prescription for insulin. Insulin is identified in the medication list (step 1230A). Insulin is used to access a database of medications with highly correlated conditions and insulin is determined to be associated with diabetes (step 1232A). Upon review of the patient record, no diagnosis of diabetes is found (step 1234A) and diabetes is flagged as an undocumented risk (step 1236A). In some instances, the physician may be contacted to provide documentation of diabetes (step 1238A) or to confirm the inferred diagnostic condition of diabetes such as through a blood glucose test (step 1240A).

Identification of ordered laboratory tests and laboratory results may be used to infer certain risks, diagnosis codes and condition categories. Certain laboratory tests and lab results may be highly correlated with specific conditions and risks. In some instances, LOINC codes (a commercially available collection of universal lab order codes) may be identified in the EHR and used to access a lookup table mapping the lab order names to conditions where the condition is highly correlated with the particular lab order. In some instances, results of the identified labs may be evaluated against best practices/accepted values encoded in a lookup table and out-of range lab results identified. In some instances, out-of-range lab results may be highly correlated with a particular risk or condition. For example, numerous HbA1c tests are commonly done on individuals with diabetes and the presence of numerous HbA1c test orders in an individual's electronic health record may be used to infer a diabetic condition in the absence of a specific diagnosis code indicating diabetes. The results of a common test may also be used to infer certain diagnoses or condition codes such as "high" results on HbA1c tests or glucose tests may be indicative of diabetes or pre-diabetes. The combination of both the text requests and test results may indicate a higher likelihood of the presence of certain diagnostic conditions/codes. In some instances, the lab result must be out-of-range over a certain time period or over a certain number of tests for a risk condition to be flagged.

Vital statistics may be used to infer certain risks, diagnosis codes and condition categories by comparing values against out-of-range values encoded in lookup tables and associated with conditions. Identification of risk may include a weighted, additive process where multiple out-of-range readings may be necessary prior to flagging a potential risk condition. In an illustrative and non-limiting example, three blood pressure (BP) readings of BP>140/90 may indicate hypertension or other high BP-related conditions where a single reading of BP>140/90 may not flag hypertension as an inferred diagnostic condition.

Other source of data which may be used to infer diagnostic conditions may include reconciliation entries in an EHR, or any other "event" such as a diagnostic tool, encounter type, and the like, that is associated with a condition.

Figure 12I:
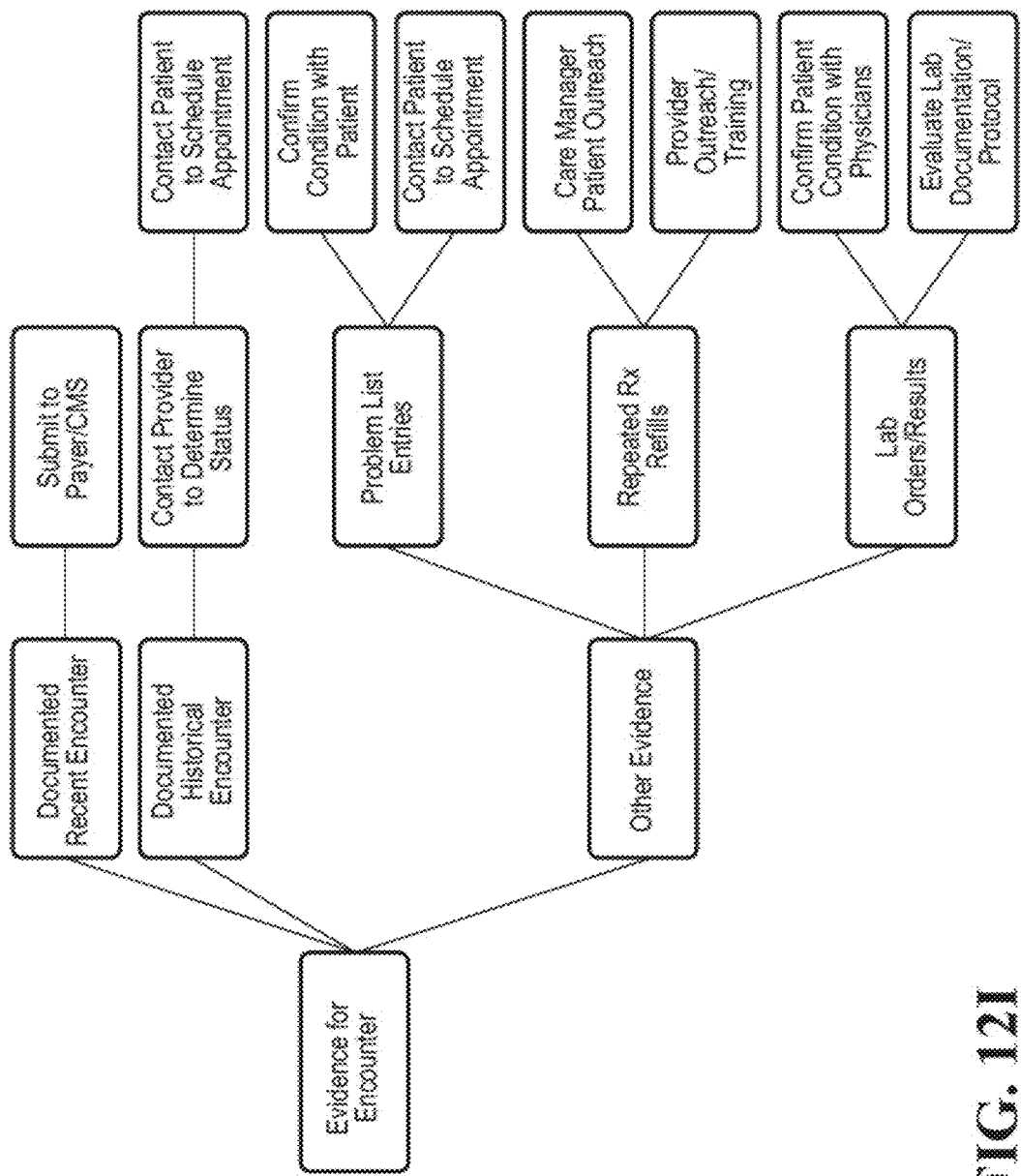
FIG. 12I shows a flow chart for determining actions based on supporting data type.

As shown in the illustrative flow chart of FIG. 12I, based on the type of supporting evidence, the newly identified risks may be used to identify various next actions. There may be multiple levels of actions: a patient level that identifies specific interventions for patients with care gaps; a provider level that builds "chase lists" or lists of activities such as obtaining documentation from specific providers, identifying providers for interventions, such as developing a more effective workflow or better incentive program; and a practice level that identifies practices and groups for better workflow to integrate improved reporting and care. The score results are outputs intended for usability and some of the intended actions are illustrated in FIG. 12I.

A documented recent encounter may be reported to a payer for reimbursement. Other, 'open' gaps may suggest patient specific actions such as scheduling a follow-up appointment, confirming patient condition with patient or physician, identifying care protocols such as additional testing and medications for review by physician, care manager and the like.

Tables 1 and 2 describe an example prioritization of the opportunities based on supporting documentation including exemplary methods for identifying the risk, mapping the risk to a diagnosis and examples of appropriate action to take based on the newly identified risk.

TABLE 1

| | Prioritization of Supporting Evidence and Risk Identification | | |
|---|---|---|---|
| Priority | Supporting Documentation | Description | ID Algorithm |
| 0 | Complete | Event has occurred in Service Year and submitted to top-level funder | Processing of diagnosis codes (dx) submitted to top-level funder. Identification of known risk codes from funder feedback |

TABLE 1-continued

Prioritization of Supporting Evidence and Risk Identification

| Priority | Supporting Documentation | Description | ID Algorithm |
|---|---|---|---|
| 1 | Current Claims | Claim for appropriate diagnosis code from encounter in Service Year has been submitted to Plan | Processing of diagnosis codes submitted to Plan by providers. |
| 2 | Progress Notes | Signed progress note with appropriate diagnosis code for condition listed present in EMR. | Processing of diagnosis codes attached to progress notes in provider EHR. |
| 3 | Assessments | Assessment with appropriate diagnosis code for condition occurred connect to qualified patient encounter | Processing of diagnosis codes attached to assessments linked to patient encounters in provider EHR. |
| 4 | Problem List | Active Problem List entry with appropriate diagnosis code for condition present during Service Year. | Processing of diagnosis codes attached to Problem List entries in provider EHR. |
| 5 | Medications | Active Medication List entries in the EMR and prescriptions in claims or the EMR associated with condition. | Scan drug NDC codes for matching codes; scan medication names for common and generic roots of drug names. |
| 6 | Unqualified Events | Events in the current Service Year that were not a qualifying encounter but could indicate the presence of a condition. | Processing of diagnosis codes attached to non-qualifying encounters events (labs, ED, diagnostics, etc.) in provider EHR and plan claims; identification of overuse of "generic" diagnosis codes by providers potentially masking higher severity conditions. |
| 7 | Historical Events | Events prior to the Service Year that indicated historical presence of the condition. | Processing of diagnosis codes attached to claims and events in the provider EMR prior to the Service Year; identification of risk codes from funder feedback prior to the Service Year. |
| 8 | Laboratory Events | Laboratory orders and results in the Service Year associated with the presence of a condition | Scan order LOINC codes for matching codes; scan order names for matching order types; scan lab results for out-of-range results. |
| 9 | Vitals/Diagnostics | Patient vitals or diagnostic results associated with the presence of a condition | Scan vitals values and diagnostic results for out-of-range values. |
| 10 | Other Indicators | Any other indicator of the presence of a condition, including test searches, pattern matching, language processing, condition forecasting, etc. | Varies. May include text searches, pattern matching, language processing, condition forecasting, etc. |

TABLE 2

Supporting Documentation mapping and Exemplary Interventions

| Priority | Name | Mapping Mechanism | Status | Example Intervention |
|---|---|---|---|---|
| 0 | Complete | Alignment of diagnosis codes with published risk-dx mapping. | Closed | None Needed |
| 1 | Current Claims | Alignment of diagnosis codes with published risk-dx mapping. | Closed | Confirm submission (or resubmit) appropriate dx codes to top-level funder. |
| 2 | Progress Notes | Alignment of diagnosis codes with published risk-dx mapping. | Closed | Confirm progress note dx code with provider as needed; submit dx code to top-level funder. |

TABLE 2-continued

Supporting Documentation mapping and Exemplary Interventions

| Priority | Name | Mapping Mechanism | Status | Example Intervention |
|---|---|---|---|---|
| 3 | Assessments | Alignment of diagnosis codes with published risk-dx mapping. | Closed | Confirm assessment dx code with provider as needed; submit dx code to top-level funder. |
| 4 | Problem List | Alignment of diagnosis codes with published risk-dx mapping. | Open | Confirm with provider or care coordinator whether a current encounter may have occurred; arrange for removal of "stale" Problem List entries; arrange outreach efforts with care coordinators to close gaps moving forward. |
| 5 | Medications | NDC and drug name/generic lookup tables based on best practices or national standards map to lowest-severity risk code in appropriate category. | Open | Confirm condition with prescribing physician; explore whether an undocumented encounter may have occurred; arrange outreach efforts with care coordinators to close gaps moving forward. |
| 6 | Unqualified Events | Alignment of diagnosis codes with published risk-dx mapping and lookup tables of "generic" diagnosis codes with potential higher severity categories. | Open | Create "batches" of cases with similar conditions for member or provider outreach; identify heavy users of generic codes for workflow improvement. |
| 7 | Historical Events | Alignment of diagnosis codes with published risk-dx mapping; potential grouping by acute (e.g. treatable infection) vs. chronic/pervasive (e.g. COPD, amputation) conditions. | Open | Create "batches" of cases with similar conditions for member or provider outreach; facilitate removal of "stale" data that are no longer relevant. |
| 8 | Laboratory Events | LOINC and lab order name lookup tables based on best practices or national standards map to lowest-severity risk code in appropriate category. Lab results checked against best practices or national standards for out-of-range value map to appropriate severity risk code in appropriate category. | Open | Generate "chase lists" of members for provider review, along with appropriate lab orders or results; as needed, facilitate outreach by care coordinators to assess conditions and determine whether further care is needed. |
| 9 | Vitals/ Diagnostics | Vitals values and diagnostic results checked against best practices or national standards for out-of-range value map to appropriate severity risk code in appropriate category. | Open | Generate "chase lists" of members for provider review, along with appropriate vitals and diagnostic results; as needed, facilitate outreach by care coordinators to assess conditions and determine whether further care is needed. |
| 10 | Other Indicators | Mapped to appropriate severity risk code within matching category | | Identify members with potential care gaps for outreach; identify providers with potential workflow or documentation gaps for outreach. |

For each source, the severity and associated coefficient are identified and tagged, with the source of information such that the data may be mapped to condition categories. Condition category mappings may vary based on member demographics, program enrollment, health status, and the like.

The mapped data may then be stored at the 'person' level so that the user can view risk at varying levels of detail and trace a risk assessment to the patient level and the specific documentation that contributed to the risk rating. The ability to easily identify the source of risks and view underlying activity may increase the ability of a reviewer to act upon the identified risk to resolve or reduce the risk.

Figure 13A:
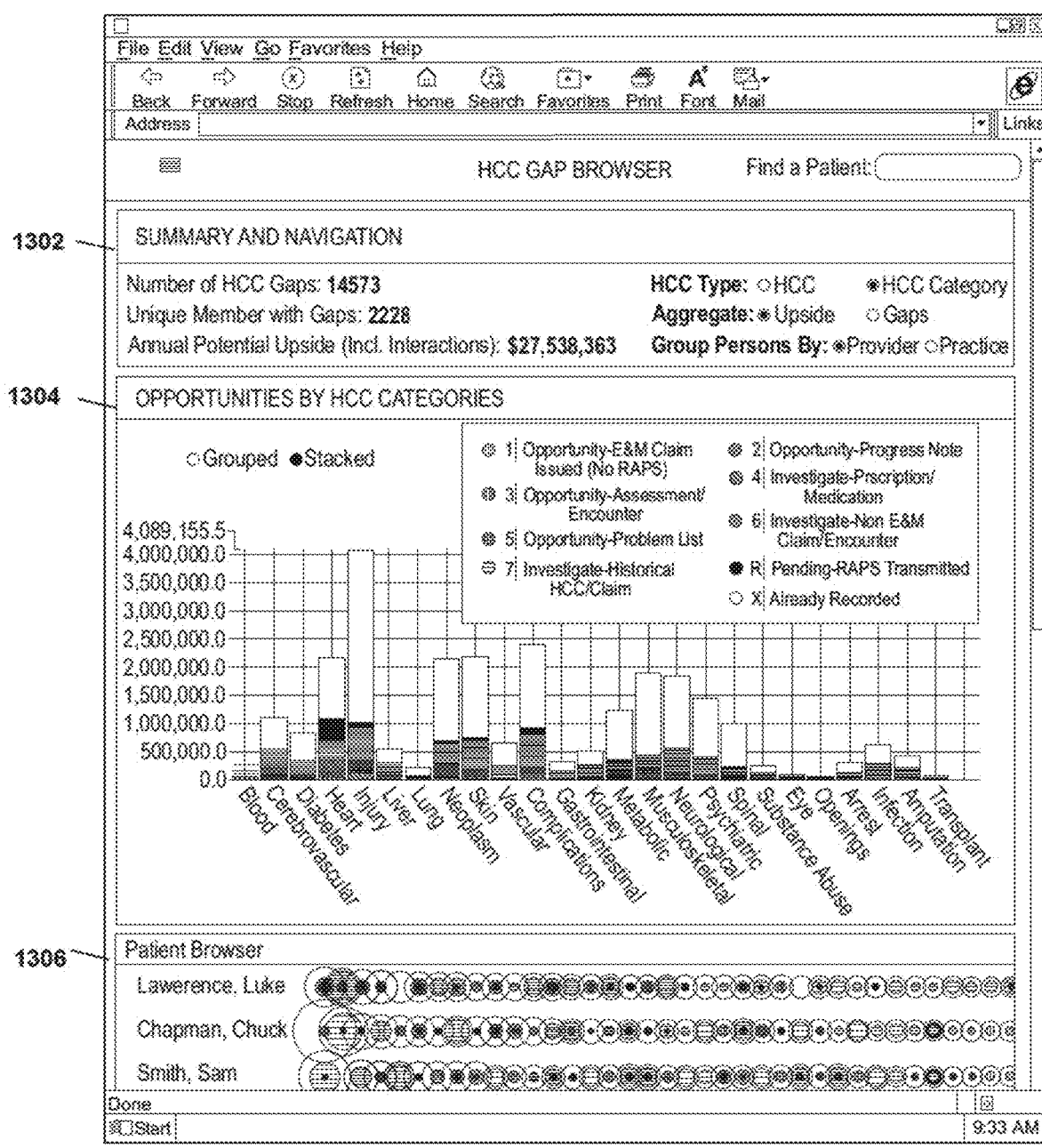
FIG. 13A shows an example of a risk summary report.

With reference to FIG. 13A, the resulting scores are highly multi-dimensional where categories may include one or more of demographics (e.g. gender, age, location), provider, facility, major risk category, minor risk category, broad categorization of open vs. closed risk sources, detailed categorization of risk sources, opportunities that are immediately actionable vs. opportunities that are strategic, evidence for the completed service year vs. evidence for the current service year, and the like and results may be filtered by category and viewed on an interactive browser or graphical user interface for improved navigation and insight.

The interactive graphical user interface readily facilitates user interaction with the risk scores and risk report data in an intuitive manner such as via clicking on information of interest to see more detail. Displayed results may include summary statistics about member population 1302, such as aggregated counts of open and closed gaps, the potential dollar upside revenue for closure of identified CMS-HCC conditions where there is a known dollar mapping. The results may be displayed in a way reflective of opportunities by category 1304 (e.g. diabetes, heart), opportunities by type (e.g. encounter, medication), opportunities by patient 1306, and the like. Individual recovery opportunities may be toggled on and off by clicking on an item to highlight specific groupings of opportunities.

Figure 13B:
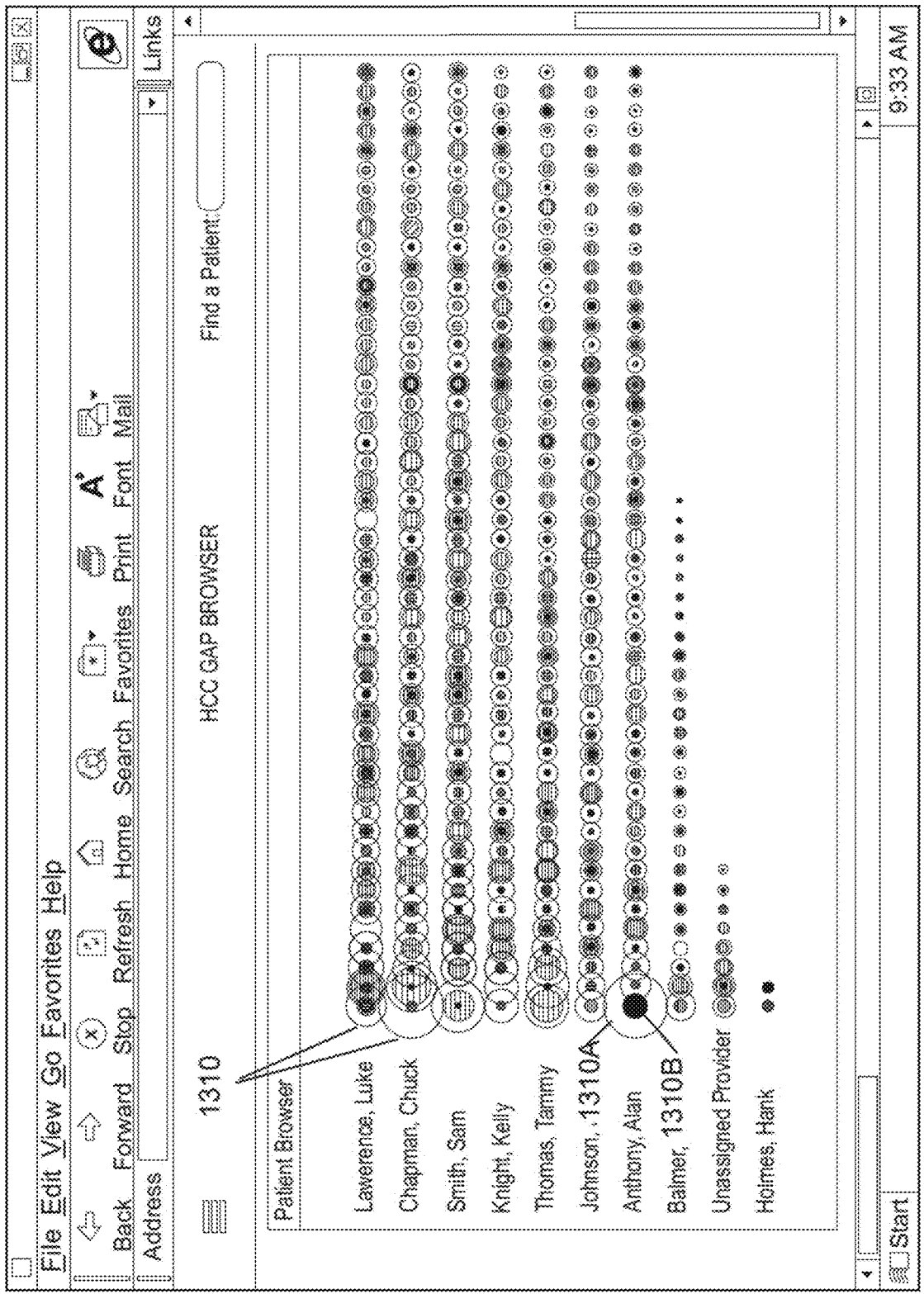
FIG. 13B shows an example of a risk report summary by patient.

With reference to FIG. 13B, the score results may be displayed by provider names, in this example, providers assigned to a patient panel via a respective icon 1310. Each icon 1310 may represent a patient in the providers' panels. In this example, the symbology utilizes circles, however, other icons may alternatively or additionally be utilized. The size of each icon 1310 may represent the number of care gaps identified for the individual, and the circles may be colored or textured to indicate the opportunity group or source for those care gaps. The patients may be arranged from left to right in order of total size of opportunities. Since gaps may be identified for an individual from many sources, the icons may be concentric circles 1310A 1310B representing varying levels of opportunity. By hovering a mouse over a circle, a user may get statistics on the gaps for a specific patient from a specific source.

By clicking on a respective icon 1310, the user may get a detailed display of care gaps/opportunities identified for that patient, organized by source (as shown in the chase list of FIG. 13C). Chase lists (FIG. 13C) may include: suspected care gaps where there appears to be a lack of a service that would be expected given a patient's condition; documentation gaps between care delivered and billed; and others. Chase lists 1312 may be color coded to indicate type of opportunity. Chase lists 1312 may be interactive where selection of a patient reveals patient detail record (FIG. 13C). The patient display shows complete list of discovered gaps, descriptions, and source ordered by opportunity and likelihood of recovery. Selection of particular rows brings up original source for immediate confirmation.

The query translation engine 144 allows a user to specify the desired information to be searched as a simple query phrase expressed in a predefined query generation syntax 1400 (FIG. 14). This query generation syntax 1400 allows the user to specify a request with simple phrases using common terminology familiar to those in the medical industry and, in certain embodiments, in a predefined order. This ability to specify a data request in simple, intuitive phrases facilitates users skilled in health care operations to craft request of the data warehouse 142 themselves rather than relying on an intermediate individual skilled in databases.

With reference to FIG. 14, one example of a query generation syntax 1400 includes fields such as "aggregation" 1402, "value set" 1404, "taxonomy" 1408, "comparison" 1410, "time delay" 1412, "date" 1414, and "limit" 1418. This is intended to be an illustrative example and it should be understood that variations, such as in the syntax, fields and the like, are contemplated. It should be appreciated that while not all fields need be specified to generate a query, there may be a minimum set of fields specified. A phrase query in the query generation syntax 1400 must include values or entries for at least four key fields: "value set" 1404; "taxonomy" 1408; "comparison" 1410; and "limit" 1418; in the predefined order. For each field, the entry or content may be selected from a set of possible values or additional sets of values may be added on the fly such as by specifying which medical codes (CPT, ICD9, etc.) may be included in the value set. For some of the fields the user may enter additional numeric information.

The field "aggregation" 1402 may be populated with values such as age, age at, most recent, first, count, min, max, and the like. "Aggregation" 1402 may specify which portions of the data set generated in the rest of the query are included in the final result.

The field "taxonomy" 1408 may be populated with values describing the type of data being searched in common medical terms such as drug, procedure, diagnosis, result, encounter, maintenance, allergy, vitals, demographics, appointment, immunization, order, order completed, and the like.

The field "value set" 1404 may be populated by a simple description of what is being searched for in the "taxonomy" 1408 specified such as diabetes, tuberculosis, AIDS, Aspirin, Inpatient Visit, Colonoscopy, LDL, HDL, and the like.

The field "comparison" 1410 may be populated with relative statements for limiting the data of the identified "value set" 1404 taxonomy 1408 combination such as: starts before; starts after; starts during; starts concurrent with; ends before; ends after; ends during; ends concurrent with; during; and the like.

The field "date" 1414 may be populated with specifications such as: period; period end; period start; current date; and the like. Period may be passed to the query translation engine 144. The query generation module may have a predefined period or the user may be allowed to define the period in the user interaction module 112.

The field "time delay" 1412 may be utilized to further define the time period to be searched when combined with the field "date" 1414. The field "time delay" 1412 may include a numeric value, specification of a time unit, and whether it precedes or follows "date" 1414 such as: a number of years, month, days, weeks and the like; and whether this delay is before or after specified "date" 1414.

The field "limit" 1418 may include information limiting data in the previously defined set such as: limiting the data set to a range of ages; limiting the data based on responses to questions such as "Is patient a smoker?"; lab values such as LDL<100; and the like. Each limit may operate on a single numeric field where the single number field is identified based on the taxonomy 1408 value.

The user may enter a request for data as a single query phrase. The user may enter a plurality of logically combined query phrases for more complex data requests. The user may request a data metric or measure entering one or more query phrases as a numerator and one or more query phrases as a denominator in which case the query may return a ratio of the results.

With reference to FIG. 15A, a query phrase 1500 for identifying, for example, diabetes patients who were 18 or older when diagnosed is expressed using the query generation syntax 1400 (FIG. 14). In FIG. 15B that same query phrase 1500 with the values parsed into the different fields of the query generation syntax 1400. "Diagnosis" 1408A is the content for the field "taxonomy" 1408. "Diabetes" 1404A is the entry for the field "value set" 1404. "Period" 1414A is the entry for the field "date" 1414. The entry for the field "limit" 1418 is the expression "age>=18" 1418A specified for the comparison 1410A "during."

With reference to FIG. 16A, a complex, multi-phrase query 1600 is expressed using the query generation syntax 1400 described above. With respect to FIG. 16B, the same complex, multi-phrase query 1600 with the values explicitly associated with the different fields of the query generation syntax 1400 and logical operators 1602 is shown. The value set 1404B "HEDIS CAD/IVD" is searched for the taxonomy 1408B "procedure", with the comparison 1410B "during", for the date 1414B "period end" with a time delay 1412B of "3 years before." The data set identified above is restricted using the logical operator 1602 AND to add the aggregation 1402C "age at" with a limit 1418C of "between 18 and 85" at the date 1414C of "period end." The data set is further restricted using the logical operator 1602 AND to further search the value set 1404D "HEDIS CAD/IVD" for the taxonomy 1408D "diagnosis" with the comparison 1410D "during" the date 1414D "period." This example illustrates the ease with which a complex data query may be easily constructed without the need for skill with database programming languages.

With reference to FIG. 17, a request for a data metric 1700 is expressed using the query generation syntax 1400 described above. A numerator 1702 may be entered as one or more query phrases: in this example, "most recent LDL result of <100 during 1 year before period end." A denominator 1704 may be entered as one or more query phrases: in this example, "'HEDIS CAD/IVD' procedure during 3 years before period end." With respect to FIG. 18, the same data metric request 1700 with the values explicitly associated with the different fields of the query generation syntax 1400. For the numerator 1702, the value set 1404E "LDL" is searched for the taxonomy 1408E "result", with the comparison 1410E "during", for the date 1414E "period end" with a time delay 1412E of "1 years before" and a limit 1402E of "most recent." For the denominator 1704, the value set 1404F "HEDIS CAD/IVD'" is searched for the taxonomy 1408F "procedure", with the comparison 1410F "during", for the date 1414F "period end" with a time delay 1412F of "3 years before."

Figure 19:
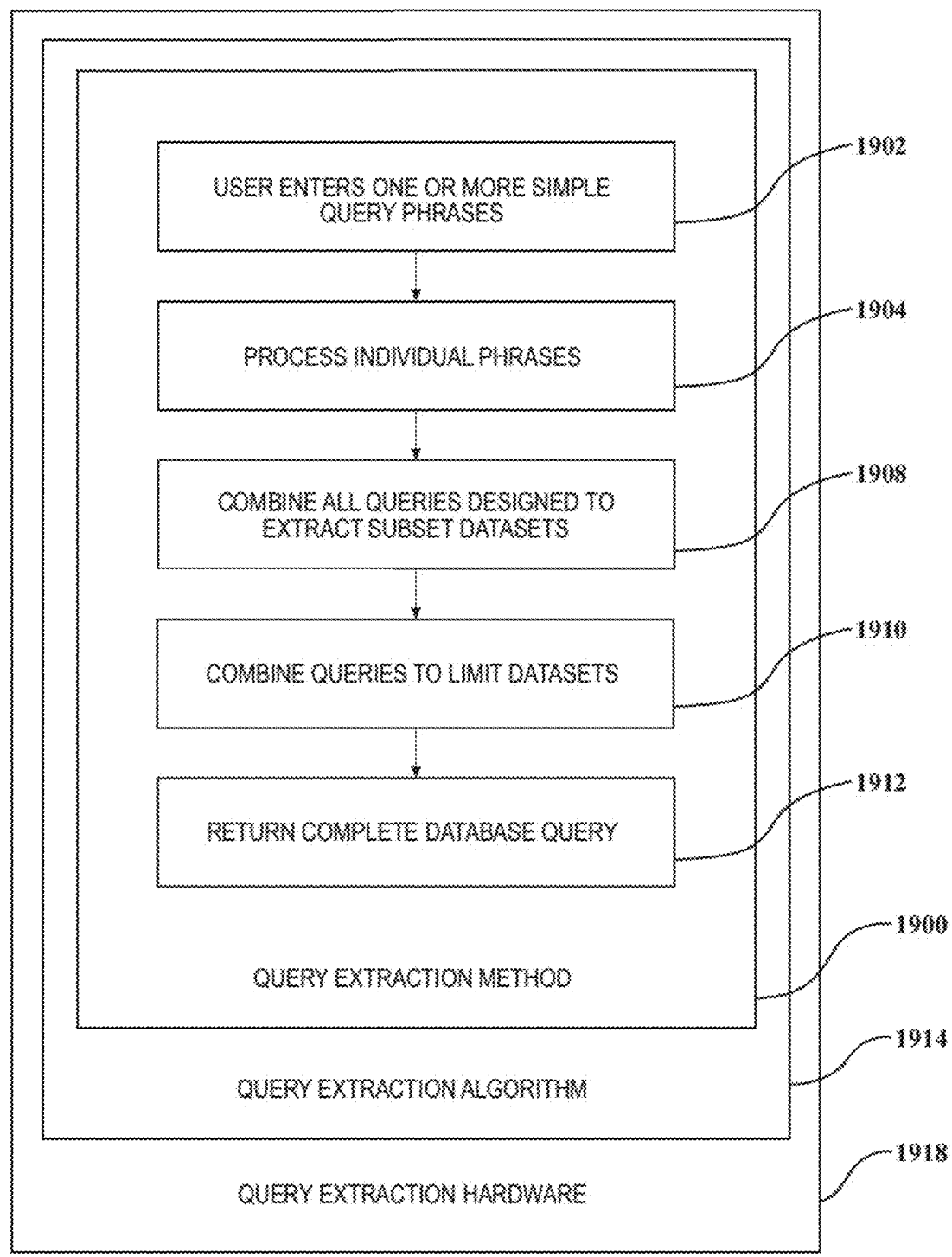
FIG. 19 shows the steps of a query extraction method.

With reference to FIG. 19, the functions of the system 100 are disclosed in terms of functional block diagrams. The operation of the system 100 according to one disclosed non-limiting embodiment generally includes a query extraction method 1900 expressed as a series of steps to transition from a metric expressed as a ratio of simple query phrases (FIG. 17) to a database query (FIG. 22A-D).

In one disclosed non-limiting embodiment, a query extraction algorithm 1914 for operation of the system 100 is schematically illustrated. The functions of the query extraction algorithm 1914 are disclosed in terms of functional block diagrams, and it should be appreciated that these functions may be enacted in either dedicated hardware circuitry or programmed software routines on computer readable storage medium capable of execution as instructions in a microprocessor based electronics control embodiment such as the system 100. That is, the query extraction hardware 1918 is an example computer storage media having embodied thereon computer-useable instructions such as an algorithm 1914 that, when executed, performs a method 1900 to transition from the simple, structured query phrase to a database query. Although particular step sequences are shown, described, and claimed, it should be understood that steps may be performed in any order, separated or combined unless otherwise indicated and will still benefit from the present disclosure.

Initially, the user enters one or more query phrases (step 1902). The query translation engine 144 then processes the individual phrases (step 1904) to result in one or more queries to extract subset datasets and, if applicable, one or more queries to limit the extracted subset datasets. The query translation engine 144 may then combine queries designed to extract subset datasets (step 1908) and combine queries designed to limit datasets (step 1910). Upon completion, the query translation engine 144 may return a complete database query (step 1912). In a series of illustrative examples, the user may enter a single query to get an absolute value such as, for example, the number of diabetics under age 20. Alternatively, the user may enter two or more query phrases to obtain a rate or ratio describing the population such as, for example, the rate of diabetics under 20 who are taking insulin.

In the non-limiting example of FIGS. 17, 18, 21, and FIGS. 22A-22D, the metric request, expressed as simple query phrases of FIG. 17, are transformed into the database query as represented in FIGS. 22A-22D. That is, the user enters a query phrase (step 1902) for the numerator 1702 and the denominator 1704 and a database query is created which, when sent to the database warehouse may return the ratio of the results of numerator 1702 divided by the denominator 1704.

Figure 20:
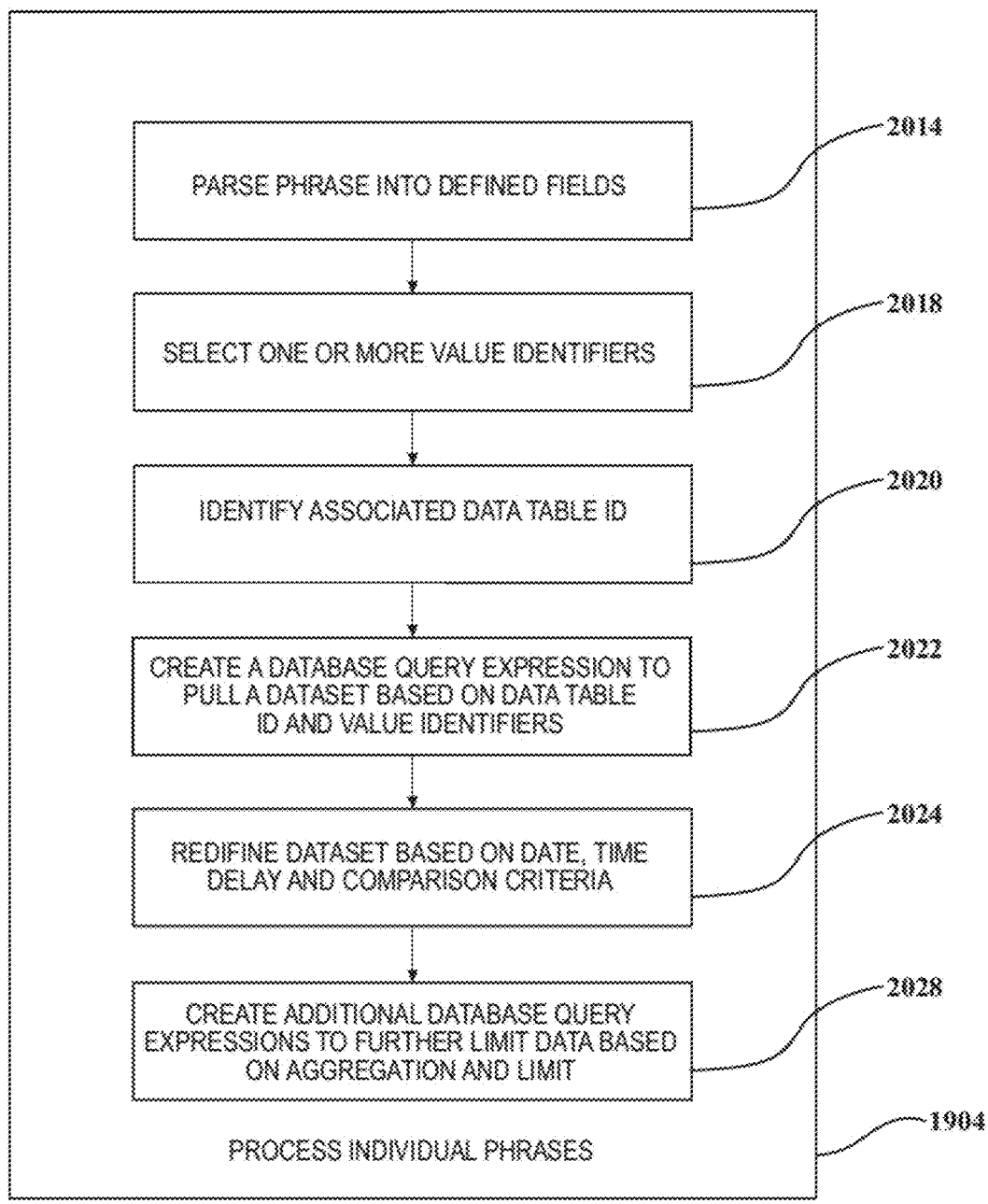
FIG. 20 shows more detail around a portion of the query extraction method.
Figure 21:
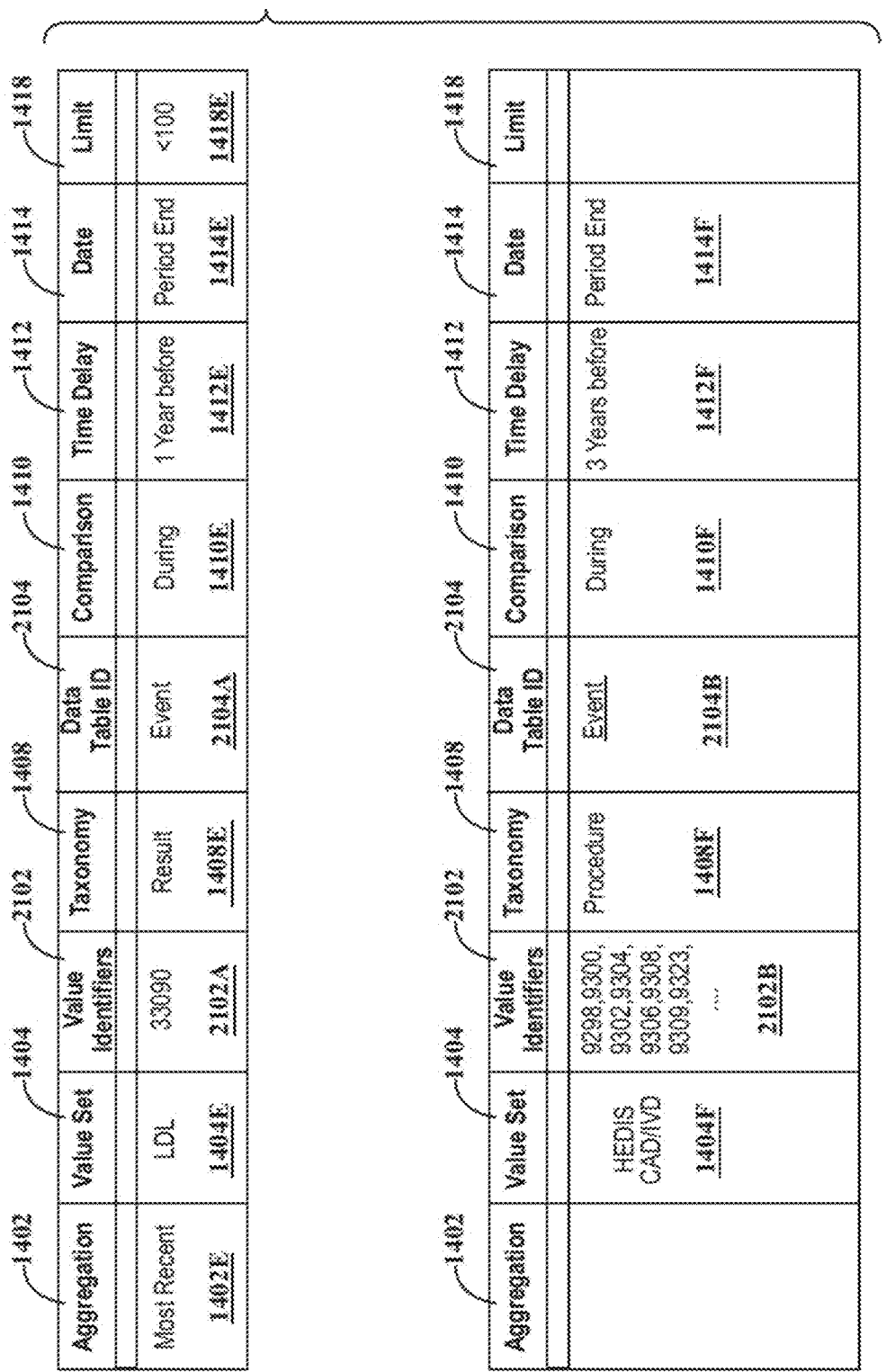
FIG. 21 shows interim results of the query extraction method.

With reference to FIG. 20, processing the individual phrases 1904 may begin with "parse phrase into defined fields" (step 2014). The entry in the "value set" 1404 field may be used to "select one or more value identifiers" (step 2018) representative of entry in "value set" 1404, referred to as value identifiers 2102 (FIG. 21). The entry in the "taxonomy" 1408 field may be used to "identify associated data table ID" (step 2020) having data relevant to the indicated "taxonomy" 1408, referred to as data table ID 2104 (FIG. 21).

The entered query phrases are then "parsed into defined fields" (step 2014). In FIG. 20, the entry for each "value set" 1404 field has been used to look up value identifiers 2102 (step 2018). For the value set "LDL" 1404E the value identifier selected is "33090" 2102A. For the value set "HEDIS CAD/IVD" 1404F a plurality of value identifiers 2102B are selected. For each entry in the "taxonomy" 1408 field has been used look up a data table ID 2104A 2104B (step 2020).

The query translation engine 144 may "create a database query expression to pull a dataset based on data table ID and value identifiers" (step 2022). The resulting database query 2200A (FIG. 22) may involve the substitution of the value identifiers 2102 and data table ID 2104 into a standard query phrase. The resulting dataset is a subset of the data in the data warehouse table identified by the data table ID 2104. The selection of entries in the dataset may be further refined by selecting entries based on the presence of one or more of the value identifiers 2102.

The query translation engine 144 is operable to "refine dataset based on date, time delay and comparison criteria" (step 2024). That is, the selection of items to retain in the dataset may be based on meeting the "comparison" 1410 criteria relative to the "date" 1414 and "time delay" 1412 specified. Based on the values specified in the "date" 1414, "comparison" 1410, and "time delay" 1412 fields, the query translation engine 144 creates a restrictive date expression 2208 that is then inserted into the database query expression 2200 created above.

The query translation engine 144 is then operable to "create additional database query expressions to further limit data based on aggregation and limit" (step 2028). That is, the phrasing and positioning of these additional restrictions varies depending on the entries for the "aggregation" field 1402 and the "limit" field 1418 as well as the entries for the other fields in query phrase. An example of a database restriction 2210 (FIG. 22C) results from the combination of the entry "most recent" 1402E for the "aggregation" field 1402 and the entry "<100" 1418E for the "limit" field 1418.

The query translation engine 144 then transforms the request specified in the query generation syntax 1400 into a database query suitable for the database system of the data warehouse 142. An illustrative and non-limiting example of the transformative power of the query translation engine 144 is represented in FIGS. 17, 18, 21, and 22A-22D.

Referring to FIG. 23, the code generated by the query translation engine 144 may generate a table of results 2300 for all patients in the practice providing detailed traceability. In the illustrative example of FIG. 23, partial results from a data query (FIG. 17) are shown illustrating examples of possible outcomes. For patients who have a positive numerator (numerator=1), the corroborating data is shown. For the query of FIG. 17, the numerator will be positive if there was an LDL test 2302 in the last year with a result 2304 less than 100. Looking at the table of results 2300 the patients having had that test with those results may be identified including when the test was done and the actual results. For patients with a positive denominator (denominator=1), the corroborating data is also shown. For the query of FIG. 17, the denominator will be positive if there was a CAD/IVD procedure 2308 during the previous three years.

The query translation engine 144 may facilitate formulation of standard data queries. The detailed results returned may be used by multiple clients to provide, for example, standard organizational reports, standard data queries to support mandated reporting, and the like. The query translation engine 144 may be used by field service individuals to create customized queries to meet a specific client's reporting needs such as tracking organizational initiatives such as cost reduction and quality improvement, patient outreach, high risk patient analysis and the like. The query translation engine 144 may be accessible to some portion of users at the client site to facilitate the creation of individual data queries. Access to different field values and different sets of the data in the data warehouse 142 may be regulated and or tracked based on user identity.

The ease of query formulation enabled by the query translation engine may facilitate the creation of new queries and retrieval of new data views in near real time by clinicians rather than database experts. This may allow clinicians to query data on the next patient in near real-time based on evolving circumstances rather than on old data.

The detailed results tables 2300 returned by the query translation engine 144 for various queries may facilitate the creation of a plurality of graphical user interfaces which provide for detailed interactions with the underlying data.

Figure 24:
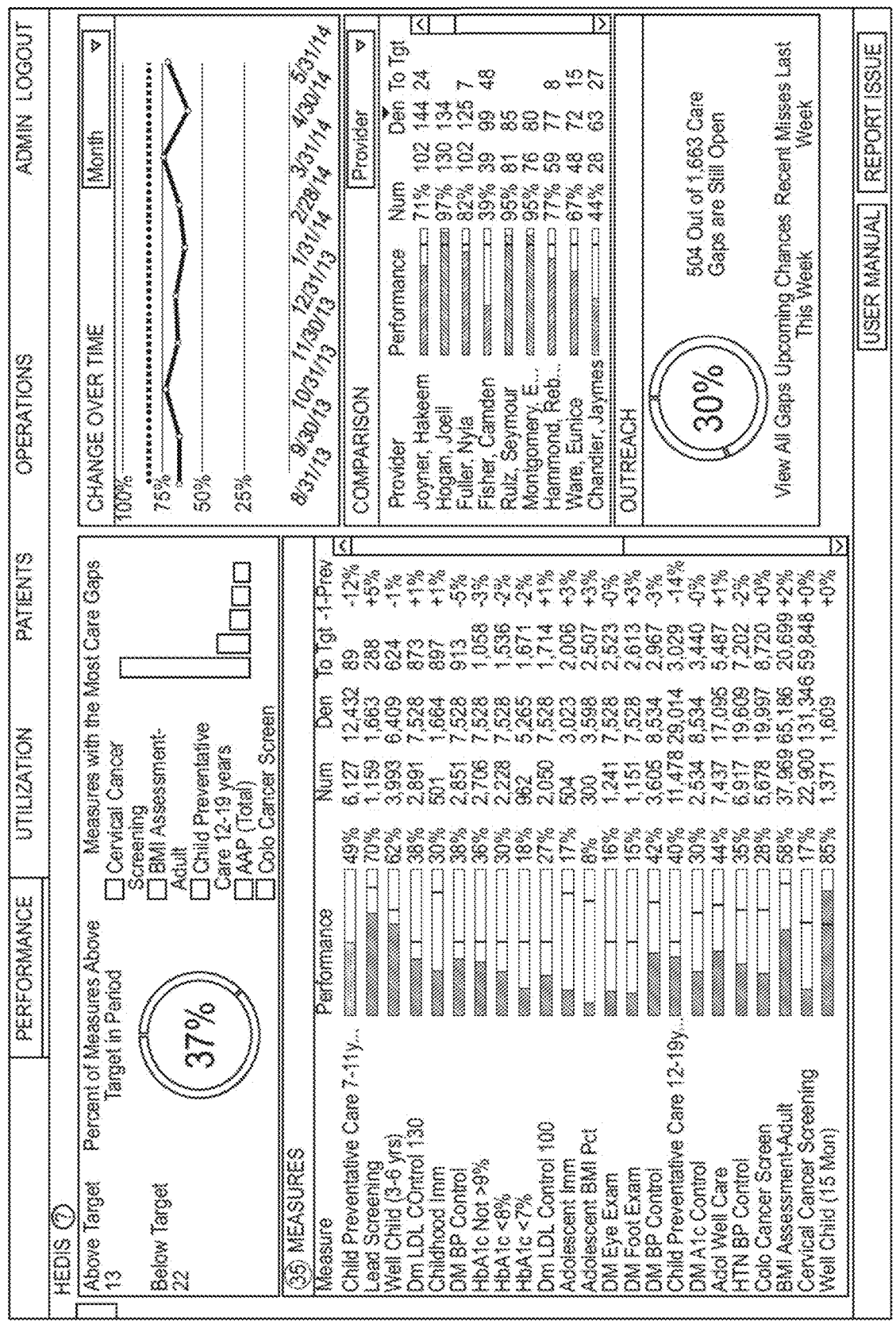
FIG. 24 shows an example of graphical user interface showing a query response summary.

Referring to FIG. 24, an illustrative example of a graphical user interface 2400 is shown which may include information such as summary data 2402, performance relative to target on specific measures 2404, trend in performance over time 2408, the ability to view the relative performance on a particular measure through a variety of filters 2410, and the ability to proactively pull up underlying results for metrics where performance is below target 2412.

Figure 25:
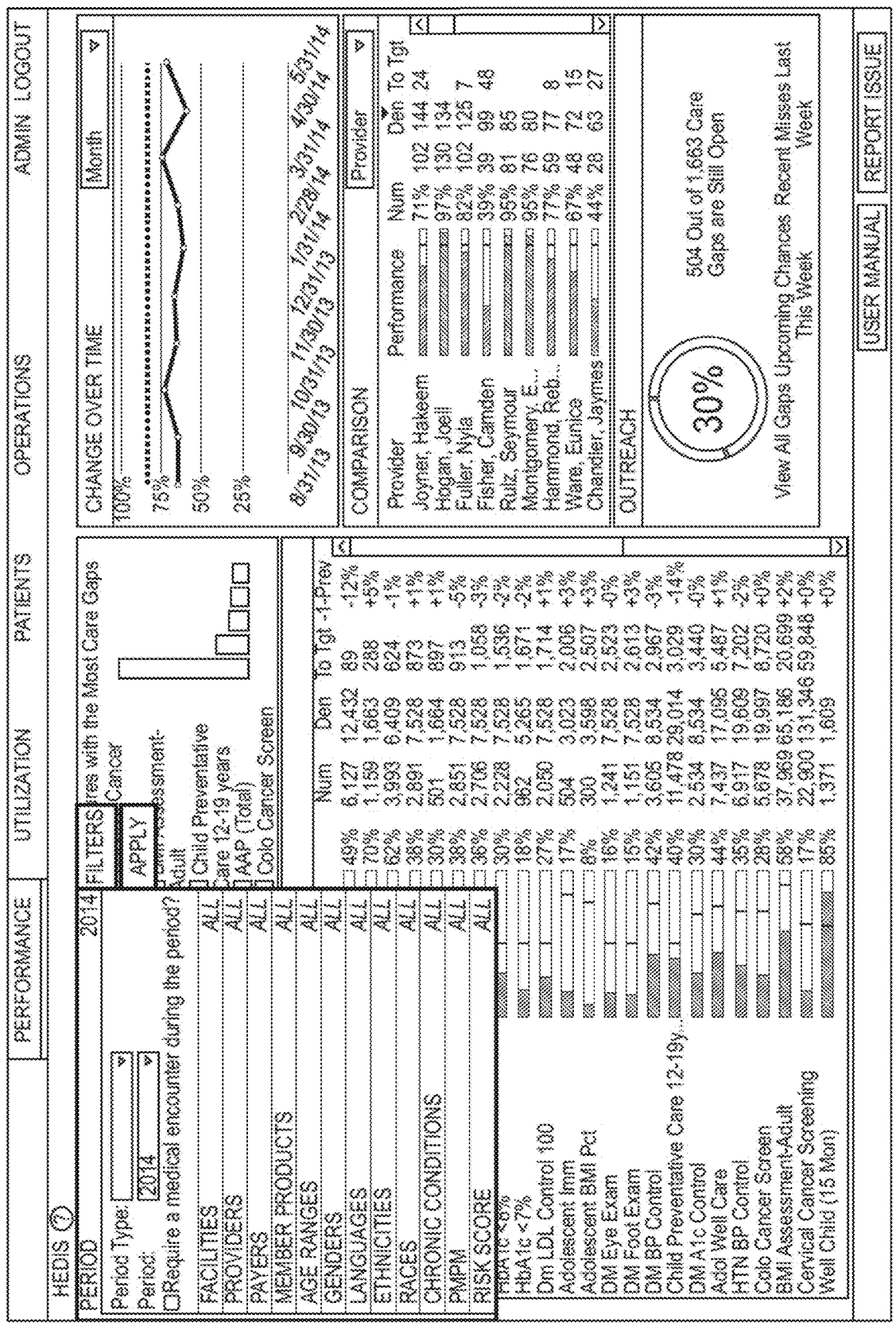
Figure 26:
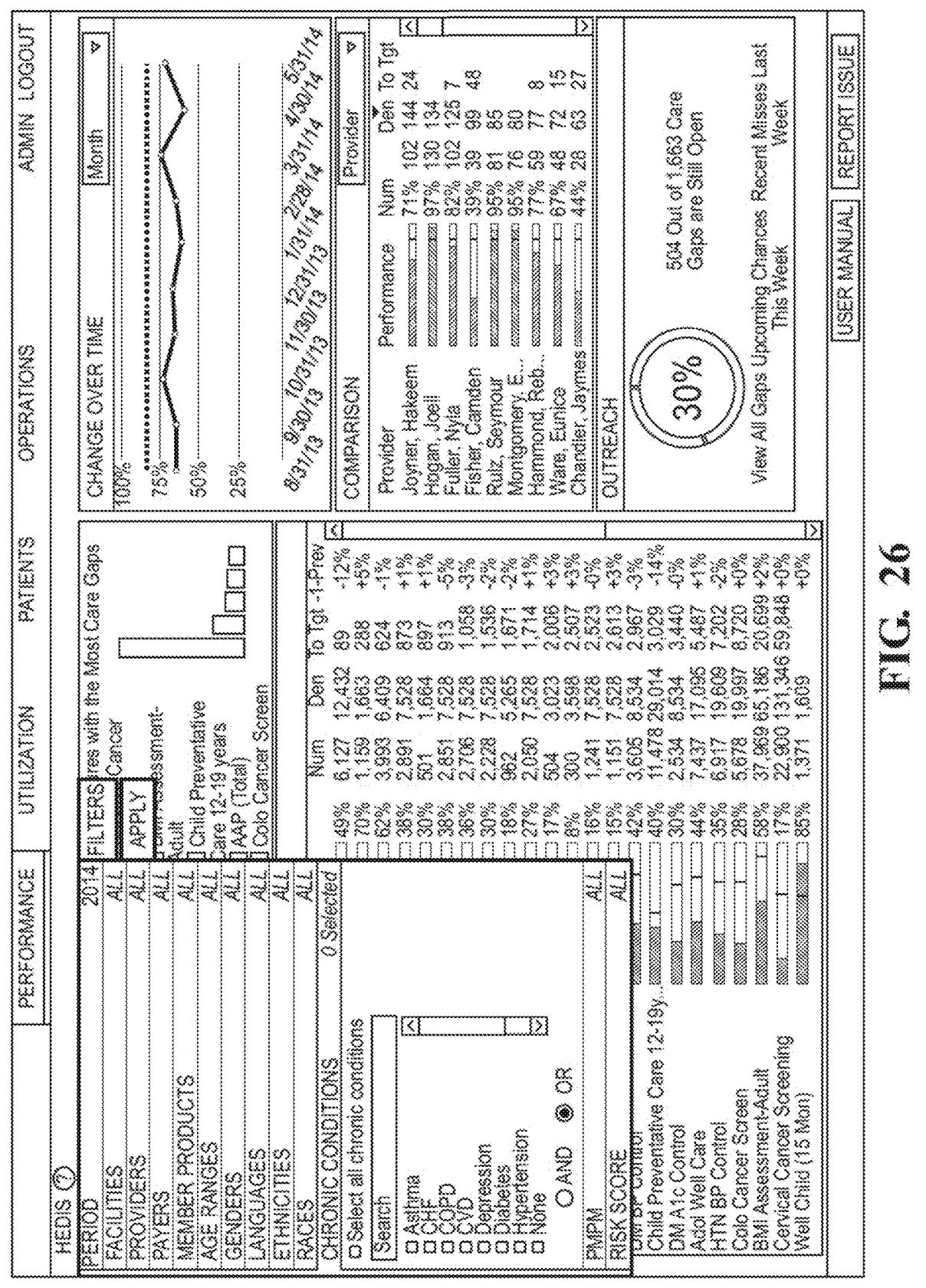

As referenced in FIG. 24, there may be an option to pull up underlying results for metrics where performance is below target 2412. Referring to FIGS. 25-26, illustrative non-limiting examples are shown demonstrating the ability to view of subset of the data by filtering by characteristics such as time period, facilities, providers, payers, different health plan products, patient demographics such as age, gender, language, ethnicity and race, presence of chronic conditions (FIG. 26), cost for a given patient or plan member per month, ("per member per month", PMPM), risk scores, and others. Referring to FIG. 27, an example of the underlying data may be seen which may include patient 2702, date for last visit 2704, interaction date 2706, next appoint 2710 and such. The underlying data may be further filtered by the patient name, numerator or denominator, additional restrictions on the data such as exclusions and exceptions, primary care provider, date of last visit or interaction, date of next appointment, and such. The integrated data may provide otherwise unforeseen insight into such areas as a client's business, health trends, patients, insurance reimbursement, information related to performance of health care providers, data to support external requests, data to support site fulfillment of various health care mandates and the like. Business insight information, such as facility usage, Emergency Department usage, identification of frequent users of client services such as ED, laboratories, insurance reimbursement rates and the like may be obtained. Patient trends may include information regarding immunization rates, patient compliance with treatments, infectious disease statistics and the like.

Information regarding health care providers may include information such as average time with patient, compliance with organizational goals such as gathering information on smoking, overall patient health and the like. Currently conventional systems often require a full day to code, and several days to test, a complex, multi-part query. Although it may possible for someone skilled with databases to generate queries to extract information, it is not ideal, since, in addition to the time element of formulating these queries, these individuals may not have the clinical or healthcare system understanding to easily develop appropriate queries to extract the information needed to provide the insights described above.

While only a few embodiments of the present disclosure have been shown and described, it will be obvious to those skilled in the art that many changes and modifications may be made thereunto without departing from the spirit and scope of the present disclosure as described in the following claims. All patent applications and patents, both foreign and domestic, and all other publications referenced herein are incorporated herein in their entireties to the full extent permitted by law.

The methods and systems described herein may be deployed in part or in whole through a machine that executes computer software, program codes, and/or instructions on a processor. The processor may be part of a server, cloud server, client, network infrastructure, mobile computing platform, stationary computing platform, or other computing platform. A processor may be any kind of computational or processing device capable of executing program instructions, codes, binary instructions and the like. The processor may be or include a signal processor, digital processor, embedded processor, microprocessor or any variant such as a co-processor (math co-processor, graphic co-processor, communication co-processor and the like) and the like that may directly or indirectly facilitate execution of program code or program instructions stored thereon. In addition, the processor may enable execution of multiple programs, threads, and codes. The threads may be executed simultaneously to enhance the performance of the processor and to facilitate simultaneous operations of the application. By way of implementation, methods, program codes, program instructions and the like described herein may be implemented in one or more thread. The thread may spawn other threads that may have assigned priorities associated with them; the processor may execute these threads based on priority or any other order based on instructions provided in the program code. The processor may include memory that stores methods, codes, instructions and programs as described herein and elsewhere. The processor may access a storage medium through an interface that may store methods, codes, and instructions as described herein and elsewhere. The storage medium associated with the processor for storing methods, programs, codes, program instructions or other type of instructions capable of being executed by the computing or processing device may include but may not be limited to one or more of a CD-ROM, DVD, memory, hard disk, flash drive, RAM, ROM, cache and the like.

A processor may include one or more cores that may enhance speed and performance of a multiprocessor. In embodiments, the process may be a dual core processor, quad core processors, other chip-level multiprocessor and the like that combine two or more independent cores (called a die).

The methods and systems described herein may be deployed in part or in whole through a machine that executes computer software on a server, cloud server, client, firewall, gateway, hub, router, or other such computer and/or networking hardware. The software program may be associated with a server that may include a file server, print server, domain server, internet server, intranet server and other variants such as secondary server, host server, distributed server and the like. The server may include one or more of memories, processors, computer readable media, storage media, ports (physical and virtual), communication devices, and interfaces capable of accessing other servers, clients, machines, and devices through a wired or a wireless medium, and the like. The methods, programs or codes as described herein and elsewhere may be executed by the server. In addition, other devices required for execution of methods as described in this application may be considered as a part of the infrastructure associated with the server.

The server may provide an interface to other devices including, without limitation, clients, other servers, printers, database servers, print servers, file servers, communication servers, distributed servers and the like. Additionally, this coupling and/or connection may facilitate remote execution of program across the network. The networking of some or all of these devices may facilitate parallel processing of a program or method at one or more location without deviating from the scope of the disclosure. In addition, any of the devices attached to the server through an interface may include at least one storage medium capable of storing methods, programs, code and/or instructions. A central repository may provide program instructions to be executed on different devices. In this implementation, the remote repository may act as a storage medium for program code, instructions, and programs.

The software program may be associated with a client that may include a file client, print client, domain client, internet client, intranet client and other variants such as secondary client, host client, distributed client and the like. The client may include one or more of memories, processors, computer readable media, storage media, ports (physical and virtual), communication devices, and interfaces capable of accessing other clients, servers, machines, and devices through a wired or a wireless medium, and the like. The methods, programs or codes as described herein and elsewhere may be executed by the client. In addition, other devices required for execution of methods as described in this application may be considered as a part of the infrastructure associated with the client.

The client may provide an interface to other devices including, without limitation, servers, other clients, printers, database servers, print servers, file servers, communication servers, distributed servers and the like. Additionally, this coupling and/or connection may facilitate remote execution of program across the network. The networking of some or all of these devices may facilitate parallel processing of a program or method at one or more location without deviating from the scope of the disclosure. In addition, any of the devices attached to the client through an interface may include at least one storage medium capable of storing methods, programs, applications, code and/or instructions. A central repository may provide program instructions to be executed on different devices. In this implementation, the remote repository may act as a storage medium for program code, instructions, and programs.

The methods and systems described herein may be deployed in part or in whole through network infrastructures. The network infrastructure may include elements such as computing devices, servers, routers, hubs, firewalls, clients, personal computers, communication devices, routing devices and other active and passive devices, modules and/or components as known in the art. The computing and/or non-computing device(s) associated with the network infrastructure may include, apart from other components, a storage medium such as flash memory, buffer, stack, RAM, ROM and the like. The processes, methods, program codes, instructions described herein and elsewhere may be executed by one or more of the network infrastructural elements.

The methods, program codes, and instructions described herein and elsewhere may be implemented on a cellular network having multiple cells. The cellular network may either be frequency division multiple access (FDMA) network or code division multiple access (CDMA) network. The cellular network may include mobile devices, cell sites, base stations, repeaters, antennas, towers, and the like. The cell network may be a GSM, GPRS, 3G, EVDO, mesh, or other networks types.

The methods, programs codes, and instructions described herein and elsewhere may be implemented on or through mobile devices. The mobile devices may include navigation devices, cell phones, mobile phones, mobile personal digital assistants, laptops, palmtops, netbooks, pagers, electronic books readers, music players and the like. These devices may include, apart from other components, a storage medium such as a flash memory, buffer, RAM, ROM and one or more computing devices. The computing devices associated with mobile devices may be enabled to execute program codes, methods, and instructions stored thereon.

Alternatively, the mobile devices may be configured to execute instructions in collaboration with other devices. The mobile devices may communicate with base stations interfaced with servers and configured to execute program codes. The mobile devices may communicate on a peer to peer network, mesh network, or other communications network. The program code may be stored on the storage medium associated with the server and executed by a computing device embedded within the server. The base station may include a computing device and a storage medium. The storage device may store program codes and instructions executed by the computing devices associated with the base station.

The computer software, program codes, and/or instructions may be stored and/or accessed on machine readable media that may include: computer components, devices, and recording media that retain digital data used for computing for some interval of time; semiconductor storage known as random access memory (RAM); mass storage typically for more permanent storage, such as optical discs, forms of magnetic storage like hard disks, tapes, drums, cards and other types; processor registers, cache memory, volatile memory, non-volatile memory; optical storage such as CD, DVD; removable media such as flash memory (e.g. USB sticks or keys), floppy disks, magnetic tape, paper tape, punch cards, standalone RAM disks, Zip drives, removable mass storage, off-line, and the like; other computer memory such as dynamic memory, static memory, read/write storage, mutable storage, read only, random access, sequential access, location addressable, file addressable, content addressable, network attached storage, storage area network, bar codes, magnetic ink, and the like.

The methods and systems described herein may transform physical and/or or intangible items from one state to another. The methods and systems described herein may also transform data representing physical and/or intangible items from one state to another, such as from usage data to a normalized usage dataset.

The elements described and depicted herein, including in flow charts and block diagrams throughout the figures, imply logical boundaries between the elements. However, according to software or hardware engineering practices, the depicted elements and the functions thereof may be implemented on machines through computer executable media having a processor capable of executing program instructions stored thereon as a monolithic software structure, as standalone software modules, or as modules that employ external routines, code, services, and so forth, or any combination of these, and all such implementations may be within the scope of the present disclosure. Examples of such machines may include, but may not be limited to, personal digital assistants, laptops, personal computers, mobile phones, other handheld computing devices, medical equipment, wired or wireless communication devices, transducers, chips, calculators, satellites, tablet PCs, electronic books, gadgets, electronic devices, devices having artificial intelligence, computing devices, networking equipment, servers, routers and the like. Furthermore, the elements depicted in the flow chart and block diagrams or any other logical component may be implemented on a machine capable of executing program instructions. Thus, while the foregoing drawings and descriptions set forth functional aspects of the disclosed systems, no particular arrangement of software for implementing these functional aspects should be inferred from these descriptions unless explicitly stated or otherwise clear from the context. Similarly, it will be appreciated that the various steps identified and described above may be varied, and that the order of steps may be adapted to particular applications of the techniques disclosed herein. All such variations and modifications are intended to fall within the scope of this disclosure. As such, the depiction and/or description of an order for various steps should not be understood to require a particular order of execution for those steps, unless required by a particular application, or explicitly stated or otherwise clear from the context.

The methods and/or processes described above, and steps thereof, may be realized in hardware, software or any combination of hardware and software suitable for a particular application. The hardware may include a computer which may be a dedicated computing device, specific computing device or particular aspect or component of a specific computing device. The processes may be realized in one or more microprocessors, microcontrollers, embedded microcontrollers, programmable digital signal processors or other programmable device, along with internal and/or external memory. The processes may also, or instead, be embodied in an application specific integrated circuit, a programmable gate array, programmable array logic, or any other device or combination of devices that may be configured to process electronic signals. It will further be appreciated that one or more of the processes may be realized as a computer executable code capable of being executed on a machine readable medium.

The computer executable code may be created using a structured programming language such as C, an object oriented programming language such as C++, or any other high-level or low-level programming language (including assembly languages, hardware description languages, and database programming languages and technologies) that may be stored, compiled or interpreted to run on one of the above devices, as well as heterogeneous combinations of processors, processor architectures, or combinations of different hardware and software, or any other machine capable of executing program instructions.

Thus, in one aspect, each method described above and combinations thereof may be embodied in computer executable code that, when executing on one or more computing devices, performs the steps thereof. In another aspect, the methods may be embodied in systems that perform the steps thereof, and may be distributed across devices in a number of ways, or all of the functionality may be integrated into a dedicated, standalone device or other hardware. In another aspect, the methods, structures, facilities or means for performing the steps associated with the processes described above may include any of the hardware and/or software described above. All such permutations and combinations are intended to fall within the scope of the present disclosure.

Although the different non-limiting embodiments have specific illustrated components, the embodiments of this invention are not limited to those particular combinations. It is possible to use some of the components or features from any of the non-limiting embodiments in combination with features or components from any of the other non-limiting embodiments.

It should be appreciated that like reference numerals identify corresponding or similar elements throughout the several drawings. It should also be appreciated that although a particular component arrangement is disclosed in the illustrated embodiment, other arrangements will benefit herefrom.

Although particular step sequences are shown, described, and claimed, it should be understood that steps may be performed in any order, separated or combined unless otherwise indicated and will still benefit from the present disclosure.

All documents referenced herein are hereby incorporated by reference.

What is claimed is:

1. A method of generating a clinically supplemented risk score by an electronic health record system having one or more processors, the method comprising:
   collecting, via at least one of the one or more processors, data from a plurality of electronic health records of a patient;
   parsing, via at least one of the one or more processors, the data into defined fields to generate parsed data;
   determining a closed risk score in response to a documented diagnostic condition of the patient in the plurality of electronic health records;
   comparing, via at least one of the one or more processors, the parsed data to at least one look-up table to generate an inferred diagnostic condition;
   comparing, via at least one of the one or more processors, the inferred diagnostic condition to the documented diagnostic condition of the patient in the plurality of electronic health records, thereby determining the documented diagnostic condition is not associated with the inferred diagnostic condition;
   mapping, via at least one of the one or more processors, the inferred diagnostic condition to at least one condition category to generate at least one mapped inferred diagnostic condition;
   refining, via at least one of the one or more processors, the at least one mapped inferred diagnostic condition into a hierarchy to generate a hierarchal mapped conditioned category;
   determining an open risk score in response to the hierarchal mapped condition category of the at least one mapped inferred diagnostic condition; and
   determining, via at least one of the one or more processors, a risk score in response to open risk score and the closed risk score, the risk score representing an expected total cost of care for the patient relative to the average per-patient cost of care over an entire population.

2. The method as recited in claim 1, further comprising identifying a physician associated with determining the documented diagnostic condition.

3. The method as recited in claim 1, further comprising identifying that the inferred diagnostic condition is associated with a medication.

4. The method as recited in claim 1, wherein the inferred diagnostic condition is determined retroactively.

5. The method as recited in claim 1, wherein the parsed data is based on a presence of a diagnosis code.

6. The method as recited in claim 5, wherein comparing the parsed data includes processing text notations to identify phrases that are then mapped to the diagnosis code.

7. The method as recited in claim 6, wherein comparing the parsed data includes identifying a previously un-notated condition.

8. The method as recited in claim 1, wherein the inferred diagnostic condition is inferred from medication records.

9. The method as recited in claim 1, wherein the inferred diagnostic condition is inferred from laboratory results.

10. The method as recited in claim 1, wherein the inferred diagnostic condition is inferred from patient vitals over a time period.

11. The method as recited in claim 1, further comprising:
    determining the inferred diagnostic condition from a subset of the data;
    determining the lack of an associated diagnosis code for the inferred diagnostic condition in the plurality of electronic health records of a patient; and
    identifying the inferred diagnostic condition as a risk.

12. The method as recited in claim 11, wherein the subset of the data is from at least one of medication records, laboratory results and patient vitals over a time period.

13. The method of claim 1, further comprising calculating, via at least one of the one or more processors, measures of personnel activity with reference to personnel type, time of personnel activity and an electronic health record module of the personnel activity to demonstrate workflow distribution among support staff and providers, wherein at least one measure of personnel activity is determined by calculating a number of manipulations of user input devices and a time period spent manipulating the user input devices within a field of any of the plurality of electronic health records; and wherein the step of determining the risk score utilizes the measures of personnel activity as a source of data for the risk score.

14. The method of claim 1, wherein the inferred diagnostic condition is determined based on a calendar time interval.

15. The method of claim 14, wherein the risk score is updated for the patient based on the calendar time interval, and for a population of interest, wherein the population of interest includes the patient.

16. A method of generating a clinically supplemented risk score by an electronic health record system having one or more processors, the method comprising:
    collecting data from a plurality of electronic health records of a patient via an electronic health record system having one or more processors;
    determining a closed risk score based on a documented diagnostic condition from the plurality of electronic health records;
    determining, via at least one of the one or more processors, an inferred diagnostic condition from the plurality of electronic health records;
    determining, via at least one of the one or more processors, the lack of an associated documented diagnostic condition for the inferred diagnostic condition;
    identifying, via at least one of the one or more processors, the inferred diagnostic condition as a risk;
    determining an open risk score in response to the identified inferred diagnostic condition; and
    determining, via at least one of the one or more processors, a risk score in response to the open risk score and the closed risk score for the patient, the risk score representing an expected total cost of care for the patient relative to the average per-patient cost of care over an entire population.

17. The method as recited in claim 16, wherein the documented diagnostic condition is based on a diagnosis code.

18. The method as recited in claim 17, further composing processing text notations to identify phrases that are then mapped to the diagnosis code.

19. The method as recited in claim 16, wherein determining the inferred diagnostic condition is from parsed data.

20. The method as recited in claim 19, wherein the parsed data includes at least one of medication records, laboratory results, and patient vitals over a time period.

* * * * *

UNITED STATES PATENT AND TRADEMARK OFFICE
CERTIFICATE OF CORRECTION

PATENT NO. : 10,832,819 B2
APPLICATION NO. : 14/815290
DATED : November 10, 2020
INVENTOR(S) : Michael A. Simon et al.

It is certified that error appears in the above-identified patent and that said Letters Patent is hereby corrected as shown below:

In the Specification

In Column 2, Line 22, delete "language" and insert -- language. --, therefor.

In Column 3, Line 63, delete "coefficient" and insert -- coefficient. --, therefor.

In Column 11, Line 55, delete "staff" and insert -- staff. --, therefor.

In Column 11, Line 59, delete "staff" and insert -- staff. --, therefor.

In Column 11, Line 63, delete "staff" and insert -- staff. --, therefor.

In Column 15, Line 8, delete "condition" and insert -- condition. --, therefor.

In Column 15, Line 48, delete "data" and insert -- data. --, therefor.

In Column 16, Line 24, delete "conditions" and insert -- conditions. --, therefor.

In Column 16, Line 38, delete "syntax" and insert -- syntax. --, therefor.

In Column 21, Line 4, delete "processes" and insert -- processes. --, therefor.

In Column 25, Line 18, delete "staff" and insert -- staff. --, therefor.

In Column 27, Line 52, delete "et.c," and insert -- etc., --, therefor.

In Column 30, Line 18, after "may" insert -- be --.

In Column 41, Line 56, delete "and or" and insert -- and/or --, therefor.

Signed and Sealed this
Nineteenth Day of January, 2021

Andrei Iancu
*Director of the United States Patent and Trademark Office*